United States Patent
Pandey et al.

(10) Patent No.: US 9,644,195 B2
(45) Date of Patent: May 9, 2017

(54) COMPOUNDS AND METHODS FOR PURIFICATION OF SERINE PROTEASES

(71) Applicant: Portola Pharmaceuticals, Inc., South San Francisco, CA (US)

(72) Inventors: Anjali Pandey, Fremont, CA (US); Jack W. Rose, San Mateo, CA (US)

(73) Assignee: Portola Pharmaceuticals, Inc., South San Francsico, CA (US)

( * ) Notice: Subject to any disclaimer, the term of this patent is extended or adjusted under 35 U.S.C. 154(b) by 0 days.

(21) Appl. No.: 14/723,395

(22) Filed: May 27, 2015

(65) Prior Publication Data

US 2015/0337285 A1  Nov. 26, 2015

Related U.S. Application Data

(63) Continuation of application No. 14/142,655, filed on Dec. 27, 2013, now abandoned, which is a continuation-in-part of application No. 13/830,372, filed on Mar. 14, 2013, now Pat. No. 9,200,268.

(60) Provisional application No. 61/746,544, filed on Dec. 27, 2012.

(51) Int. Cl.
| | |
|---|---|
| *C07D 221/06* | (2006.01) |
| *C12N 9/64* | (2006.01) |
| *C07D 213/72* | (2006.01) |
| *B01J 20/26* | (2006.01) |
| *B01J 20/286* | (2006.01) |
| *C07D 213/75* | (2006.01) |

(52) U.S. Cl.
CPC .......... *C12N 9/6432* (2013.01); *B01J 20/267* (2013.01); *B01J 20/286* (2013.01); *C07D 213/72* (2013.01); *C07D 213/75* (2013.01); *C12N 9/6424* (2013.01); *B01J 2220/80* (2013.01); *C12Y 304/21006* (2013.01)

(58) Field of Classification Search
None
See application file for complete search history.

(56) References Cited

U.S. PATENT DOCUMENTS

| | | | |
|---|---|---|---|
| 6,376,515 B2 | 4/2002 | Zhu et al. | |
| 6,835,739 B2 | 12/2004 | Zhu et al. | |
| 6,844,367 B1 | 1/2005 | Zhu et al. | |
| 7,285,565 B2 | 10/2007 | Zhu et al. | |
| 7,314,874 B2 | 1/2008 | Zhu et al. | |
| 7,342,013 B2 | 3/2008 | Zhu et al. | |
| 7,598,276 B2 | 10/2009 | Grant et al. | |
| 7,700,628 B2 | 4/2010 | Argade et al. | |
| 8,063,036 B2 | 11/2011 | Zhu et al. | |
| 8,153,390 B2 | 4/2012 | Bradshaw et al. | |
| 8,268,783 B2 * | 9/2012 | Sinha ................. | A61K 38/4826 424/185.1 |
| 8,394,964 B2 | 3/2013 | Pandey et al. | |
| 8,404,724 B2 | 3/2013 | Sinha et al. | |
| 8,455,440 B2 | 6/2013 | Sinha et al. | |
| 8,518,977 B2 | 8/2013 | Zhu et al. | |
| 8,524,907 B2 | 9/2013 | Scarborough et al. | |
| 8,557,852 B2 | 10/2013 | Grant et al. | |
| 8,691,847 B2 | 4/2014 | Zhu et al. | |
| 2012/0071519 A1 | 3/2012 | Capodanno et al. | |
| 2012/0095019 A1 | 4/2012 | Sinha et al. | |
| 2013/0064806 A1 | 3/2013 | Grant et al. | |
| 2013/0211094 A1 | 8/2013 | Pandey et al. | |
| 2013/0230901 A1 | 9/2013 | Lu et al. | |
| 2013/0315897 A1 | 11/2013 | Sinha et al. | |
| 2014/0046071 A1 | 2/2014 | Scarborough et al. | |
| 2014/0186923 A1 | 7/2014 | Pandey et al. | |
| 2014/0346397 A1 | 11/2014 | Pandey et al. | |

FOREIGN PATENT DOCUMENTS

| | | |
|---|---|---|
| WO | WO-01/19788 | 3/2001 |
| WO | WO-01/64643 | 9/2001 |
| WO | WO-2006/057845 | 6/2006 |
| WO | WO-2013/188587 | 12/2013 |

OTHER PUBLICATIONS

Rameshwar, N. et al, "Qsar studies of n1-(5-chloro-t-pyridyl)-2-{[4-(alkylmethyl))enzoyl]amino}-5-chlorobenzamide analogs." Bioorg. Med. Chem. (2006) 14 p. 319-325.*
Neitzel, James J., "Enzyme catalysis: the serine proteases." Nature Education (2010) 3(9):21.*
Portola pharmaceuticals press release, Oct. 15, 2015, available at http://investors.portola.com/phoenix.zhtml?c=198136&p=irol-newsArticle&id=2096451.*
Yampolsky, Lev Y. and Stoltzfus, Arlin, "THe exchangeability of amino acids in proteins." Genetics (2005) 170 p. 1459-1472.*
Pol-Fachin, L. and Verli, H., "Atomic-level details on thrombin and fXa allosteric inhibition by heparin." SBBq conference, May 19, 2012.*
International Preliminary Report on Patentability in International Application No. PCT/US2013/078130 dated Jun. 30, 2015, 8 pages.
International Search Report in International Application No. PCT/US2013/078130 dated May 22, 2014, 5 pages.
Berge, et al., "Pharmaceutical Salts", *Journal of Pharmaceutical Science*, (1977), 66(1): 1-19.
Communication Relating to the Results of the Partial International Search from International Application No. PCT/US2013/078130, dated Mar. 5, 2014.
Cuatrecasas, "Protein purification by affinity chromatography," J. Biol. Chem., (1970), 245(12), 3059-3065.
GalxoWellcome Pharmacology Guide, http://www.pdg.cnb.usam.es/cursos/Barcelona2002/pp./Farmac/Comput_Lab/Guia_Glaxo/chap3c.html, downloaded May 15, 2014.
GE Healthcare,"EAH Sepharose™ 4B," Instructions 71-7097-00, by General Electric Company (2009).

(Continued)

*Primary Examiner* — Maury Audet
*Assistant Examiner* — Fred Reynolds
(74) *Attorney, Agent, or Firm* — Sheppard Mullin Richter & Hampton LLP

(57) ABSTRACT

Disclosed herein are compounds, compositions, methods and kits for purifying a serine protease and serine proteases purified with the compounds, compositions and methods.

10 Claims, 13 Drawing Sheets

(56) References Cited

OTHER PUBLICATIONS

GE Healthcare Life Sciences, "CNBr-activated Sepharose™ 4 Fast Flow," Instructions 71-5000-15 AF, General Electric Company (2011).

GE Healthcare Life Sciences, "NHS-activated Sepharose™ 4 Fast Flow," Instructions 71-5000-14 AD, General Electric Company (2011).

GE Healthcare Life Sciences, "Multimodal Chromatography Handbook," GE publication 29-0548-08aa, published Nov. 2013.

Gotoh, et al, "Isolation of factor Xa from chick embryo as the amniotic endoprotease responsible for paramyxovirus activation," FEBS, (1992), 296(3), 274-278.

International Search Report and Written Opinion for PCT/US2013/078130 dated May 22, 2014.

Kusmič, et al., "High-Throughput Screening of Enyzme Inhibitors: Automatic Determination of Tight-Binding Inhibition Constants," *Analytical Biochemistry*, (2000), 281:62-67.

Lockhart, et al., "Geonomics, gene expression and DNA arrays," *Nature*, (2000), 405:827-836.

Non Final Office Action dated May 23, 2014 in related U.S. Appl. No. 13/830,372.

Pinto, et al., "Factor Xa Inhibitors: Next-Generation Antithrombotic Agents," *Journal of Medicinal Chemistry*, (2010) 53(17):6243-6274.

Rameshwar, et al; "Qsar studies of $N_1$-(5-chloro-2pryidyl)-2-{[4-(alkyl methyl)benzoyl]amino}-5-chlorobenzmide analogs," *Bioorg. Med. Chem.*, (2006) 14(2):319-325.

Schönherr, et al., "Profound Methyl Effects in Drug Discovery and a Call for New C—H Methylation Reactions," *Angewante Chemie*, (2013), 52:12256-12267.

Srinivas, "Proteomics in Early Detection of Cancer," *Clin. Chem.*, (2000), 47(10):1901-1911.

Zhu, et al; "Inhibitory effect of carboxylic acid group in hERG binding," *Bioorg. Med. Chem. Lett.* (2006), 16(21):5507-5512.

\* cited by examiner

SEQ ID NO: 1:

| | | | | | | | | | | | | | | |
|---|---|---|---|---|---|---|---|---|---|---|---|---|---|---|
| Ala | Asn | Ser | Phe | Leu | Phe | Trp | Asn | Lys | Tyr | Lys | Asp | Gly | Asp | Gln | Cys |
| 1 | | | | 5 | | | | | 10 | | | | | 15 | |
| Glu | Thr | Ser | Pro | Cys | Gln | Asn | Gln | Gly | Lys | Cys | Lys | Asp | Gly | Leu | Gly |
| | | | 20 | | | | | 25 | | | | | 30 | | |
| Glu | Tyr | Thr | Cys | Thr | Cys | Leu | Glu | Gly | Phe | Glu | Gly | Lys | Asn | Cys | Glu |
| | | 35 | | | | | 40 | | | | | 45 | | | |
| Leu | Phe | Thr | Arg | Lys | Leu | Cys | Ser | Leu | Asp | Asn | Gly | Asp | Cys | Asp | Gln |
| 50 | | | | | 55 | | | | | 60 | | | | | |
| Phe | Cys | His | Glu | Glu | Gln | Asn | Ser | Val | Val | Cys | Ser | Cys | Ala | Arg | Gly |
| 65 | | | | 70 | | | | | 75 | | | | | 80 | |

Ala Asn Ser Phe Leu Phe Trp Asn Lys Tyr Lys Asp Gly Asp Gln Cys
1                   5                         10                          15
Glu Thr Ser Pro Cys Gln Asn Gln Gly Lys Cys Lys Asp Gly Leu Gly
            20                        25                        30
Glu Tyr Thr Cys Thr Cys Leu Glu Gly Phe Glu Gly Lys Asn Cys Glu
        35                        40                        45
Leu Phe Thr Arg Lys Leu Cys Ser Leu Asp Asn Gly Asp Cys Asp Gln
50                      55                      60
Phe Cys His Glu Glu Gln Asn Ser Val Val Cys Ser Cys Ala Arg Gly
65              70                      75                      80
Tyr Thr Leu Ala Asp Asn Gly Lys Ala Cys Ile Pro Thr Gly Pro Tyr
                85                      90                      95
Pro Cys Gly Lys Gln Thr Leu Glu Arg Arg Lys Arg Arg Lys Arg Ile
            100                       105                       110
Val Gly Gly Gln Glu Cys Lys Asp Gly Glu Cys Pro Trp Gln Ala Leu
            115                       120                       125
Leu Ile Asn Glu Glu Asn Glu Gly Phe Cys Gly Gly Thr Ile Leu Ser
    130                       135                       140
Glu Phe Tyr Ile Leu Thr Ala Ala His Cys Leu Tyr Gln Ala Lys Arg
145                       150                       155                       160
Phe Lys Val Arg Val Gly Asp Arg Asn Thr Glu Gln Glu Glu Gly Gly
                165                       170                       175
Glu Ala Val His Glu Val Glu Val Val Ile Lys His Asn Arg Phe Thr
                180                       185                       190
Lys Glu Thr Tyr Asp Phe Asp Ile Ala Val Leu Arg Leu Lys Thr Pro
            195                       200                       205
Ile Thr Phe Arg Met Asn Val Ala Pro Ala Cys Leu Pro Glu Arg Asp
    210                       215                       220
Trp Ala Glu Ser Thr Leu Met Thr Gln Lys Thr Gly Ile Val Ser Gly
225                       230                       235                       240
Phe Gly Arg Thr His Glu Lys Gly Arg Gln Ser Thr Arg Leu Lys Met
                245                       250                       255
Leu Glu Val Pro Tyr Val Asp Arg Asn Ser Cys Lys Leu Ser Ser Ser
            260                       265                       270
Phe Ile Ile Thr Gln Asn Met Phe Cys Ala Gly Tyr Asp Thr Lys Gln
            275                       280                       285
Glu Asp Ala Cys Gln Gly Asp Ala Gly Gly Pro His Val Thr Arg Phe
    290                       295                       300
Lys Asp Thr Tyr Phe Val Thr Gly Ile Val Ser Trp Gly Glu Gly Cys
305                       310                       315                       320
Ala Arg Lys Gly Lys Tyr Gly Ile Tyr Thr Lys Val Thr Ala Phe Leu
                325                       330                       335
Lys Trp Ile Asp Arg Ser Met Lys Thr Arg Gly Leu Pro Lys Ala Lys
            340                       345                       350
Ser His Ala Pro Glu Val Ile Thr Ser Ser Pro Leu Lys
            355                       360                       365

FIG. 1

SEQ ID NO: 2:

```
Ala Asn Ser Phe Leu Phe Trp Asn Lys Tyr Lys Asp Gly Asp Gln Cys
1               5                   10                  15
Glu Thr Ser Pro Cys Gln Asn Gln Gly Lys Cys Lys Asp Gly Leu Gly
                20                  25                  30
Glu Tyr Thr Cys Thr Cys Leu Glu Gly Phe Glu Gly Lys Asn Cys Glu
            35                  40                  45
Leu Phe Thr Arg Lys Leu Cys Ser Leu Asp Asn Gly Asp Cys Asp Gln
        50                  55                  60
Phe Cys His Glu Glu Gln Asn Ser Val Val Cys Ser Cys Ala Arg Gly
65                  70                  75                  80
Tyr Thr Leu Ala Asp Asn Gly Lys Ala Cys Ile Pro Thr Gly Pro Tyr
                85                  90                  95
Pro Cys Gly Lys Gln Thr Leu Glu Arg Ile Val Gly Gly Gln Glu Cys
                100                 105                 110
Lys Asp Gly Glu Cys Pro Trp Gln Ala Leu Leu Ile Asn Glu Glu Asn
            115                 120                 125
Glu Gly Phe Cys Gly Gly Thr Ile Leu Ser Glu Phe Tyr Ile Leu Thr
        130                 135                 140
Ala Ala His Cys Leu Tyr Gln Ala Lys Arg Phe Lys Val Arg Val Gly
145                 150                 155                 160
Asp Arg Asn Thr Glu Gln Glu Glu Gly Gly Glu Ala Val His Glu Val
                165                 170                 175
Glu Val Val Ile Lys His Asn Arg Phe Thr Lys Glu Thr Tyr Asp Phe
            180                 185                 190
Asp Ile Ala Val Leu Arg Leu Lys Thr Pro Ile Thr Phe Arg Met Asn
        195                 200                 205
Val Ala Pro Ala Cys Leu Pro Glu Arg Asp Trp Ala Glu Ser Thr Leu
        210                 215                 220
Met Thr Gln Lys Thr Gly Ile Val Ser Gly Phe Gly Arg Thr His Glu
225                 230                 235                 240
Lys Gly Arg Gln Ser Thr Arg Leu Lys Met Leu Glu Val Pro Tyr Val
                245                 250                 255
Asp Arg Asn Ser Cys Lys Leu Ser Ser Ser Phe Ile Ile Thr Gln Asn
                260                 265                 270
Met Phe Cys Ala Gly Tyr Asp Thr Lys Gln Glu Asp Ala Cys Gln Gly
            275                 280                 285
Asp Ala Gly Gly Pro His Val Thr Arg Phe Lys Asp Thr Tyr Phe Val
        290                 295                 300
Thr Gly Ile Val Ser Trp Gly Glu Gly Cys Ala Arg Lys Gly Lys Tyr
305                 310                 315                 320
Gly Ile Tyr Thr Lys Val Thr Ala Phe Leu Lys Trp Ile Asp Arg Ser
                325                 330                 335
Met Lys Thr Arg Gly Leu Pro Lys Ala Lys Ser His Ala Pro Glu Val
                340                 345                 350
Ile Thr Ser Ser Pro Leu Lys
                355
```

FIG. 2

COMPOUNDS AND METHODS FOR PURIFICATION OF SERINE PROTEASES

CROSS REFERENCE TO RELATED APPLICATIONS

This application is a continuation of U.S. application Ser. No. 14/142,655, filed Dec. 27, 2013, now abandoned, which is a continuation-in-part of U.S. application Ser. No. 13/830,372, filed Mar. 14, 2013, now U.S. Pat. No. 9,200,268, which claims the benefit under 35 U.S.C. §119(e) of U.S. Application No. 61/746,544, filed Dec. 27, 2012, all of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on May 17, 2013, is named 070545-5401_SL.txt and is 10,327 bytes in size.

FIELD

This disclosure relates to compounds, compositions, methods and kits for the purification of serine proteases, such as factor Xa derivatives.

BACKGROUND

Anticoagulants serve a need in the marketplace in treatment or prevention of undesired thrombosis in patients with a tendency to form blood clots, such as, for example, those patients having clotting disorders, confined to periods of immobility or undergoing medical surgeries. One of the major limitations of anticoagulant therapy, however, is the bleeding risk associated with treatment, and limitations on the ability to rapidly reverse the anticoagulant activity in case of overdosing or if an urgent surgical procedure is required. Thus, specific and effective antidotes to all forms of anticoagulant therapy are highly desirable. For safety considerations, it is also advantageous to have an anticoagulant-antidote pair in the development of new anticoagulant drugs.

Previously reported modified derivatives of factor Xa (fXa), such as those described in U.S. Pat. Nos. 8,153,390 and 8,268,783 (which is herein incorporated by reference in its entirety), including r-Antidote, are useful as antidotes to anticoagulants targeting fXa. The modified derivatives of fXa bind to and/or substantially neutralize the anticoagulant. Certain modifications introduced to fXa, however, pose several challenges for purification since routine methods for purification of clotting factors cannot be used for r-Antidote.

SUMMARY

Disclosed herein are compounds, compositions, methods and kits for purifying a serine protease. In one aspect, the serine protease comprises a modified derivative of a fXa protein. In some embodiments, the modified fXa protein comprises the amino acid sequence of SEQ ID NO: 2 or a polypeptide having at least about 80% sequence identity to SEQ ID NO: 2.

The compounds described herein have binding affinity with the serine protease to be purified (e.g., the compounds are ligands of the serine protease), and can be covalently attached to an activated solid support, such as a resin. The solid support having a small molecule compound bound thereto is referred to as an affinity solid support. In some embodiments, the affinity solid support is packed into a column, which is referred to as an affinity column. A solution comprising the serine protease to be purified is loaded to the affinity column. The serine protease to be purified is retained in the column through binding activity with the compound. Impurities in the solution are washed with a washing buffer so that the proteins left on the column are mostly the serine protease having binding affinity with the compound. The serine protease can then be eluted by an elution buffer comprising a competitive agent, which can disrupt the binding of the serine protease with the compound and release the serine protease from the affinity column, so that the purified serine protease is eluted from the column with the elution buffer.

In some embodiments, compounds used to purify the proteins are analogues of betrixaban or a salt thereof. Betrixaban is described in U.S. Pat. No. 6,376,515, which is incorporated herein by reference in its entirety, and is of the formula:

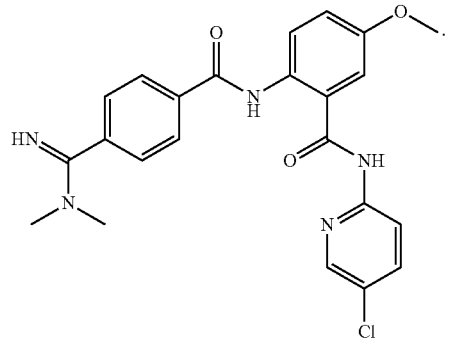 [SMILES: COc1ccc(NC(=O)c2ccc(C(=N)N(C)C)cc2)c(C(=O)Nc2ccc(Cl)cn2)c1]

Accordingly, in one aspect, provided is a compound of Formula I:

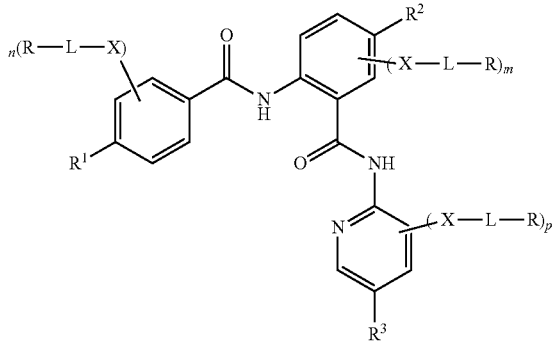

or a salt thereof,
wherein:
$R^1$ is —$CF_3$, —$SO_2CH_3$, —X-L-R,

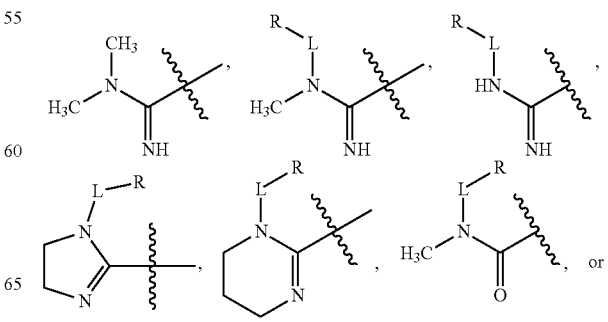

-continued

[structure: R-L-NH-C(O)- fragment]

R² is —OCH₃, chloro, or X-L-R;
R³ is hydrogen or chloro;
X is a covalent bond, O, S, SO₂, C(O)NH, NHC(O) or NH;
L-R is -L¹-R,

[structures: amide linker -C(O)NH-L¹-R; amine linker -NH-L²-R; ether linker -O-L³-R]

L¹-R is

[structures: -(CH₂)_q-R or -(CH₂CH₂O)_r-R]

L²-R is H,

[structures: -C(O)-(CH₂)_s-R or -C(O)-(CH₂CH₂O)_t-R]

L³-R is

[structures: -(CH₂)_q-R or -(CH₂CH₂O)_r-R]

R is NH₂ or CO₂H;
q is 1, 2, 3, 4, 5, 6 or 7;
r is 1, 2, 3, 4, 5, 6 or 7;
s is 1, 2, 3, 4, 5, 6 or 7;
t is 1, 2, 3, 4, 5, 6 or 7;
n, m, and p are either 0 or 1, with the provisos that
(1) when R¹ is

[structure: (CH₃)₂N-C(=NH)-]

—CF₃ or —SO₂CH₃, and R² is —OCH₃ or chloro, then one of n, m, and p must be 1, and the others of n, m, and p must be zero; and (2) when R¹ is other than

[structure: (CH₃)₂N-C(=NH)-]

—CF₃ or —SO₂CH₃, or R² is X-L-R, then all of n, m, and p must be zero.

In some embodiments, the compound of Formula I is a compound of Formula I-A:

I-A

[structure of Formula I-A with substituents n(H₂N—L—X), R¹, R², (X—L—NH₂)_m, and pyridine with (X—L—NH₂)_p and R³]

In some embodiments, the compound of Formula I is a compound of Formula I-B:

I-B

[structure of Formula I-B with substituents n(HO₂C—L—X), R¹, R², (X—L—CO₂H)_m, and pyridine with (X—L—CO₂H)_p and R³]

In another aspect, provided is an affinity solid support comprising a compound of Formula I bound to a solid support via a linker, which affinity solid support is of Formula II:

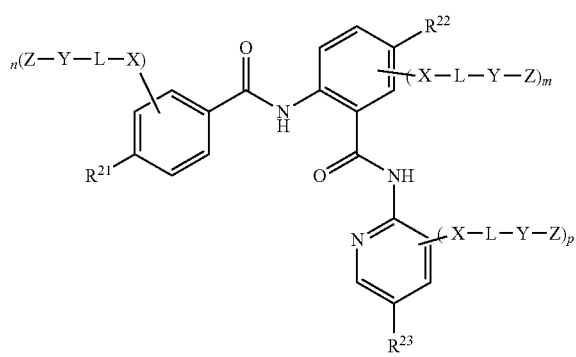

or a salt thereof,
wherein:
$R^{21}$ is —$CF_3$, —$SO_2CH_3$, —X-L-Y—Z,

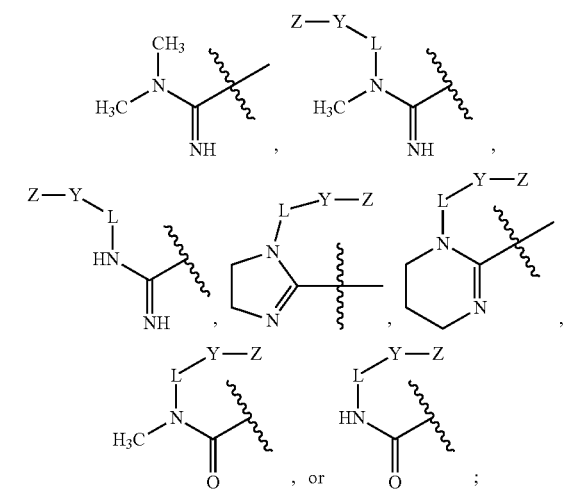

$R^{22}$ is —$OCH_3$, chloro, or —X-L-Y—Z;
$R^{23}$ is hydrogen or chloro;
X is a covalent bond, O, S, $SO_2$, C(O)NH, NHC(O) or NH;
L-Y—Z is -$L^1$-Y—Z,

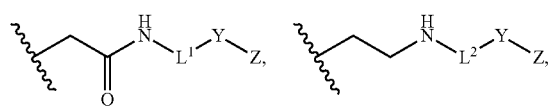

$L^1$-Y—Z is

$L^2$-Y—Z is

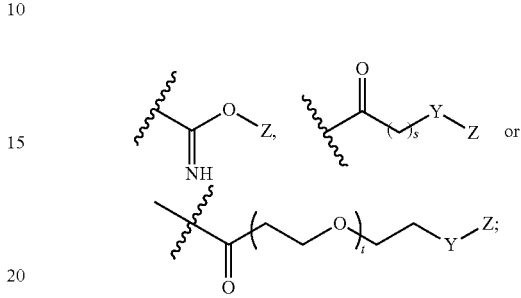

$L^3$-Y—Z is

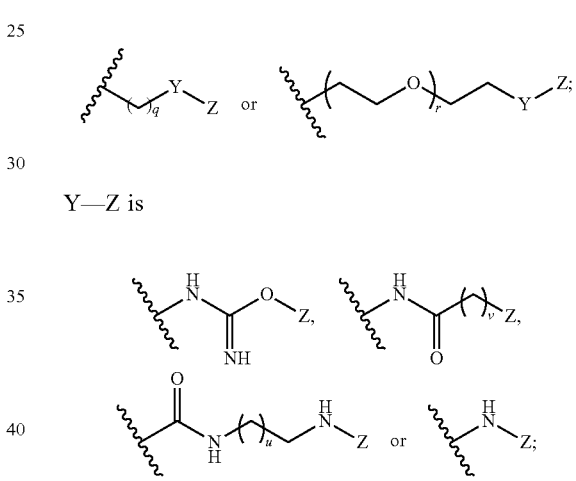

Y—Z is

Z is a solid support;
q is 1, 2, 3, 4, 5, 6 or 7;
r is 1, 2, 3, 4, 5, 6 or 7;
s is 1, 2, 3, 4, 5, 6 or 7;
t is 1, 2, 3, 4, 5, 6 or 7;
v is 1, 2, 3, 4, 5, 6 or 7;
u is 1, 2, 3, 4, 5, 6 or 7;
w is 1, 2 or 3;
n, m, and p are either 0 or 1, with the provisos that
(1) when $R^{21}$ is

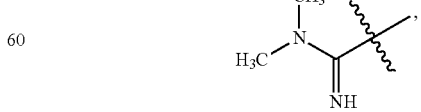

—$CF_3$ or —$SO_2CH_3$, and $R^{22}$ is —$OCH_3$ or chloro, then one of n, m, and p must be 1, and the others of n, m, and p must be zero; and (2) when $R^{21}$ is other than

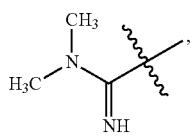

—$CF_3$ or —$SO_2CH_3$, or $R^{22}$ is X-L-Y—Z, then all of n, m, and p must be zero.

In another aspect, provided is a method of preparing an affinity solid support of Formula II comprising contacting a compound of Formula I with an activated solid support capable of forming a covalent bond with the compound of Formula I, wherein the affinity solid support of Formula II, the compound of Formula I and activated solid support are as defined herein.

In another aspect, provided is a method for purifying a serine protease comprising
(1) adding a first composition comprising the serine protease to an affinity solid support of Formula II to form a second composition comprising the serine protease and the affinity solid support of Formula II, and (2) eluting the serine protease from the second composition with an elution buffer comprising a competitive agent,
wherein the affinity solid support of Formula II is as defined herein.

In another aspect, provided is a purified serine protease, which is purified by a method comprising
(1) adding a first composition comprising the serine protease to an affinity solid support of Formula II to form a second composition comprising the serine protease and the affinity solid support of Formula II, and
(2) eluting the serine protease from the second composition with an elution buffer comprising a competitive agent,
wherein the affinity solid support of Formula II is as defined herein.

In some embodiments, the competitive agent is arginine and/or benzamidine, or a salt, such as a pharmaceutically acceptable salt, thereof.

In still another aspect, provided is a kit for purifying a serine protease comprising
(1) an affinity solid support of Formula II, and
(2) an elution buffer comprising a competitive agent,
wherein the affinity solid support of Formula II is as defined herein.

In still another aspect, provided is a kit for purifying a serine protease comprising
(1) a compound of Formula I and an activated solid support capable of forming a covalent bond with the compound of Formula I, and
(2) an elution buffer comprising a competitive agent,
wherein the compound of Formula I and the activated solid support are as defined herein.

In some embodiments, the competitive agent is arginine and/or benzamidine, a pharmaceutically acceptable salt thereof.

A further aspect relates to a purified serine protease produced by the methods described herein.

These and other aspects are described further in the text that follows.

BRIEF DESCRIPTION OF THE FIGURES

FIG. 1 shows SEQ ID NO: 1, a fXa derivative (also referred to as r-Antidote precursor) with the linker, -RKRRKR- (SEQ ID NO: 3) at amino acids 106-111;

FIG. 2 shows SEQ ID NO: 2, a fXa derivative (also referred to as r-Antidote) with the linker removed from the r-Antidote precursor;

DETAILED DESCRIPTION

Definitions

Figure 3:
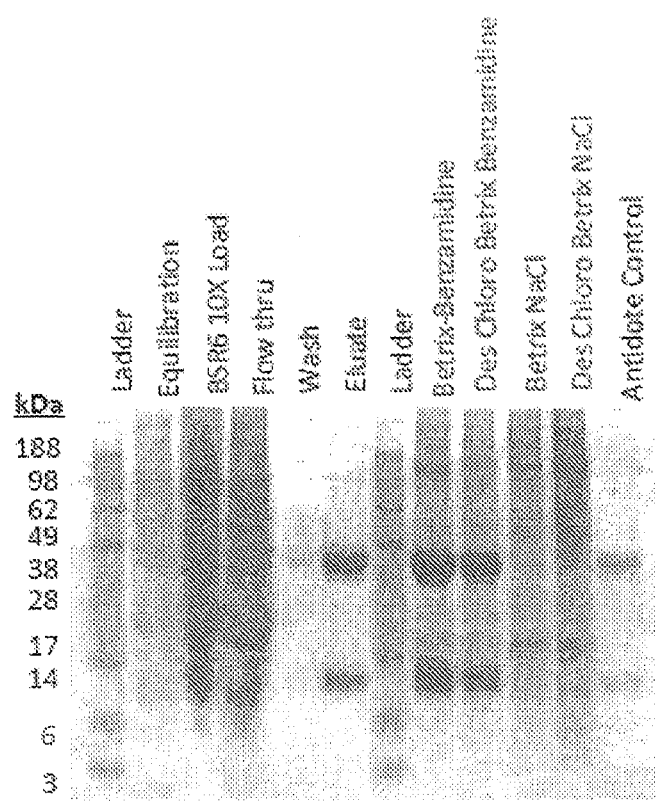
FIG. 3 shows the elution profile with benzamidine as described in Example 10.
Figure 4:
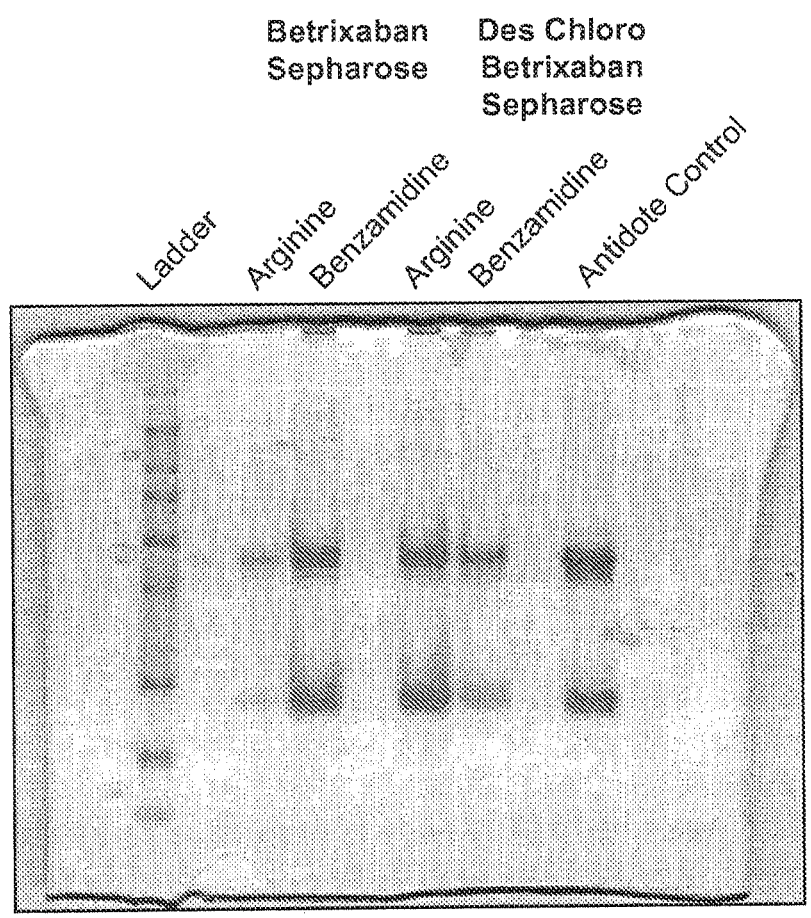
FIG. 4 shows the elution profile with arginine as described in Example 10.

The practice of the present disclosure will employ, unless otherwise indicated, conventional techniques of tissue culture, immunology, molecular biology, microbiology, cell biology and recombinant DNA, which are within the skill of the art. See, e.g., Sambrook et al., (1989) Molecular Cloning: A Laboratory Manual, 2nd edition; Ausubel et al., eds. (1987) Current Protocols In Molecular Biology; MacPherson, B. D. Hames and G. R. Taylor eds., (1995) PCR 2: A Practical Approach; Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

As used herein, the term "about" generally means the stated value plus or minus a range of 10% or 5% of that value.

As used in the specification and claims, the singular form "a," "an" and "the" include plural references unless the context clearly dictates otherwise.

The term "solid support" intends solid phase supports include silica gels, resins, derivatized plastic films, glass beads, glass slides, flasks, tissue culture flasks, cotton, plastic beads, alumina gels, pellets, cellulose beads, poreglass beads, grafted co-poly beads and polyacrylamide beads. More specific examples include polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany) or polydimethylacrylamide resin (obtained from Milligen/Biosearch, Calif.). Solid supports also include microchips and grids. The surface of the grids may be composed of a wide variety of material including glass, plastic, silicon, gold, gelatin or nylon. Lockhart (2000) Nature, 405:827-836; Srinivas (2001) Clin. Chem., 47:1901-1911. In some embodiments, the solid support is cross-linked agarose. In some embodiments, the solid support is a cross-linked, beaded-form of a polysaccharide polymer material extracted from seaweed. In some embodiments, the solid support is Sepharose™ resin, available from GE Healthcare. In other embodiments, the solid support is Capto™ resin, available from GE Healthcare.

The term "activated solid support" refers to a solid support functionalized with a functional group that can form a covalent bond with a compound of Formula I under suitable reaction conditions. In some embodiments, the activated solid support is an agarose bead functionalized with a N≡C group, e.g., CNBr-activated Sepharose™ resin. In some embodiments, the activated solid support is an agarose bead functionalized with free amino groups, e.g., EAH Sepharose™ resin. This is referred to as "aminofunctionalized agarose." In some embodiments, the activated solid support is an agarose bead functionalized with a (N-hydroxysuccinimide group, e.g., NHS-activated Sepharose™ resin. In some embodiments, Capto™ resin is activated similarly.

The term "affinity solid support" refers to a solid support having a compound of Formula I bound thereto, wherein the compound of Formula I exhibits binding affinity towards a serine protease to be purified. The term "affinity resin" refers to an affinity solid support wherein the solid support is a resin. The term "affinity column" refers to a column comprising the affinity solid support. In some embodiments, the compound of Formula I is covalently bound to the solid support.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The term "isolated" or "recombinant" as used herein with respect to nucleic acids, such as DNA or RNA, refers to molecules separated from other DNAs or RNAs. The term "isolated" is also used herein to refer to polynucleotides, polypeptides and proteins that are isolated from other cellular proteins and is meant to encompass both purified and recombinant polypeptides. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

The term "biological equivalent of" a protein, peptide or polynucleotide refers to one that has at least about 80% homology or identity and alternatively, at least about 85%, or alternatively at least about 90%, or alternatively at least about 95%, or alternatively 98% percent homology or identity, and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, 95%, 97%, 98%, or 99%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares, for example, less than 40% identity, or alternatively less than 25% identity, with one of the sequences of the present disclosure.

The term "fraction" when used in the context of protein isolation, refers to a collection of material separated based on a specific property. The specific property may include, by way of non-limiting example, size, mass, isoelectric point, charge, and the like.

"Factor Xa" or "fXa" or "fXa protein" refers to a serine protease in the blood coagulation pathway, which is produced from the inactive factor X (fX). Factor Xa is activated by either factor IXa with its cofactor, factor VIIIa, in a complex known as intrinsic Xase, or factor VIIa with its cofactor, tissue factor, in a complex known as extrinsic Xase. fXa forms a membrane-bound prothrombinase complex with factor Va and is the active component in the prothrombinase complex that catalyzes the conversion of prothrombin to thrombin. Thrombin is the enzyme that catalyzes the conversion of fibrinogen to fibrin, which ultimately leads to blood clot formation.

As used herein, a "fXa derivative" refers to a modified fXa protein that does not compete with fXa in assembling into the prothrombinase complex and has reduced or no procoagulant activity, and yet binds and/or substantially neutralizes an anticoagulant, such as a fXa inhibitor. An example of a fXa derivative is provided herein as SEQ ID NO: 2 (FIG. 2) or a biological equivalent thereof.

"r-Antidote precursor" refers to a fXa derivative represented by SEQ ID NO: 1, which contains three mutations relative to human fXa. The first mutation is a deletion in the Gla-domain of the wild-type fX protein at position 6-39. The second mutation is replacing the activation peptide sequence 143-194 amino acids with -RKR-. This produces a -RKRRKR- (SEQ ID NO: 3) linker connecting the light chain and the heavy chain. Upon secretion, this linker is cleaved in CHO resulting in a cleaved two-chain polypeptide. The term "cleaved two-chain polypeptide" refers to a polypeptide of SEQ ID NO: 2, or a polypeptide having 80% identity to SEQ ID NO: 2, having two-chains and being linked together by a disulfide bond. The N-terminal chain consist of amino acids 1-105 of SEQ ID NO: 2 and the C-terminal chain consists of amino acids 106-359 of SEQ ID NO: 2. Optionally, the LC chain may contain 1, 2, 3, 4, 5 or 6 amino acid residues of the linker. Such additional residues result from the incomplete removal of the linker polypeptide. The third mutation is mutation of active site residue S379 to an Ala residue (based on secreted human fX sequence). This amino acid substitution corresponds to amino acid 296 and 290 of SEQ ID NOS: 1 and 2, respectively.

The term "r-Antidote" may refer to the polypeptide (SEQ ID NO: 1) before removal of the linker (SEQ ID NO: 3) or after removal of the linker (SEQ ID NO: 3). The r-Antidote with the linker removed has two forms: alpha form (SEQ ID NO: 2), and beta form (SEQ ID NO. 4), which lacks the beta-peptide (GLPKAKSHAPEVITSSPLK, SEQ ID NO: 5) at the c-terminus of the heavy chain. These polypeptides are described in Tables 1-3 below.

TABLE 1

SEQ ID NO. 1-Polypeptide sequence of the r-antidote precursor, prior to removal of the -RKRRKR- (SEQ ID NO. 3) linker Light Chain

```
  1 ANSFL                                       F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker

```
RKRRKR
```

Heavy Chain

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 2

Sequence ID NO. 2-Polypeptide sequence of the r-antidote, the alpha form

Light Chain

```
  1 ANSFL                                       F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 3

SEQ ID NO. 4-Polypeptide sequence of the r-antidote, the beta form, which lacks the beta-peptide (GLPKAKSHAPEVITSSPLK, SEQ ID NO. 5) at the c-terminus of the heavy chain

Light Chain

```
  1 ANSFL                              F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain

```
181             IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTR
```

The term "competitive agent" is a molecule that can aid in the elution of the serine protease from the affinity solid support of Formula II either by disruption of a charge-charge interaction between the affinity solid support of Formula II and the serine protease or by competing with the affinity solid support of Formula II for binding to the serine protease. Non-limiting examples of competitive agents include arginine and benzamidine.

The term "chaotropic agent" intends a substance which disrupts the structure of, and denatures, macromolecules such as proteins and nucleic acids. Chaotropic agents include, for example, butanol, ethanol, guanidinium chloride, lithium perchlorate, magnesium chloride, phenol, propanol, sodium dodecyl sulfate, thiourea, and urea.

The term "salt" refers to an ionic compounds that result from the neutralization reaction of an acid and a base, and is composed of at least one cations (positively charged ion) and at least one anion (negative ion). In some embodiments, a salt is electrically neutral (without a net charge). The term "pharmaceutically acceptable salts" is meant to include salts of the compounds which are prepared with relatively non-toxic acids or bases, depending on the particular substituents found on the compounds described herein. Pharmaceutically acceptable salts derived from inorganic bases include aluminum, ammonium, calcium, copper, ferric, ferrous, lithium, magnesium, manganic, manganous, potassium, sodium, and zinc salts, and the like. Pharmaceutically acceptable salts derived from organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Acids that can form pharmaceutically acceptable salts include inorganic acids such as hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, and relatively nontoxic organic acids such as acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", *Journal of Pharmaceutical Science*, 1977, 66, 1-19).

Compounds

In one aspect, provided is a compound of Formula I:

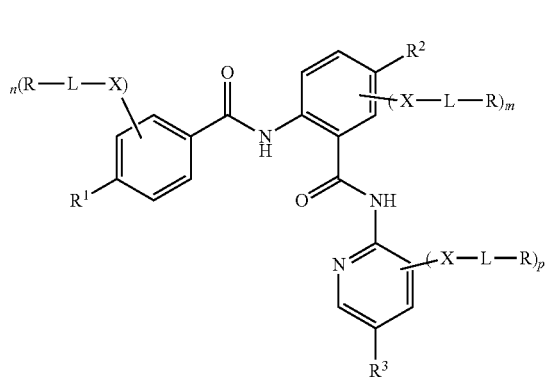

or a salt thereof, wherein:

R$^1$ is —CF$_3$, —SO$_2$CH$_3$, —X-L-R,

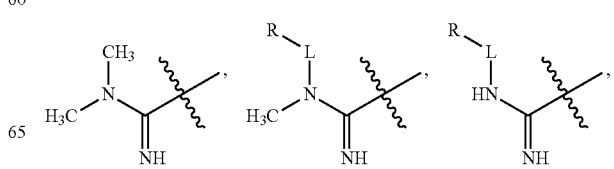

-continued

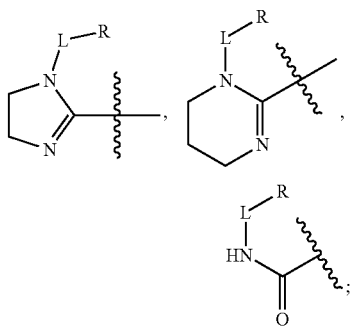

$R^2$ is —OCH$_3$, chloro, or X-L-R;

$R^3$ is hydrogen or chloro;

X is a covalent bond, O, S, SO$_2$, C(O)NH, NHC(O) or NH;

L-R is -L$^1$-R,

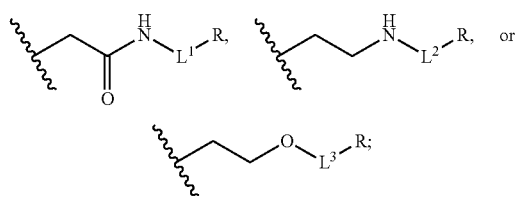

L$^1$-R is

L$^2$-R is H,

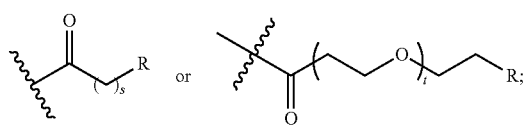

L$^3$-R is

R is NH$_2$ or CO$_2$H;

q is 1, 2, 3, 4, 5, 6 or 7;

r is 1, 2, 3, 4, 5, 6 or 7;

s is 1, 2, 3, 4, 5, 6 or 7;

t is 1, 2, 3, 4, 5, 6 or 7;

n, m, and p are either 0 or 1, with the provisos that (1) when $R^1$ is

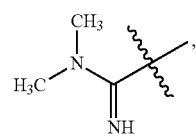

—CF$_3$ or —SO$_2$CH$_3$, and $R^2$ is —OCH$_3$ or chloro, then one of n, m, and p must be 1, and the others of n, m, and p must be zero; and (2) when $R^1$ is other than

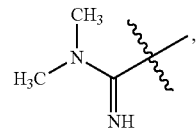

—CF$_3$ or —SO$_2$CH$_3$, or $R^2$ is X-L-R, then all of n, m, and p must be zero.

In some embodiments, the compound of Formula I is a compound of Formula I-A:

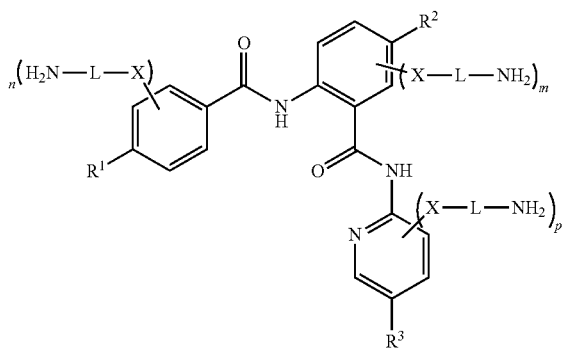

I-A i.e., wherein R is NH$_2$.

In some embodiments, the compound of Formula I is a compound of Formula I-B:

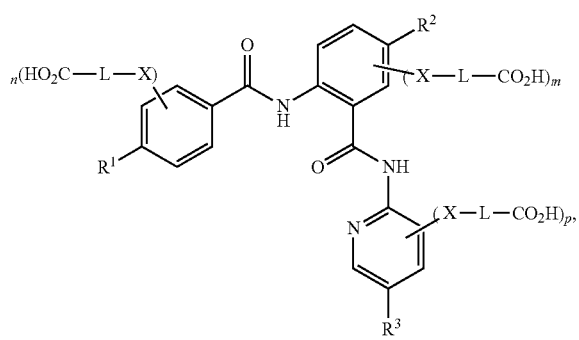

I-B i.e., wherein R is CO$_2$H.

In some embodiments, the compound of Formula I is a compound of Formula I-C:

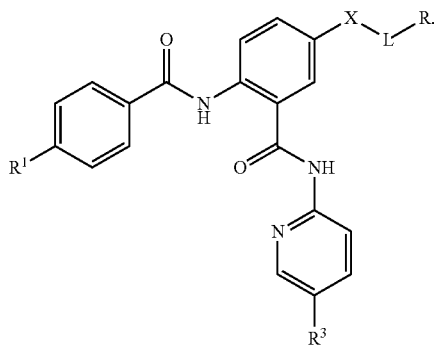

I-C

In some embodiments, $R^1$ is

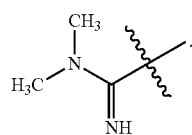 [SMILES: *C(=N)N(C)C]

In some embodiments, $R^3$ is hydrogen. In some embodiments, $R^3$ is chloro.

In some embodiments, $R^2$ is —$OCH_3$. In some embodiments, $R^2$ is X-L-R.

In some embodiments, X is O. In some embodiments, X is S. In some embodiments, X is $SO_2$. In some embodiments, X is NH. In some embodiments, X is C(O)NH. In some embodiments, X is NHC(O). In some embodiments, X is a covalent bond.

In some embodiments, L-R is -$L^1$-R. In some embodiments, L-R is

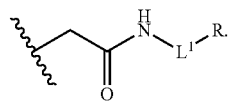

In some embodiments, $L^1$-R is

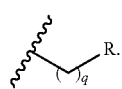

In some embodiments, L-R is

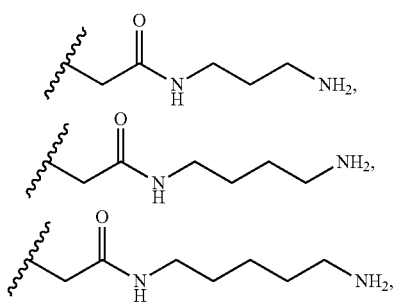

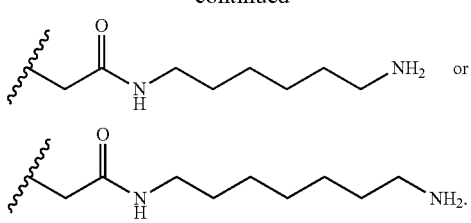

In some embodiments, L-R is

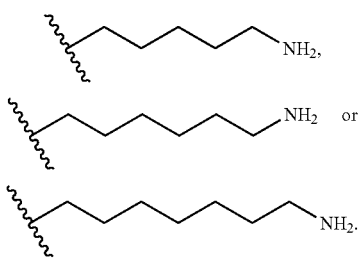

In some embodiments, —X-L-R is

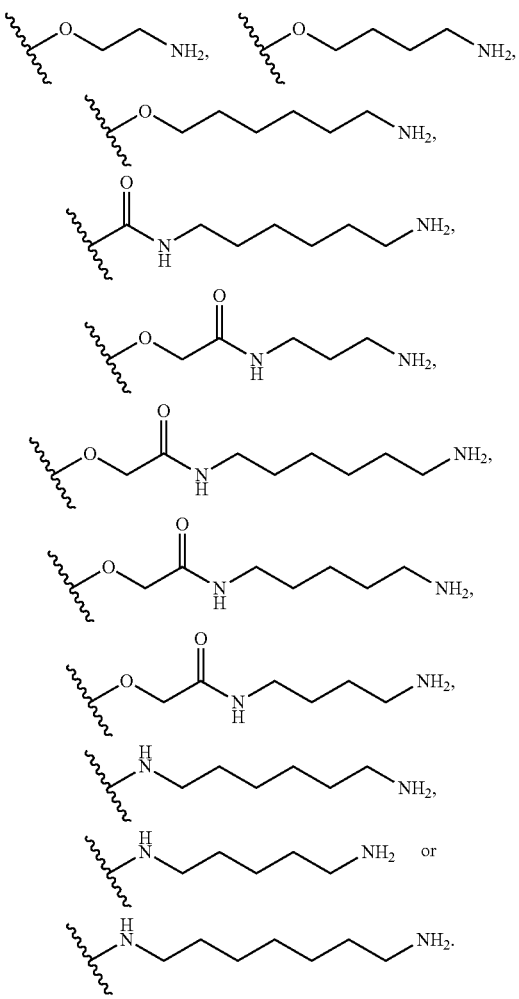

In some embodiments, —X-L-R is

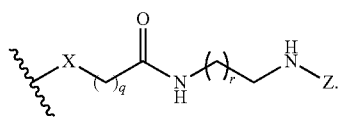

In some embodiments, —X-L-R is

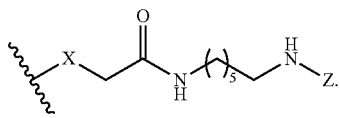

In some embodiments, q is at least 3. In some embodiments, r is at least 3. In some embodiments, s is at least 3. In some embodiments, t is at least 3.

In some embodiments, the compound of Formula I inhibits fXa with an $IC_{50}$ of from about 100 nM to about 1 μM, from about 150 nM to about 700 nM, or from about 200 nM to about 500 nM.

In some embodiments, the compound of Formula I is selected from

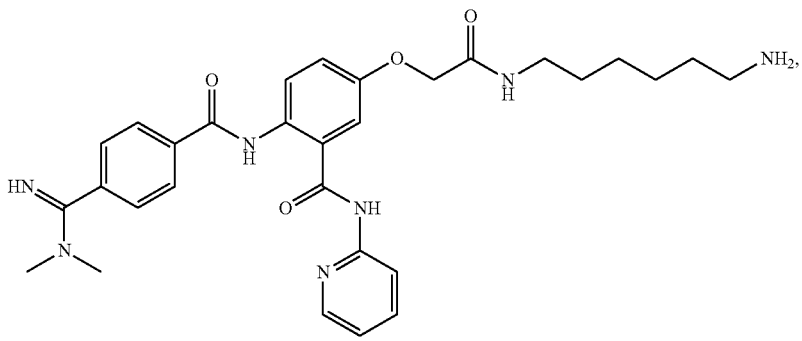

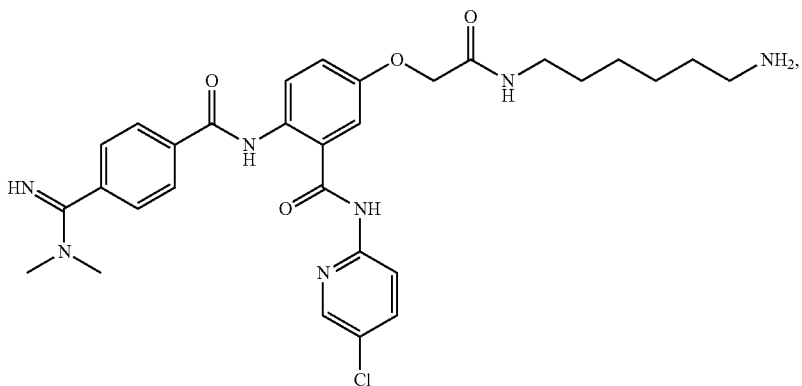

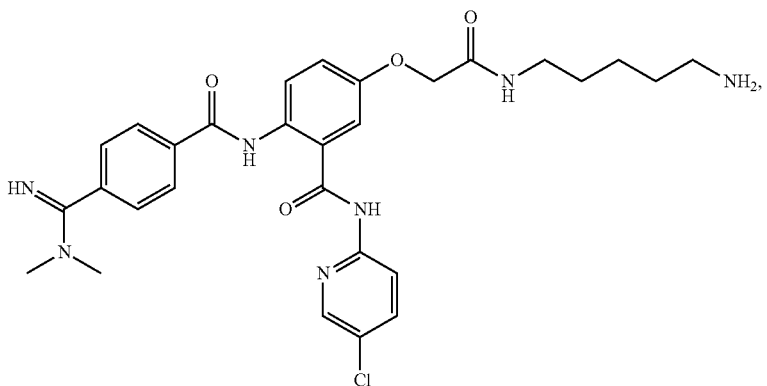

-continued
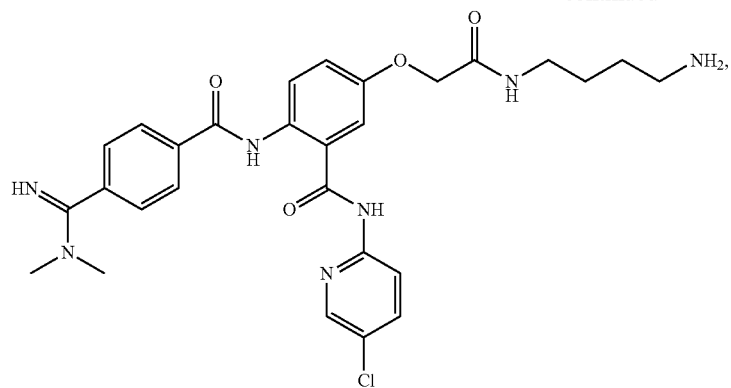
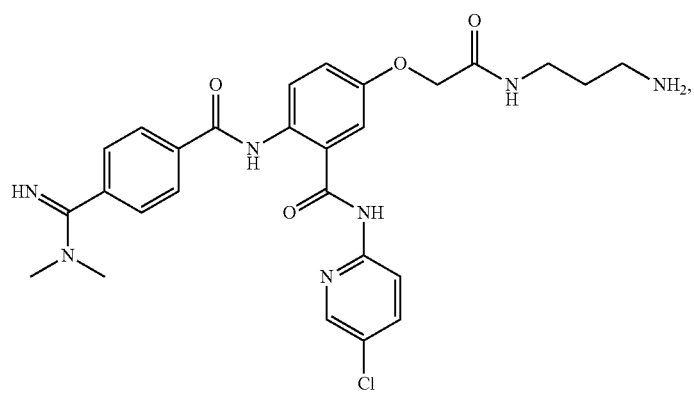
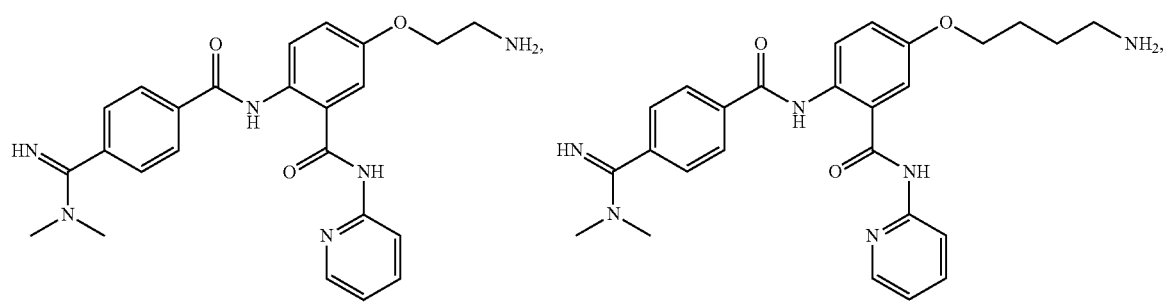
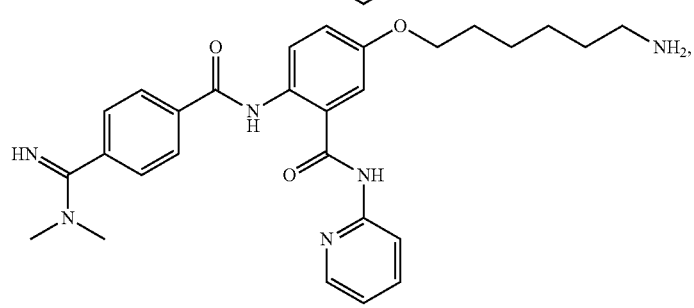
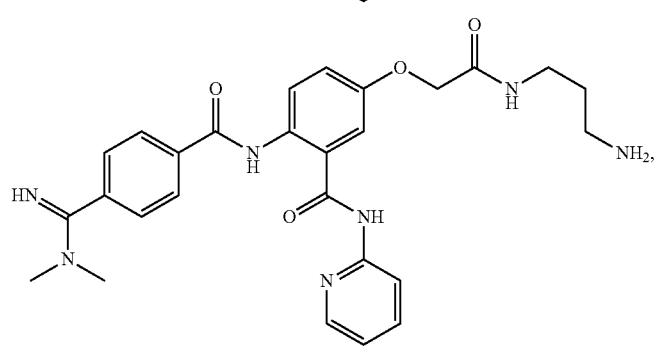

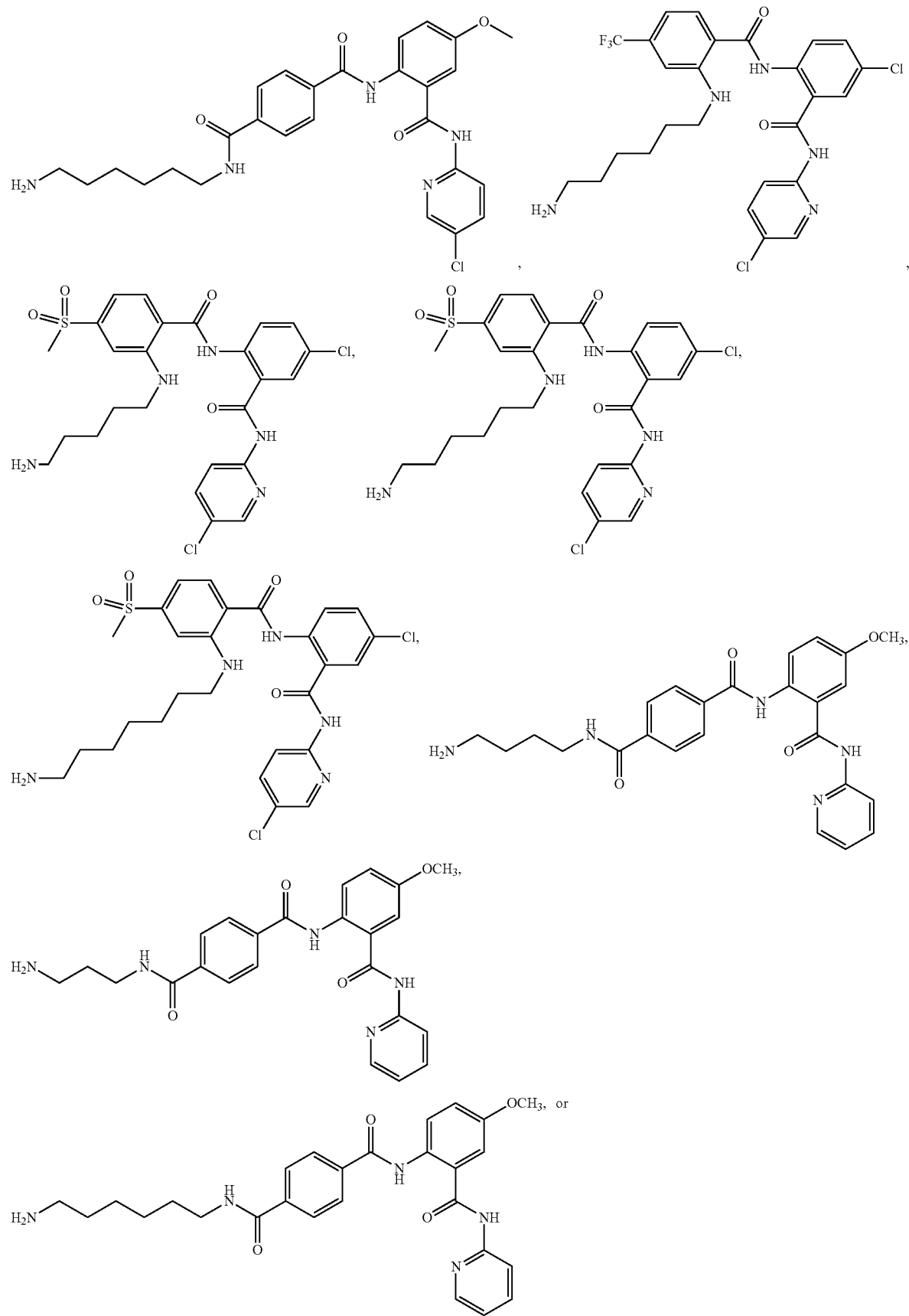

or a salt thereof.

Affinity Solid Supports

In another aspect, provided is an affinity solid support of Formula II:

or a salt thereof,
wherein:

$R^{21}$ is —CF₃, —SO₂CH₃, —X-L-Y—Z,

[structures shown]

$R^{22}$ is —OCH₃, chloro, or X-L-Y—Z;
$R^{23}$ is hydrogen or chloro;
X is a covalent bond, O, S, SO₂, C(O)NH, NHC(O) or NH;
L-Y—Z is -L¹-Y—Z, $L^1$-Y—Z is $L^2$-Y—Z is $L^3$-Y—Z is Y—Z is Z is a solid support;
q is 1, 2, 3, 4, 5, 6 or 7;

r is 1, 2, 3, 4, 5, 6 or 7;
s is 1, 2, 3, 4, 5, 6 or 7;
t is 1, 2, 3, 4, 5, 6 or 7;
v is 1, 2, 3, 4, 5, 6 or 7;
u is 1, 2, 3, 4, 5, 6 or 7;
w is 1, 2 or 3;
n, m, and p are either 0 or 1, with the provisos that
(1) when $R^{21}$ is

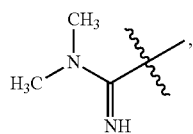

—$CF_3$ or —$SO_2CH_3$, and $R^{22}$ is —$OCH_3$ or chloro, then one of n, m, and p must be 1, and the others of n, m, and p must be zero; and (2) when $R^{21}$ is other than

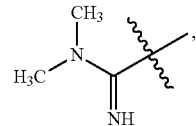

—$CF_3$ or —$SO_2CH_3$, or $R^{22}$ is X-L-Y—Z, then all of n, m, and p must be zero.

In some embodiments, the affinity solid support of Formula II is an affinity solid support of Formula II-A

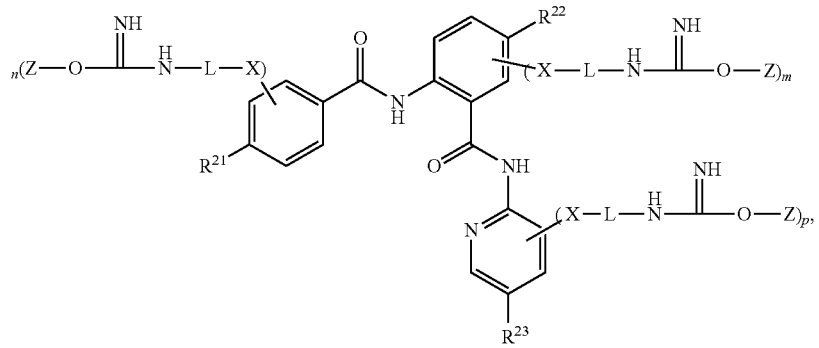

i.e., wherein Y—Z is

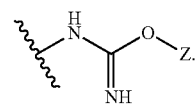

In some embodiments, the affinity solid support of Formula II is of Formula II-B

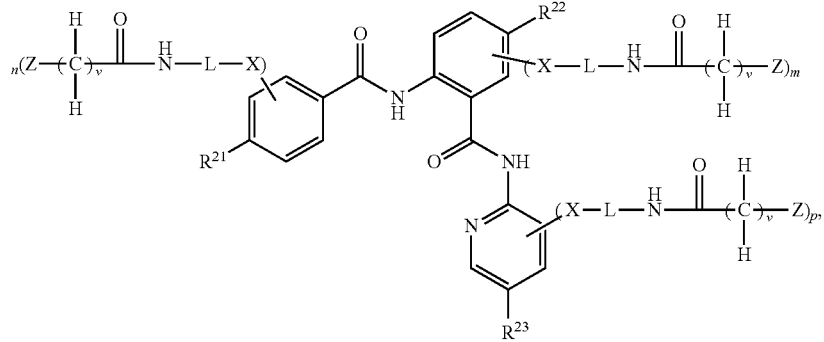

i.e., wherein Y—Z is

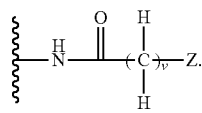

In some embodiments, the affinity solid support of Formula II is of Formula II-C

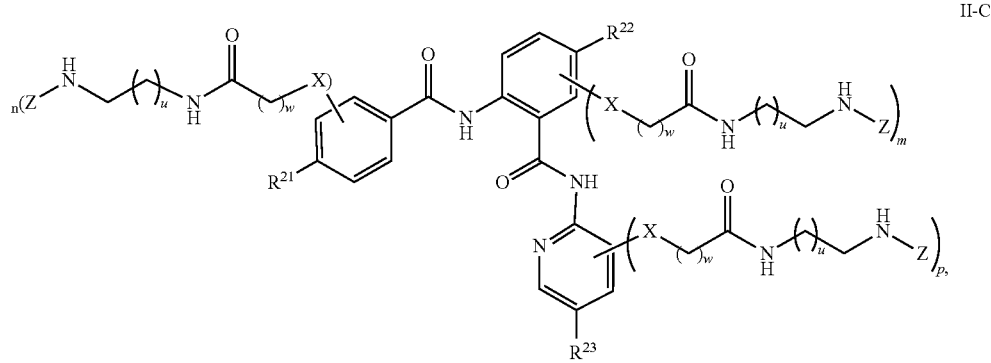

II-C i.e., wherein L-Y—Z is

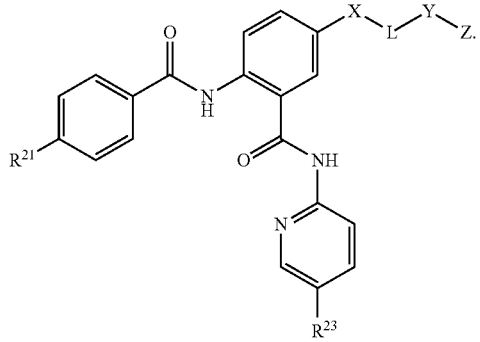

u is 1, 2, 3, 4, 5, 6 or 7, and w is 1, 2 or 3.

In some embodiments, u is 4 or 5, and w is 1.

In some embodiments, the affinity solid support is of Formula II-D:

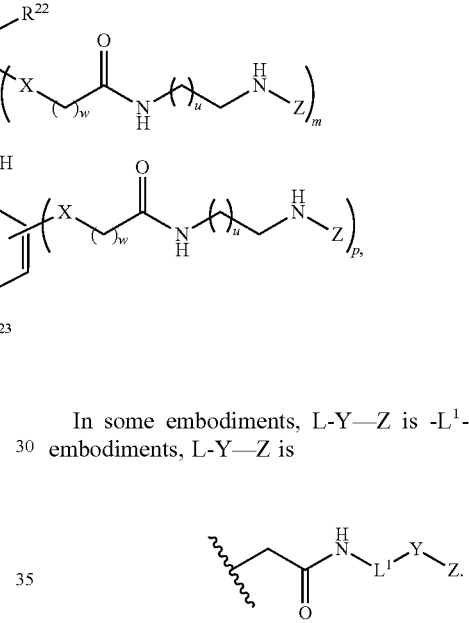

II-D

In some embodiments, $R^{21}$ is

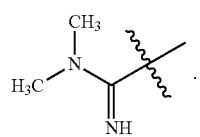

In some embodiments, $R^{22}$ is —OCH$_3$. In some embodiments, $R^{22}$ is X-L-Y—Z.

In some embodiments, $R^{23}$ is hydrogen. In some embodiments, $R^{23}$ is chloro.

In some embodiments, X is O. In some embodiments, X is S. In some embodiments, X is SO$_2$. In some embodiments, X is NH. In some embodiments, X is C(O)NH. In some embodiments, X is NHC(O). In some embodiments, X is covalent bond.

In some embodiments, L-Y—Z is -L$^1$-Y—Z. In some embodiments, L-Y—Z is

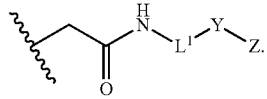

In some embodiments, L$^1$-Y—Z is

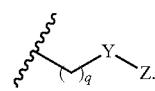

In some embodiments, L-Y—Z is

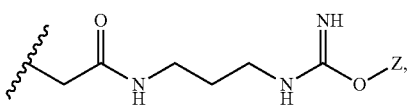

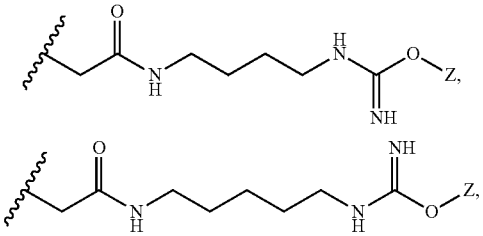

-continued
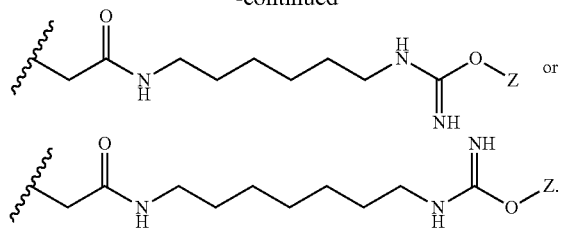
In some embodiments, L-Y—Z or L¹-Y—Z is
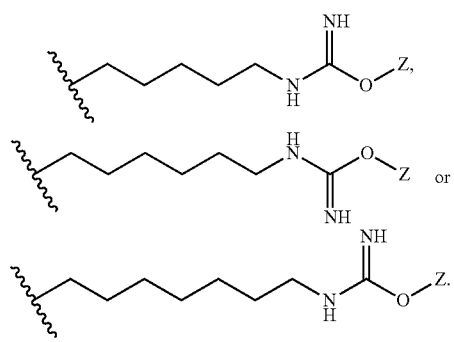
In some embodiments, L-Y—Z or L¹-Y—Z is
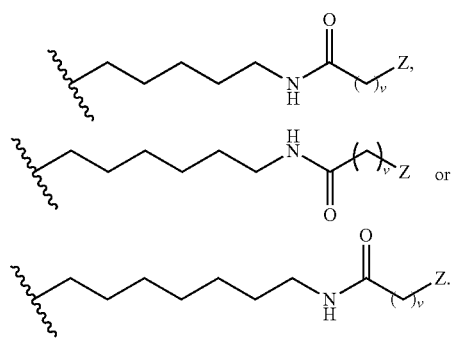
In some embodiments, L-Y—Z or L¹-Y—Z is
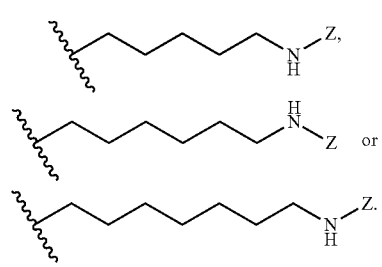
In some embodiments, —X-L-Y—Z is
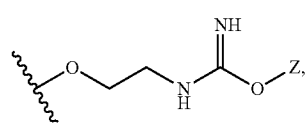
-continued
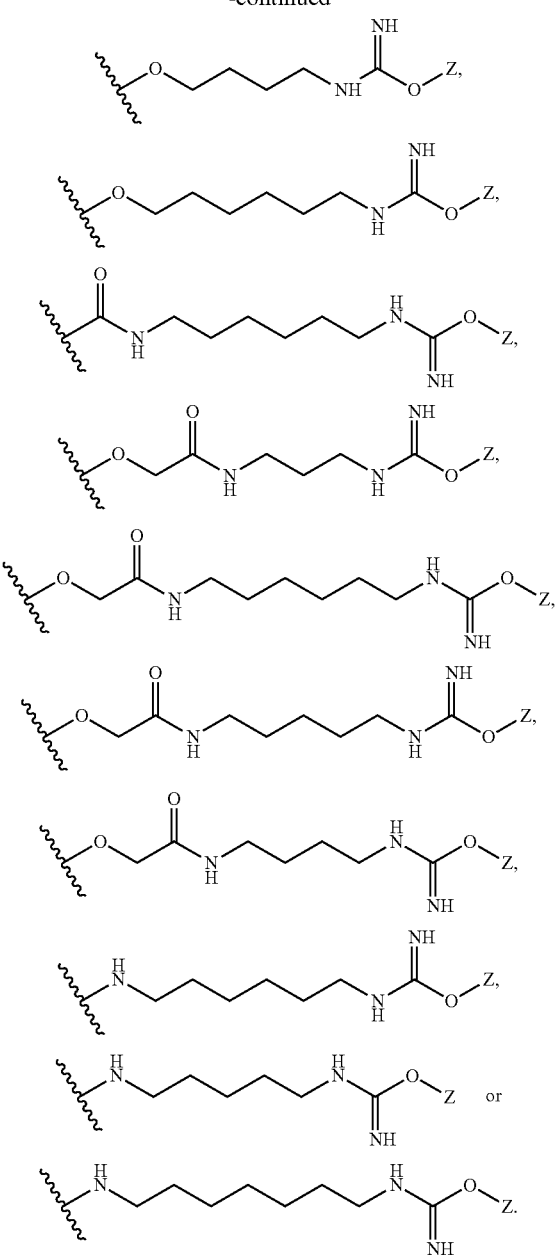
In some embodiments, —X-L-Y—Z is
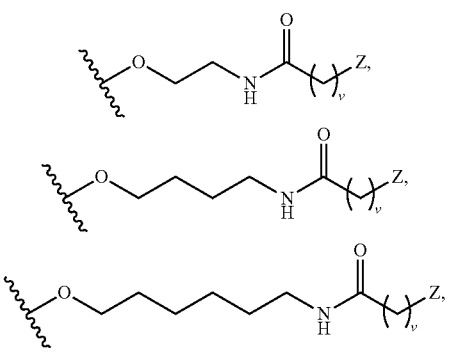

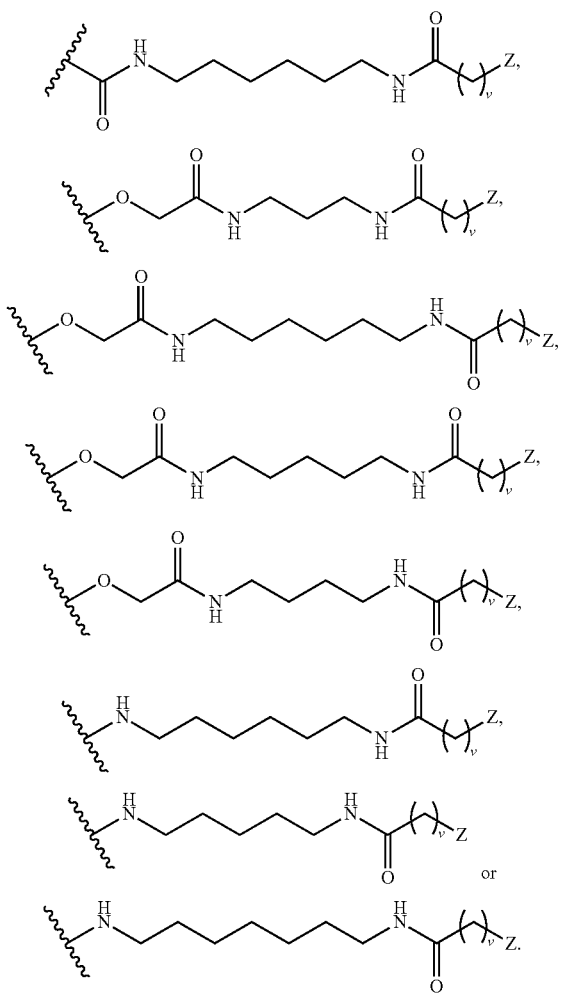

In some embodiments, —X-L-Y—Z is

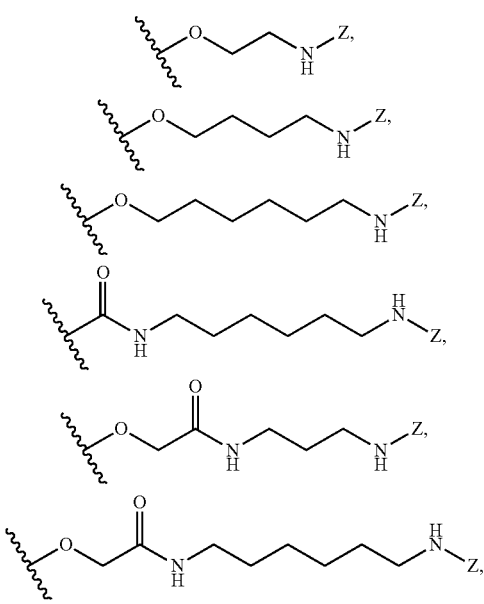

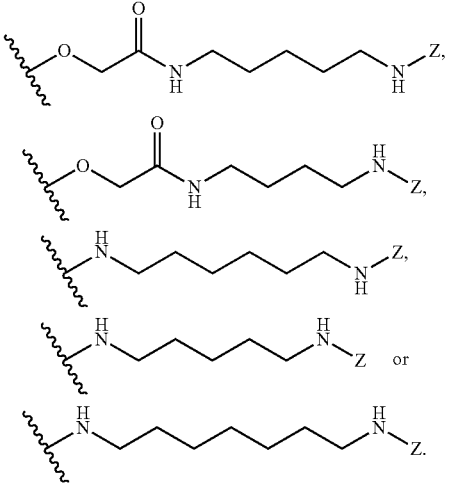

In some embodiments, q is at least 3. In some embodiments, r is at least 3. In some embodiments, s is at least 3. In some embodiments, t is at least 3.

In some embodiments, Z is selected from the group consisting of polystyrene, polystyrene resin grafted with polyethylene glycol, polyamide resin, polyacrylamide resin, polydimethylacrylamide resin, silica, dextran and polysaccharide resin. In some embodiments, Z is cross-linked agarose. In some embodiments, Z is a resin comprising a crosslinked, polysaccharide polymer, which can be extracted from seaweed. In some embodiments, Z is Sepharose™ resin. In other embodiments, Z is Capto™ resin.

In some embodiments, the affinity solid support comprises betrixaban covalently bound to the solid support through a linker. Such an affinity solid support can be referred to as betrixaban—solid support, such as betrixaban—Sepharose™ when the solid support is Sepharose™ or betrixaban—Capto™ when the solid support is Capto.

In some embodiments, the affinity solid support comprises des-chloro betrixaban covalently bound to the solid support through a linker. Des-chloro betrixaban is of the formula:

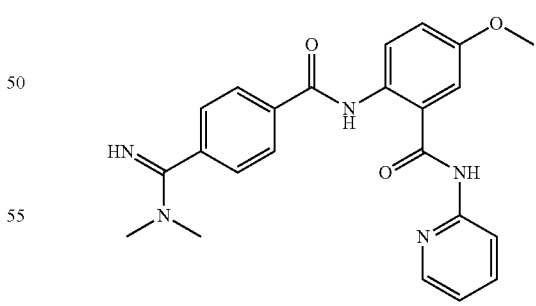

Such an affinity solid support can be referred to as des-chloro betrixaban—solid support, such as des-chloro betrixaban—Sepharose™ when the solid support is Sepharose™ or des-chloro betrixaban—Capto™ when the solid support is Capto™

In some embodiments, the affinity solid support of Formula II is

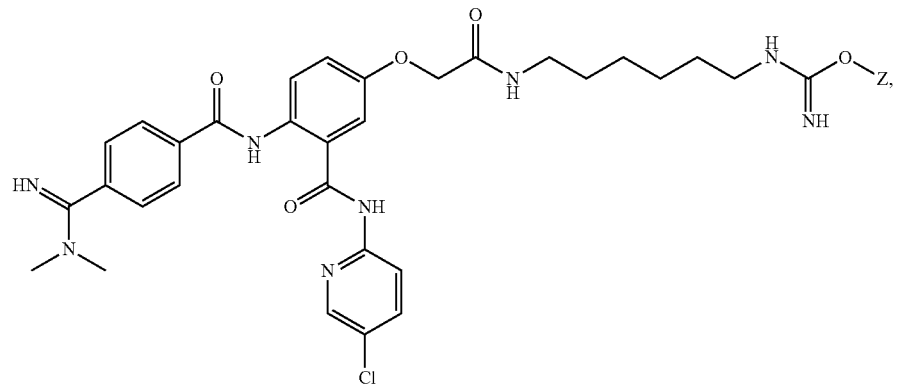
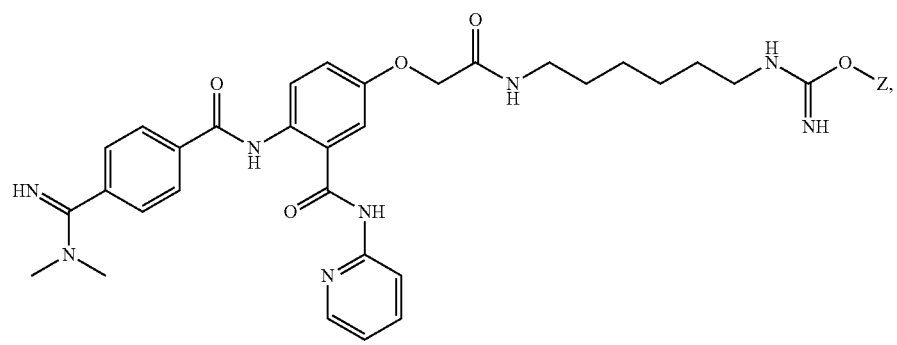
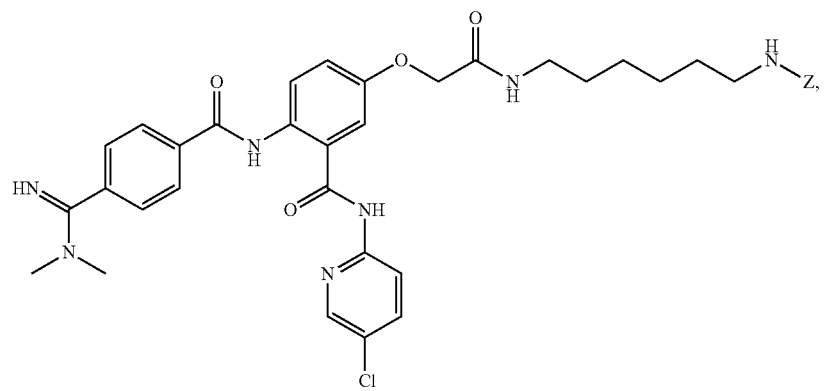
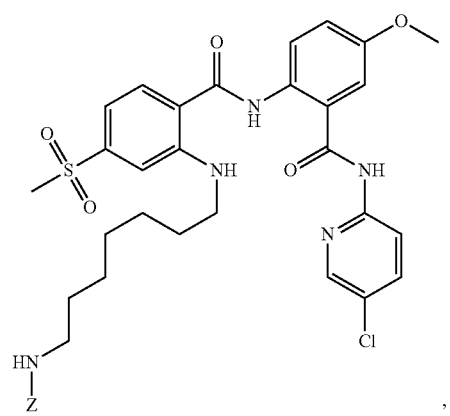

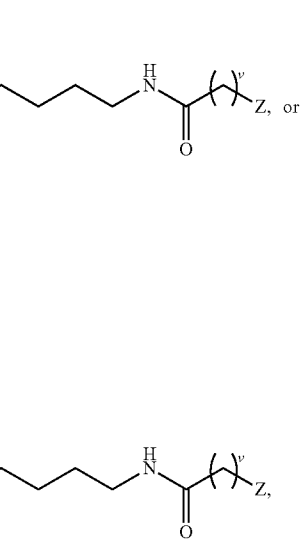
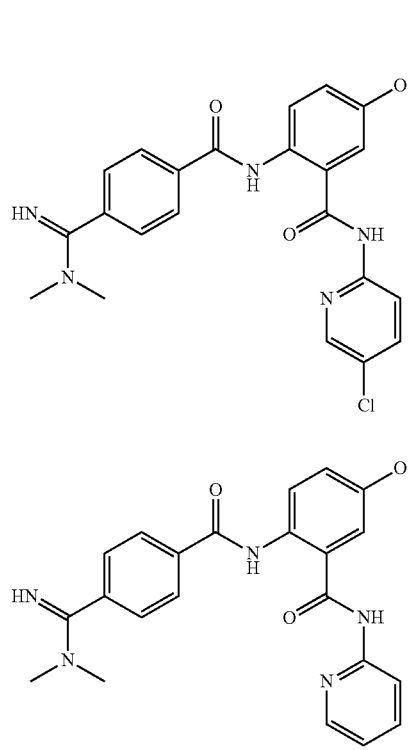

or a salt thereof, wherein Z is a solid support.

In some embodiments, Z is Sepharose™. In other embodiments, Z is Capto™.

In some embodiments, the salt is a pharmaceutically acceptable salt.

Preparation Methods

The compounds and affinity solid supports of this invention can be prepared from readily available starting materials according to the general methods and procedures, and procedures in examples provided herein. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are known in the art. For example, numerous protecting groups are described in T. W. Greene and P. G. M. Wuts, Protecting Groups in Organic Synthesis, Third Edition, Wiley, N.Y., 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for preparing the compounds or affinity solid supports are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the invention may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

In one aspect, provided is a method of preparing an affinity solid support of Formula II or a salt thereof comprising contacting a compound of Formula I or a salt thereof with a solid support capable of forming a covalent bond with the compound of Formula I, wherein the affinity solid support of Formula II, the compound of Formula I and the solid support are as defined herein.

In some embodiments, provided is a method of preparing an affinity solid support of Formula II-A or a salt thereof comprising contacting a compound of Formula I-A, or a salt thereof, with a solid support of the formula NC—O—Z, wherein the affinity solid support of Formula II-A, the compound of Formula I-A and Z are as defined herein. The method is illustrated in Scheme 1.

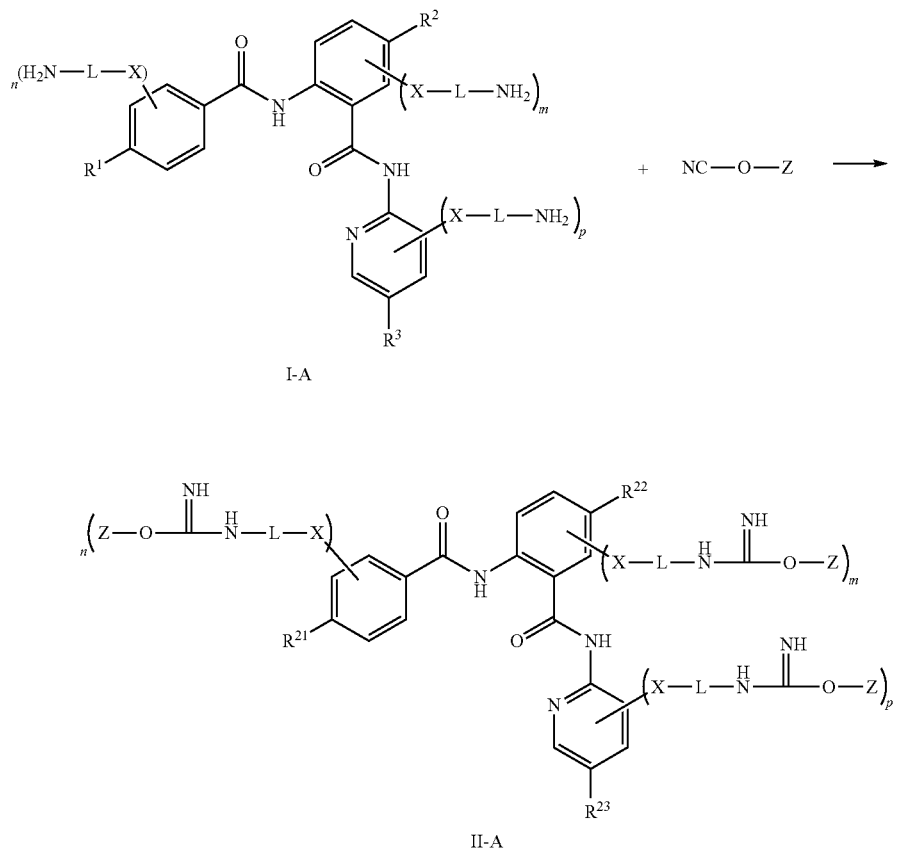

The variables in the Scheme 1 are as defined herein. The compound of Formula I-A can be coupled to commercially available CNBr-activated Sepharose™ using standard coupling techniques. For example, CNBr-activated Sepharose™ 4-FF or CNBr-activated Sepharose™ 4B (Amersham) resin can be hydrated and optionally washed with a low pH aqueous solution (e.g., about 1 mM aqueous HCl solution). A solution comprising a compound of Formula I-A in a suitable solvent, such as a mixture of a water miscible organic solvent (e.g., DMSO) and a suitable buffer (e.g., pH at about 8-9, e.g., about 8.3) can be added to the resin. The mixture is kept at room temperature for a sufficient period of time (e.g., about several hours) while adjusting the pH to about 8-9, e.g., about 8.3, to allow coupling reaction between the compound of Formula I-A and the CNBr group of the resin. The reaction can be monitored by conventional analytical methods, such as HPLC or UPLC. Upon completion of the coupling reaction, unreacted CNBr can be optionally capped with a suitable buffer, such as 0.1 M Tris-HCl buffer at pH 8.0. The coupled resin can be optionally washed with a suitable buffer, such as an acetate buffer (e.g., 0.1 M at a pH of 3 to 4) and/or a Tris-HCl buffer (e.g., 0.1 M at a pH of 8 to 9). The buffers can optionally comprising a suitable amount of NaCl (e.g., 0.5 M). The wash can be repeated.

Similarly, Capto™ resin can be used instead of Sepharose™.

General methods of preparing the solid support for the reaction and reaction conditions for the solid support are described in more detail in Instructions 71-5000-15 AF, 2011, by General Electric Company, which is incorporated by reference in its entirety.

In some embodiments, provided is a method of preparing an affinity solid support of Formula II-B or a salt thereof comprising contacting a compound of Formula I-A, or a salt thereof, with a resin of the formula

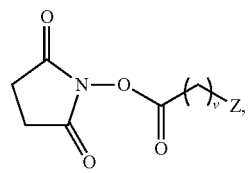

wherein the affinity solid support of Formula II-B, the compound of Formula I-A and Z are as defined herein. The method is illustrated in Scheme 2 wherein all variables are as defined herein.

Scheme 2

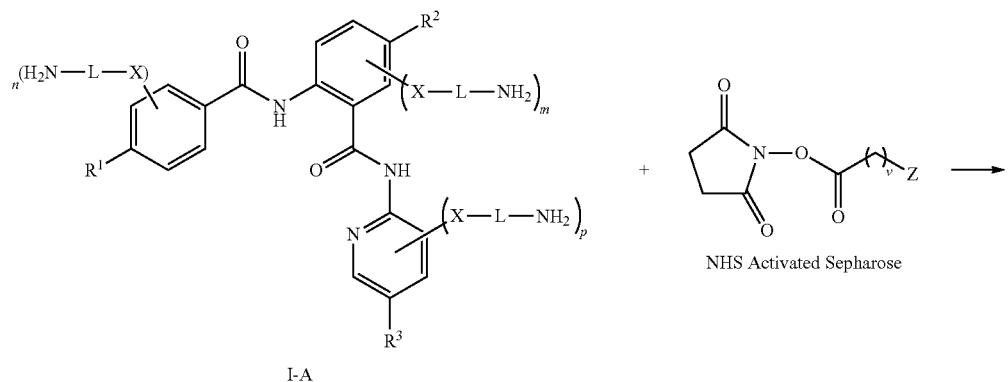

I-A

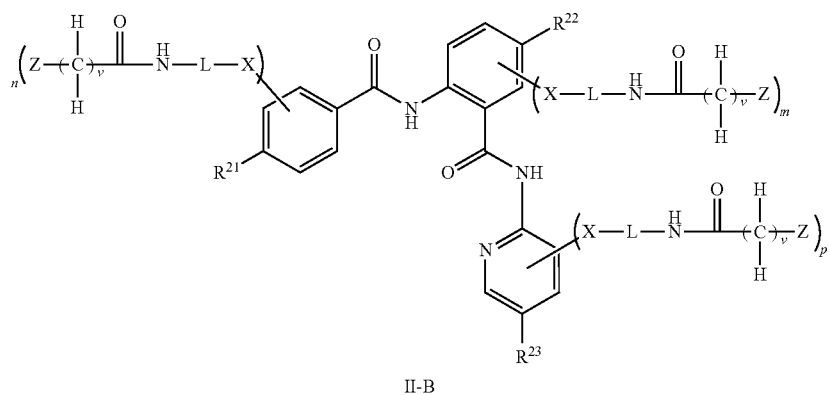

II-B

In some embodiments, the reaction is conducted at a pH of about 6 to 9, such as in a buffer of 0.2 M NaHCO$_3$, 0.5 M NaCl, pH 8.3.

In some embodiments, the solid support is

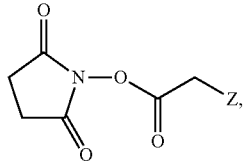

such as NHS-activated Sepharose™ 4 Fast Flow, available from GE Healthcare. General methods of preparing the solid support for the reaction and reaction conditions for the solid support are described in more detail in Instructions 71-5000-14 AD, 2011, by General Electric Company, which is incorporated by reference in its entirety.

In another aspect, provided is a method of preparing an affinity solid support of Formula II-C or a salt thereof comprising contacting a compound of Formula I-D:

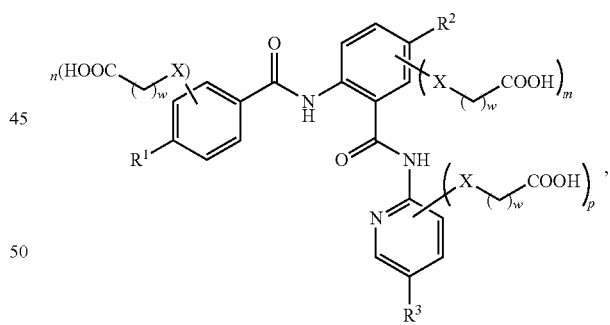

I-D or a salt thereof, with a resin of the formula

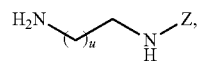

wherein

R$^1$ is —CF$_3$, —SO$_2$CH$_3$, —X-L-R,

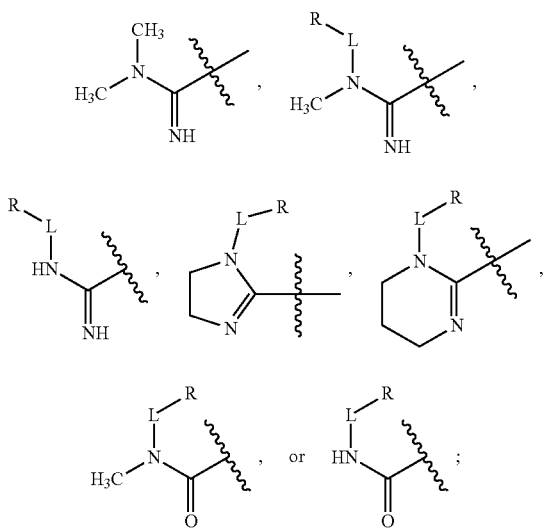

R² is —OCH₃, chloro, or X-L-R;
R³ is hydrogen or chloro;
n, m, and p are either 0 or 1, with the provisos that
(1) when R¹ is —CF₃ or —SO₂CH₃, and R² is —OCH₃ or chloro, then one of n, m, and p must be 1, and the others of n, m, and p must be zero; and
(2) when R¹ is other than —CF₃ or —SO₂CH₃, or R² is X-L-R, then all of n, m, and p must be zero;
the affinity solid support of Formula II-C, u, w and Z are as defined herein.

The method is illustrated in Scheme 3 wherein all variables are as defined herein.

Scheme 3

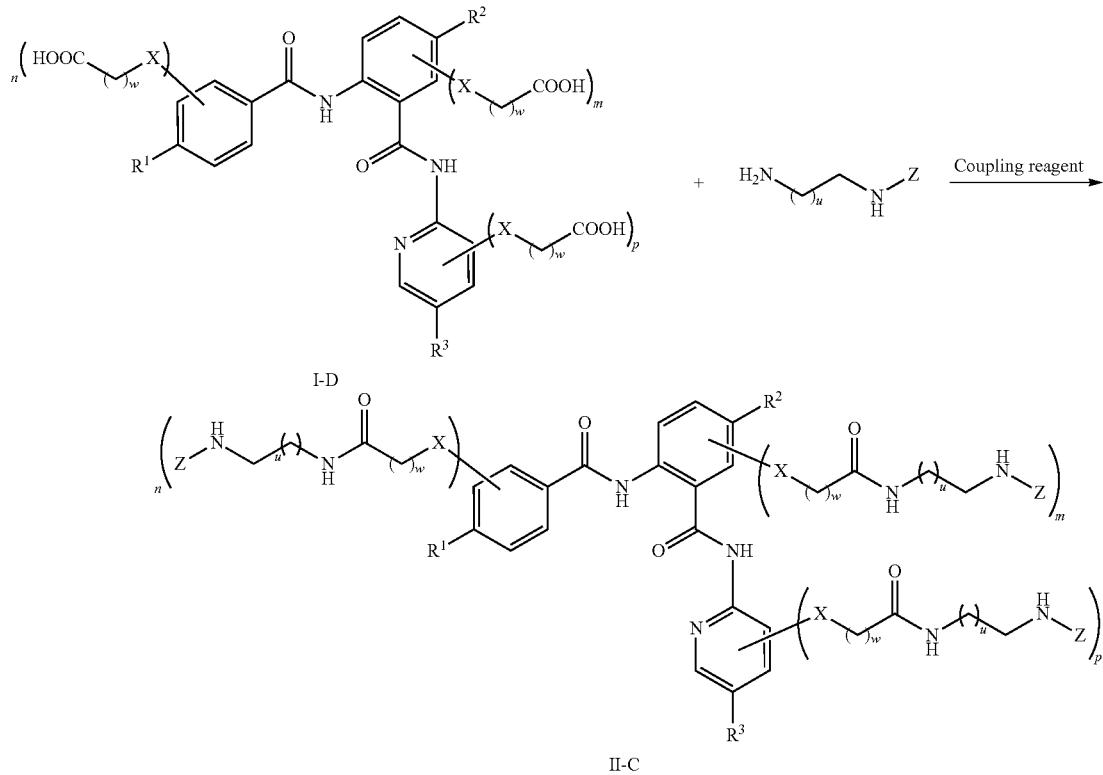

X is a covalent bond, O, S, SO₂, C(O)NH, NHC(O) or NH;

L-R is —(CH₂)$_w$—CO₂H;

R is CO₂H;

In Scheme 3, Compound I-D can be coupled to the resin under conditions comprising an amide coupling reagent. Amide coupling reagent refers to a reagent that may be used to form an amide bond between an amino group and a carboxy group. Examples of coupling reagents include, but are not limited to, carbodiimides such as N,N'-dicyclohexylcarbodiimide (DCC), N,N'-diisopropylcarbodiimide (DIPCDI), and 1-ethyl-3-(3'-dimethylaminopropyl)carbodiimide (EDCI); aminium compounds such as N-[(dimethylamino)-1H-1,2,3-triazolo[4,5-b]pyridine-1-ylmethylene]-N-methyl-methanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethanaminium hexafluorophosphate N-oxide (HCTU), N-[(1H-benzotriazol-1-yl)(dimethylamino)methylene]-N-methylmethanaminium tetrafluoroborate N-oxide (TBTU), and N-[(1H-6-chlorobenzotriazol-1-yl)(dimethylamino)methylene]-N-methyl-methanaminium tetrafluoroborate N-oxide (TCTU); and phosphonium compounds such as 7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (PyBOP). In some embodiments, the coupling reagent is a carbodiimide. In some embodiments, the coupling reagent is EDC. In some embodiments, the coupling is conducted at a pH of about 4.5-6. In some embodiments, the concentration of the coupling reagent is about 10-100 times of the concentration of the functional group on the solid support. In some embodiments, the coupling reagent is in a solution comprising water and optionally a water soluble organic solvent such as dioxane or ethylene glycol.

In some embodiments, the solid support is

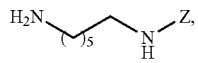

such as EAH Sepharose™ 4B, available from GE Healthcare. General methods of preparing the solid support for the reaction and reaction conditions for the solid support are described in more detail in Instructions 71-7097-00 AE, 2009, by General Electric Company, which is incorporated by reference in its entirety.

Compounds of Formula I can be prepared by the following exemplifying synthetic schemes.

Scheme 4

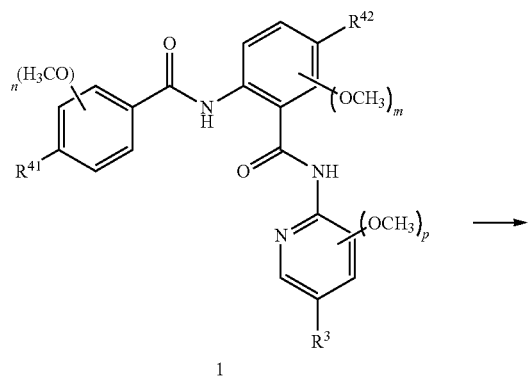

1

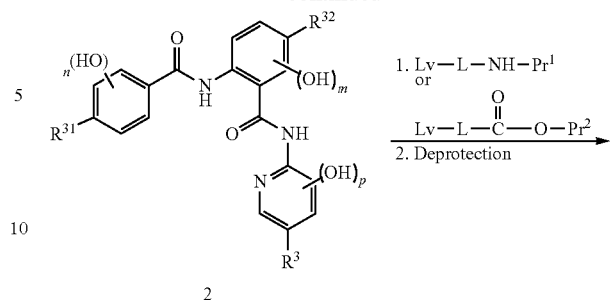

2

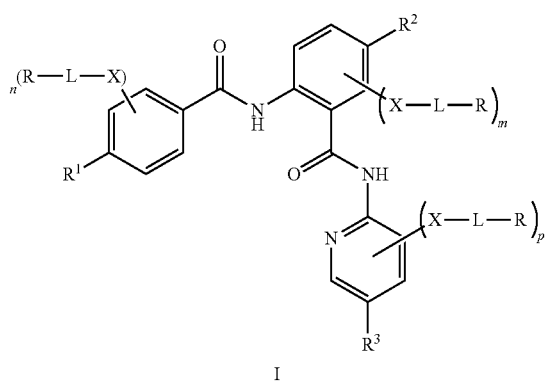

I

In Scheme 4, Lv is a leaving group, $Pr^1$ is an amino protecting group, and $Pr^2$ is an acid protecting group, $R^{41}$ is —$CF_3$, —$SO_2CH_3$, —$OCH_3$, or

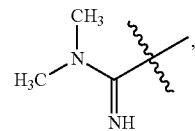

$R^{42}$ is —$OCH_3$ or chloro, $R^{31}$ is —$CF_3$, —$SO_2CH_3$, —OH, $R^{32}$ is —OH, —$OCH_3$ or chloro, $R^1$ is —$CF_3$, —$SO_2CH_3$, —X-L-R or

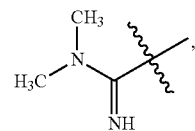

X is O, $R^2$, $R^3$, L, R, m, n, and p are as defined herein unless otherwise stated. Compound 1 can be prepared according to methods described in U.S. Pat. No. 6,376,515. Compound 2 can also be prepared according to methods described in U.S. Pat. No. 6,376,515, or can be prepared from Compound 1 by demethylation of the methoxy group with under appropriate conditions, such as using $BBr_3$ in a suitable organic solvent, such as methylene chloride. Compound 2 can then be coupled to a compound of Lv-L-NH—$Pr^1$ or Lv-L-C(O)O—$Pr^2$, followed by deprotection to provide a compound of Formula I wherein X is O, $R^1$ is —$CF_3$, —$SO_2CH_3$,

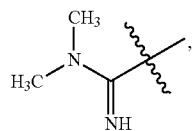 [SMILES: *C(=N)N(C)C]

or —X-L-R.

Leaving groups, amino protecting groups and acid protecting groups and methods of deprotection are generally known in the field, and many are described in T. W. Greene and G. M. Wuts, *Protecting Groups in Organic Synthesis*, Third Edition, Wiley, N.Y., 1999, and references cited therein, which are incorporated by reference in their entirety. Non-limiting examples of leaving groups include chloro, bromo, iodo, tosylate, triflate, etc. Non-limiting examples of amino protecting groups include N-tert-butoxycarbonyl (t-Boc), 9-fluorenylmethoxycarbonyl (Fmoc), carboxybenzyl (Cbz), acetyl (Ac), benzoyl (Bz), p-methoxybenzyl carbonyl (Moz or MeOZ), benzyl (Bn), p-methoxybenzyl (PMB), 3,4-dimethoxybenzyl (DMPM), p-methoxyphenyl (PMP), etc. Non-limiting examples of carboxy protecting groups include esters of $C_1$-$C_6$ alkyl, such as methyl or ethyl, which can be deprotected by hydrolysis with a base (e.g., sodium hydroxide or potassium carbonate), t-butyl (t-Bu) which can be deprotected by acid hydrolysis (e.g., hydrochloric acid (HCl) or trifluoroacetic acid (TFA)), or benzyl which can be deprotected by hydrogenation with hydrogen in the presence of a catalyst, such as palladium.

Compound 2 in Scheme 1 can be replaced with Compound 3, wherein $R^{51}$ is —$CF_3$, —$SO_2CH_3$,

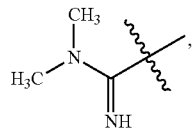 [SMILES: *C(=N)N(C)C]

or $NH_2$, $R^{52}$ is —$OCH_3$, $NH_2$ or chloro, which can react with Lv-L-NH—$Pr^1$ or Lv-L-C(O)O—$Pr^2$, followed by deprotection to give compound of Formula I where X is NH, $R^1$ is —$CF_3$, —$SO_2CH_3$,

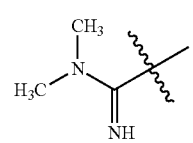 [SMILES: *C(=N)N(C)C]

or —X-L-R. Compound 3 can also be prepared by methods described in U.S. Pat. No. 6,376,515.

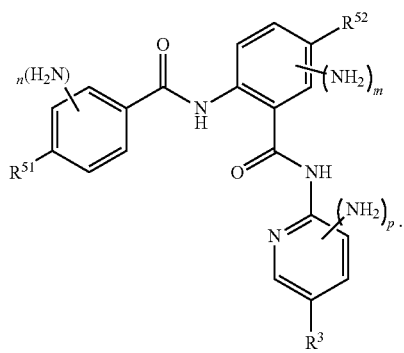

3

Scheme 5

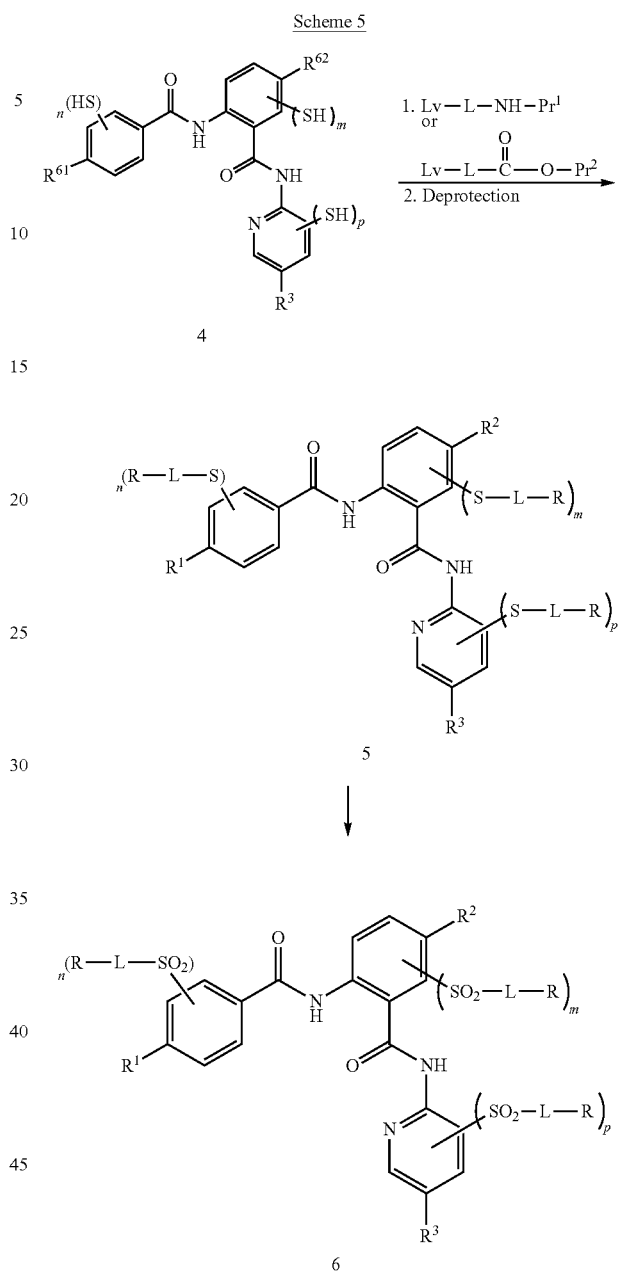

Scheme 5 shows an exemplifying procedure for preparing a compound of Formula I wherein X is S or $SO_2$. In Scheme 2, Lv is a leaving group, $Pr^1$ is an amino protecting group and $Pr^2$ is an acid protecting group, $R^{61}$ is —$CF_3$, —$SO_2CH_3$,

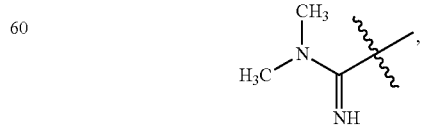

or SH, $R^{62}$ is —$OCH_3$, SH or chloro, $R^1$ is —$CF_3$, —$SO_2CH_3$,

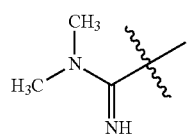 [SMILES: *C(=N)N(C)C]

—SO$_2$CH$_3$, or —X-L-R, R$^2$, R$^3$, L, R, m, n, and p are as defined herein unless otherwise stated. Compound 4, which can also be prepared according to methods described in U.S. Pat. No. 6,376,515, reacts with Lv-L-NH—Pr$^1$ or Lv-L-C(O)O—Pr$^2$, followed by deprotection to give Compound 5, i.e., a compound of Formula I where X is S. Compound 5 can be oxidized by a suitable oxidation reagent, such as hydrogen peroxide, m-chloroperbenzoic acid and manganese dioxide, to provide Compound 6, i.e., a compound of Formula I where X is SO$_2$.

Purification Methods and Serine Proteases

In certain embodiments, the serine protease that is purified by the methods described herein is a fXa derivative. Certain fXa derivatives are described in U.S. Pat. No. 8,153,590, which is herein incorporated by reference in its entirety. For example, the serine protease is a polypeptide comprising the amino acid sequence of SEQ ID NO: 1, 2 or 4 or a polypeptide having at least about 80% sequence identity to SEQ ID NO: 1, 2 or 4. The fXa derivative represented by SEQ ID NO: 1 contains three mutations relative to wild-type fXa. The first mutation is the deletion in the Gla-domain of FX at position 6-39 in the wild-type protein. The second mutation replaces the activation peptide sequence 143-194 aa with -RKR-. This produced a -RKRRKR- (SEQ ID NO: 3) linker connecting the light chain and the heavy chain. Upon secretion, this linker is cleaved in CHO resulting in a two-chain fXa molecule (SEQ ID NO: 2). The third mutation is mutation of active site residue 5379 to an Ala residue (based on secreted human fX amino acid sequence). This amino acid substitution corresponds to amino acid at position 296 and position 290 of SEQ ID NOS: 1 and 2, respectively. The fXa derivative does not compete with fXa in assembling into the prothrombinase complex, but instead bind and/or substantially neutralize the anticoagulants, such as fXa inhibitors. The derivatives useful as antidotes are modified to reduce or remove intrinsic procoagulant and anticoagulant activities, while retaining the ability to bind to the inhibitors. Structurally, in one embodiment, the derivatives are modified to provide either no procoagulant activity or reduced procoagulant activity. "Procoagulant activity" is referred to herein as an agent's ability to cause blood coagulation or clot formation. Reduced procoagulant activity means that the procoagulant activity has been reduced by at least about 50%, or more than about 90%, or more than about 95% as compared to wild-type fXa. In a related embodiment, the amino acid sequence having at least 80% sequence identity to SEQ ID NO: 2 has reduced procoagulant activity compared to wild-type factor Xa. In a further embodiment, the amino acid sequence having at least 80% sequence identity to SEQ ID NO: 2 does not assemble into a prothrombinase complex. The serine protease purified herein includes salts of the serine protease.

A further aspect disclosed herein relates to a purified serine protease comprising the amino acid sequence of SEQ ID NO: 2 or a polypeptide having at least about 80%, at least about 85%, at least about 90%, at least about 95%, at least about 97%, at least about 98%, or at least about 99% sequence identity to SEQ ID NO: 2 wherein the polypeptide is produced by the methods described herein. U.S. Pat. Nos. 8,153,590 and 8,268,783 describe serine protease proteins, modifications, and methods of preparing the proteins, and are incorporated by reference in their entirety. In some embodiments, the purified serine protease comprises at least 85% of the amino acid sequence of SEQ ID NO: 2 (the alpha form of r-Antidote) and no more than 10% of the amino acid sequence of SEQ ID NO: 4 (the beta form of r-Antidote). In some embodiments, the purified serine protease comprises no more than 8% of the amino acid sequence of SEQ ID NO: 4 (the beta form of r-Antidote).

The serine protease can be recombinantly produced as previously described, e.g., in U.S. Patent Publication No. US 2013-0230901, or by other methods of recombinant protein production known in the art. For example, proteins may be cloned into a DNA construct (i.e. plasmids, viral vectors, cosmids, expression vectors, phagemids, fosmids, and artificial chromosomes such as bacterial artificial chromosomes, yeast artificial chromosomes, and human artificial chromosomes) and introduced into a suitable host cell by gene transfer techniques such chemical-based transfection, such as calcium phosphate transfection and polyfection, and non chemical-based transfection such as electroporation, optical transfection, and gene electrotransfer. Suitable host cells include prokaryotic and eukaryotic cells, which include, but are not limited to bacterial cells, yeast cells, insect cells, animal cells, mammalian cells, murine cells, rat cells, sheep cells, simian cells and human cells. Cells can then be lysed by physical techniques such as sonication or freeze-thaw or by the use of detergents or lysis buffers such as RIPA Buffer (Radi-Immunoprecipitation Assay) containing 150 mM NaCl, 1.0% IGEPAL™ CA-630, 0.5% sodium deoxycholate, 0.1% SDS, and 50 mM Tris, pH 8.0, or by physical separation, such as centrifugation or filtration, to obtain the clarified harvested culture fluid from mammalian cell cultures. The resulting soluble protein extract may be then used in the purification methods described herein.

U.S. Patent Publication No. US 2013-0230901, which is herein incorporated by reference in its entirety, describes methods and cells for the improved or enhanced processing of the one-chain r-Antidote precursor to the cleaved two-chain r-Antidote protein that acts as an antidote to fXa inhibitors. WO 2013/188587 describes methods for purifying serine proteases (e.g., r-Antidote) in active form from a composition containing the serine proteases a STI based affinity resin. STI affinity resin having a protein usually is reusable for a limited number of times and is expensive to manufacture. The purification methods described herein employ small molecule compounds that can be readily prepared and attached to a solid support, and are reusable. The methods are suitable for large scale purification, and can provide higher binding capacity and improved purity. The small molecule compounds can provide different levels of binding affinities with different serine proteases so that selectivity and specificity with a particular serine protease can be obtained. The methods are contemplated to provide increased yield.

In one aspect, the method comprises
(1) adding a first composition comprising the serine protease to an affinity solid support of Formula II or a salt thereof to form a second composition comprising the serine protease and the affinity solid support of Formula II, and
(2) eluting the serine protease from the second composition with an elution buffer comprising a competitive agent, wherein the affinity solid support of Formula II is as defined herein.

In another aspect, provided is a purified serine protease, which is purified by a method comprising
(1) adding a first composition comprising the serine protease to an affinity solid support of Formula II or a salt thereof to form a second composition comprising the serine protease and the affinity solid support of Formula II, and
(2) eluting the serine protease from the second composition with an elution buffer comprising a competitive agent,
wherein the affinity solid support of Formula II is as defined herein.

As described herein, the affinity solid support of Formula II comprises a compound covalently bound to the solid support which compound has binding affinity towards the serine protease. The second composition comprising the serine protease and the affinity solid support of Formula II is formed through non-covalent binding between the serine protease and the compound on the affinity solid support of Formula II. Such non-covalent binding includes one or more binding interactions, such as hydrogen bonds, ionic bonds, van der Waals forces, and hydrophobic interactions, etc., between the compound on the affinity solid support of Formula II and one or more amino acid residues of the serine protease.

In some embodiments, the amount of the serine protease bound to the affinity solid support is at least 50%, at least 60%, at least 70% or at least 80% of the binding capacity of the affinity solid support.

In some embodiments, the amount of the serine protease bound to the affinity solid support is at least 150%, 200%, 250% or 300% of that bound to a STI affinity solid support per unit volume of the solid support.

In some embodiments, at least 50%, at least 60%, at least 70% or at least 80% of the seine protease is recovered after purification.

In some embodiments, the method further comprises washing the second composition with a washing buffer after step (1) and prior to step (2).

In one embodiment, the affinity solid support of Formula II is contained in a column. The serine protease may be added to the column under conditions that allow for the absorption of the serine protease on to the column, and the column may be washed with a washing buffer that allows for the continued absorption of the serine protease to the column and the elution of contaminating proteins or molecules in the flow-through.

The serine protease may then be eluted with an elution buffer comprising a competitive agent, a salt, a detergent, or a chaotropic agent. The competitive agent may be benzamidine and/or arginine, or a pharmaceutically acceptable salt thereof.

In one embodiment, the competitive agent is arginine. Elution with arginine is advantageous because it is a GRAS (Generally Recognized As Safe) excipient and does not need to be removed from the purified protein. An additional benefit of arginine is that it actually improves the solubility of a serine protease (e.g., r-Antidote) and can be used as an excipient in the final formulation.

The concentration of arginine or the competitive agent employed in the elution buffer may be from about 250 mM to about 1000 mM. In one embodiment, the concentration of arginine or the competitive agent in the elution buffer is about 500 mM. In further embodiments, the concentration is about 250 mM, or about 300 mM, or about 350 mM, or about 400 mM, or about 450 mM, or about 550 mM, or about 600 mM, or about 650 mM, or about 700 mM, or about 750 mM, or about 800 mM, or about 850 mM, or about 900 mM, or about 1 M. The elution buffer optionally further comprises a salt, a detergent, or a chaotropic agent. Salts useful in the elution buffer of the methods and kits disclosed herein include sodium chloride, ammonium chloride, sodium citrate, potassium citrate, potassium chloride, magnesium chloride, calcium chloride, sodium phosphate, calcium phosphate, ammonium phosphate, magnesium phosphate, potassium phosphate, sodium sulfate, ammonium sulfate, potassium sulfate, magnesium sulfate, calcium sulfate, etc. Detergents useful in the elution buffer of the methods and kits disclosed herein include, for example, polysorbate 80, urea, guanidine, etc.

The pH of the elution buffer is one that allows for the effective elution of a serine protease protein absorbed on the resin without causing inactivation and/or precipitation of the serine protease. Certain fXa derivatives such as r-Antidote are inactivated or precipitate at low pH. In certain embodiments, the pH of the elution buffer is from about 4.5 to about 10.5. In another embodiment, the pH of the elution buffer is about pH 5.0. In another embodiment, the pH of the elution buffer is about pH 7.4. Alternatively, the pH of the elution buffer is at least about 4.5, about 5.5, about 6, about 6.5, about 7, about 7.5, about 8.0, about 8.5, about 9, about 9.5, or at least about 10. In another embodiment, the pH of the elution buffer is not higher than about 5.5, about 6, about 6.5, about 7, about 7.5, about 8.0, about 8.5, about 9, about 9.5, about 10, or not higher than about 10.5. In one embodiment, the pH of the elution buffer is about 7.4 when benzamidine is used as the competitive agent. In one embodiment, the pH of the elution buffer is about 5.0 when arginine is used as the competitive agent.

In one embodiment, the washing buffer may comprise a salt and be at a neutral pH. The term "neutral pH" is intended to mean a pH from about 6 to about 8. In certain embodiments, the washing buffer comprises from about 200 to about 500 mM NaCl at a neutral pH. In another embodiment, the buffer further comprises about 10 to 50 mM, for example, about 20 mM Tris. In other embodiments, the pH is about 6, or about 7, or about 8.

The methods disclosed herein may further comprise other purification and chromatographic steps such as, for example, gel electrophoresis such as polyacrylamide gel electrophoresis, ion-exchange chromatography, reverse phase chromatography, mixed-mode resins, exclusion chromatography, affinity chromatography, or other chromatography techniques, isoelectric focusing, precipitation with ammonium sulfate, PEG (polyethylene glycol), antibodies and the like or by heat denaturation, followed by centrifugation; filtration such as gel filtration, hydroxylapatite; or combinations of such and other techniques. In one embodiment, the method further comprises applying the solution containing the polypeptide to an ion-exchange column.

Suitable cation-exchange resins include a wide variety of materials known in the art, including those capable of binding polypeptides over a wide pH range. For example, carboxymethylated, sulfonated, agarose-based, or polymeric polystyrene/divinyl benzene cation-exchange matrices are particularly preferred. Other useful matrix materials include, but are not limited to, cellulose matrices, such as fibrous, microgranular, and beaded matrices; dextran, polyacrylate, polyvinyl, polystyrene, silica, and polyether matrices; and composites. Other suitable materials for use in cation exchange chromatography are within the knowledge of those skilled in the art.

Anion-exchange chromatography is carried out using media appropriate therefor, as are known in the art. Suitable media include, e.g., polymeric polystyrene/divinyl benzene resins and agarose-based resins, as well as agarose beads, dextran beads, polystyrene beads, media that comprise an insoluble, particulate support derivatized with tertiary or quaternary amino groups, and supports derivatized with trimethylaminoethyl groups. Examples of suitable such media include DE92 (diethylaminoethyl cellulose, Whatman); DEAE CELLULOSE (Sigma), BAKERBOND ABX 40 mu (J. T. Baker, Inc.); DEAE resins such as FRACTOGEL EMD DEAE-650 (EM Separations), FRACTOGEL EMD TMAE-650 (S)™ (EM Science, Gibbstown, N.J.), TSK gel DEAE-SPW (Tosohaas), DEAE-SEPHAROSE CL-6BT" and chelating SEPHAROSE (Amersham Pharmacia Biotech AB), DEAE MERE SEP. IOOO™ (Millipore), and DEAE SPHERODEX (Sepracor); RESOURCE Q™ and Q SEPHAROSE (QSFF) (Amersham Pharmacia Biotech AB); MACRO-PEP Q™ (Bio-Rad Laboratories, Hercules, Calif.); Q-HYPERD (BioSepra, Inc., Marlborough, Mass.); and the like. Other suitable anion-exchange chromatography materials, as well as the selection and use of these materials for the present application, are conventional in the art.

The ion-exchange chromatography, filtration, nanofiltration, or additional purification step may be prior to or after the affinity chromatography described herein. Additional steps may also include viral inactivation steps by, for example, solvent and detergent treatment of the protein extract or through nanofiltration.

Multi-modal or mixed-mode chromatography (MMC) methods are also used for purification of proteins and other biologics. Examples of commercial multi-modal chromatography resins include ceramic hydroxyapatite (CHT), Capto-MMC, Capto-Adhere, Capto-Q, Capto-S, Capto-Octyl, Capto-CHT, and the like.

Generally, "purified" will refer to a protein or peptide composition that has been subjected to fractionation to remove various other components, and which composition substantially retains its expressed biological activity. A substantially purified protein or peptide in a composition forms the major component of the composition, such as constituting at least about 50%, at least about 60%, at least about 70%, at least about 80%, at least about 90%, at least about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Kits

Also provided herein is a kit for purifying a serine protease.

In one aspect, provided is kit for purifying a serine protease comprising
 (1) an affinity solid support of Formula II or a salt thereof, and
 (2) an elution buffer comprising a competitive agent, wherein the affinity solid support of Formula II is as defined herein.

In another aspect, provided is a kit for purifying a serine protease comprising a compound of Formula I or a salt thereof and an activated solid support capable of forming a covalent bond with the compound of Formula I, wherein the compound of Formula I and the activated solid support are as defined herein.

In some embodiments, the kit further comprises an elution buffer comprising a competitive agent.

In some embodiments, the competitive agent is arginine and/or benzamidine, or a salt, such as a pharmaceutically acceptable salt thereof.

In one embodiment, the kit further comprises a washing buffer. In a related embodiment, the washing buffer comprises about 250 mM NaCl at a neutral pH. In another embodiments, the buffer further comprises about 10 to 50 mM, for example, about 20 mM Tris.

EXAMPLES

The examples below as well as throughout the application, the following abbreviations have the following meanings. If not defined, the terms have their generally accepted meanings.

atm=atmosphere
Boc=tert-butoxycarbonyl
BOP=(benzotriazol-1-yloxy)tris(dimethylamino)phosphonium hexafluorophosphate
DCM=dichloromethane
DIEA=N,N-diisopropylethylamine
DMAP=dimethylaminopyridine
DMF=dimethylformamide
DMSO=dimethylsulfoxide
eq.=equivalent
ESMS=electrospray mass spectrometry
EtOAc=ethyl acetate
EtOH=ethanol
HPLC=high-performance liquid chromatography
g=gram
MeOH=methanol
mg=milligram
min=minute
mL=milliliter
mM=millimolar
mmol=millimole
MS=mass spectrometry
N (when used as concentration unit)=normal
nm=nanometer
nM=nanomolar
pM=picomolar
TEA=triethylamine
TFA=trifluoroacetic acid
UPLC=ultra performance liquid chromatography
UV=ultraviolet spectrum
µL=microliter
µM=micromolar
λ=wavelength

Example 1

Preparation of 5-(2-(((6-amidohexyl)amino)-2-oxo-ethyoxy)-N-(5-chloropyridin-2-yl)-2-(4-(N,N-dimethylcarbamimidoyl)benzamido)benzamide (Compound A3)

1. Preparation of tert-butyl(6-(2-chloroacetamido)hexyl)carbamate, Compound B2

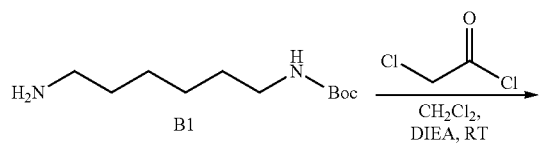

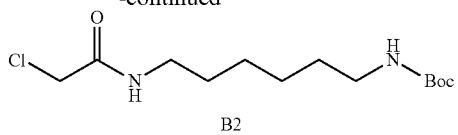

To a solution of N-Boc-1,6-hexanediamine, Compound B1 (376 mg, 1.74 mmol) in CH$_2$Cl$_2$ (8 mL) was added DIEA (0.500 mL, 2.87 mmol) at room temperature. To this was added dropwise chloroacetyl chloride (0.138 mL, 1.73 mmol). The mixture was stirred at room temperature for 4 hour, diluted with EtOAc, washed with 1N HCl and 5% NaHCO$_3$. The organic layer was dried, filtered and concentrated in vacuum to give semi-solid compound B2 (434 mg).

2. Preparation of Compound A3

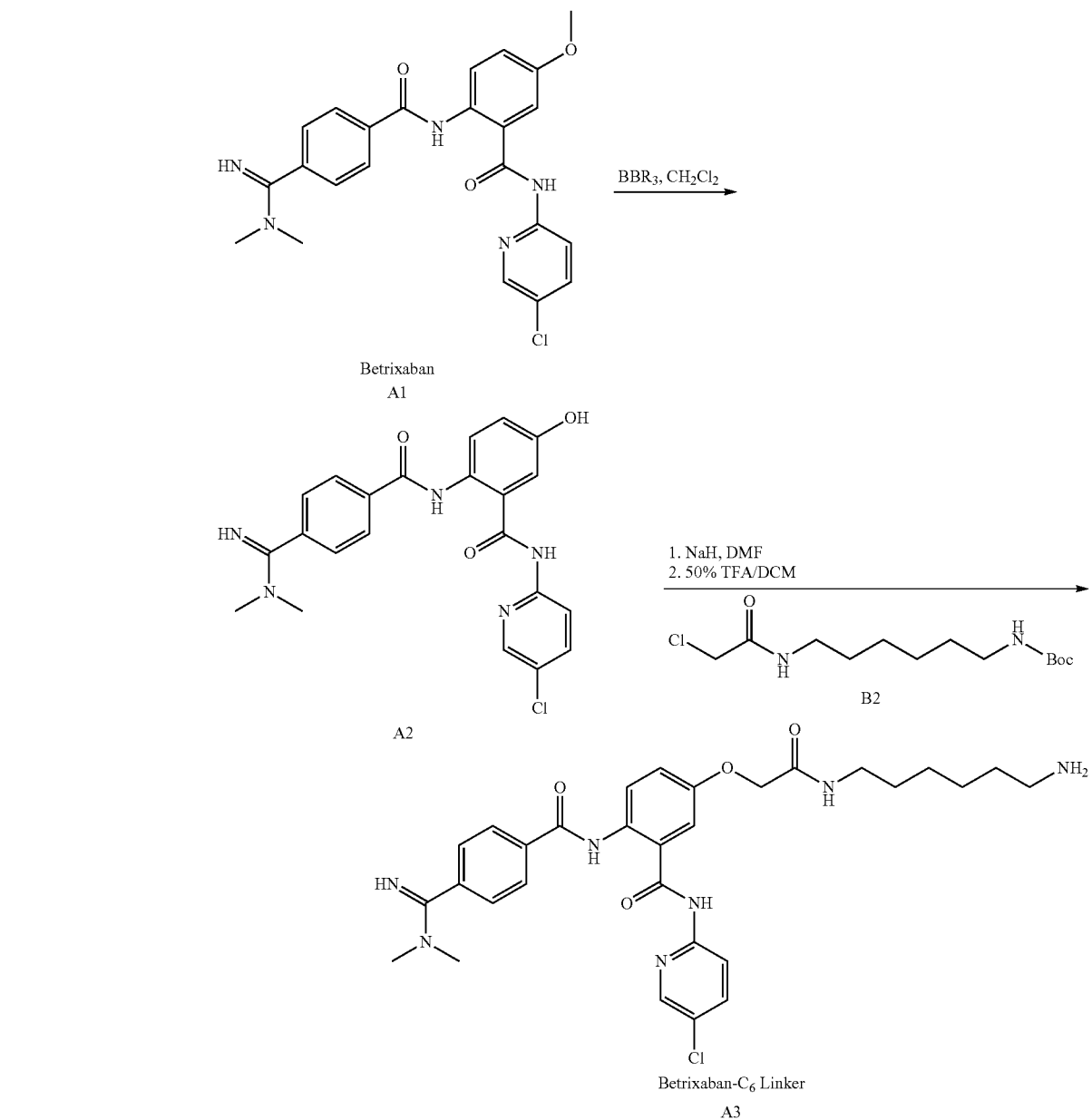

To a mixture of betrixaban, Compound A1 (1.00 g, 2.21 mmol) in dichloromethane (15 mL) was added BBr$_3$ (1.5 mL, 15.70 mmol). The reaction mixture was stirred at room temperature overnight. To the reaction mixture was added water, the solid precipitated was collected by filtration, dried under vacuum to afford compound A2 (1.10 g).

A mixture of Compound A2 (240 mg, 0.548 mmol), Compound B2 (210 mg, 0.718 mmol) and NaH (60%, 65 mg, 1.62 mmol) in DMF (4 mL) was stirred at room temperature for 6 hours. To the mixture was added water and the sticky solid precipitated was taken to the next step as such.

The solid from the above reaction was treated with neat TFA at room temperature for 1 hour. The mixture was concentrated and subjected to reverse phase preparative HPLC to provide the title Compound A3 (150 mg). MS found for $C_{30}H_{36}ClN_7O_4$ as $(M+H)^+$ 594.6. UV: $\lambda$=202, 287.8 nm.

Example 2

Preparation of 5-(2-(((6-amidohexyl)amino)-2-oxo-ethyoxy)-2-(4-(N,N-dimethylcarbamimidoyl)benzamido)-N-(pyridine-2-yl)benzamide (Compound A4)

Route 1:

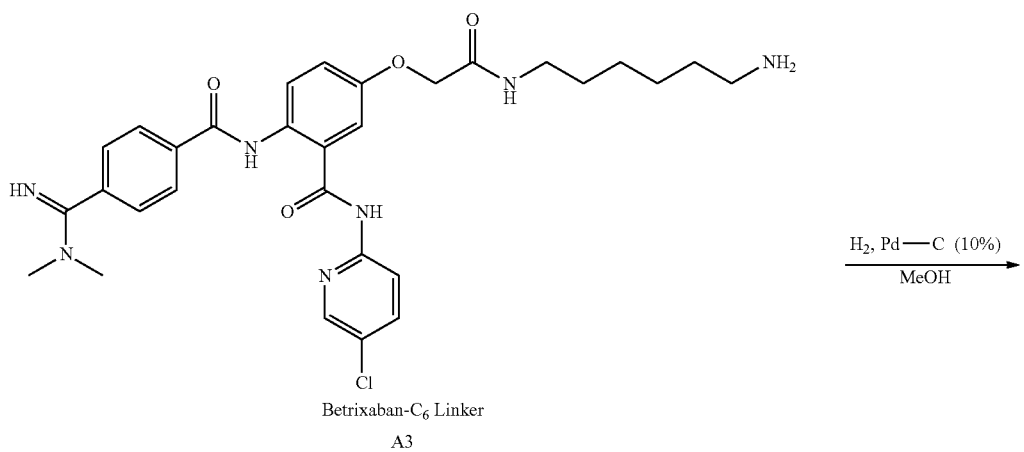

Betrixaban-C$_6$ Linker
A3

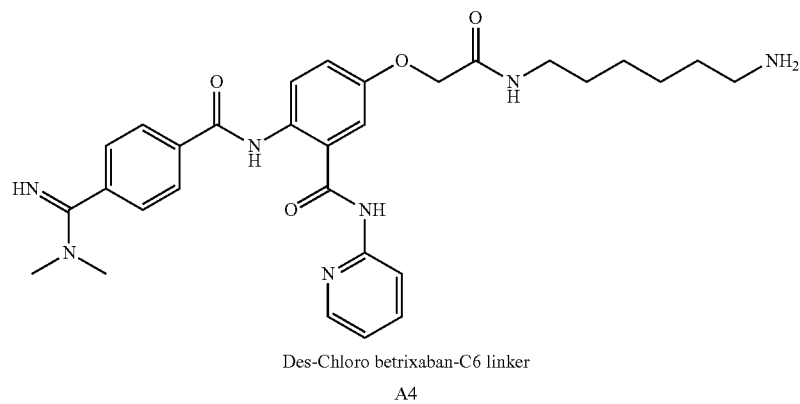

Des-Chloro betrixaban-C6 linker
A4

A mixture of Compound A3 (102 mg, 0.171 mmol) and Pd/C (10%, 49 mg) in MeOH was hydrogenated under balloon H$_2$ for 4 hours. The reaction mixture was filtered through celite plug, concentrated in vacuo and purified by reverse phase preparative HPLC to isolate the title Compound A4 (31 mg). MS found for $C_{30}H_{37}N_7O_4$ as $(M+H)^+$ 560.43. UV: $\lambda$=204, 231.5, 294 nm.

Route 2:
Compound A4 can be prepared according to:
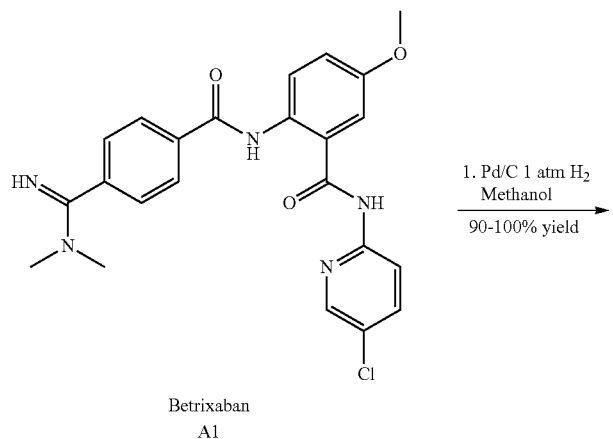
Betrixaban
A1
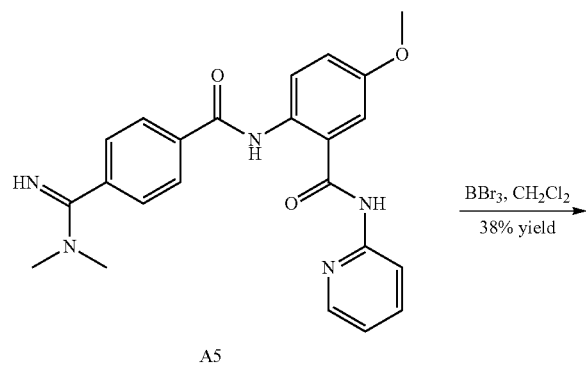
A5
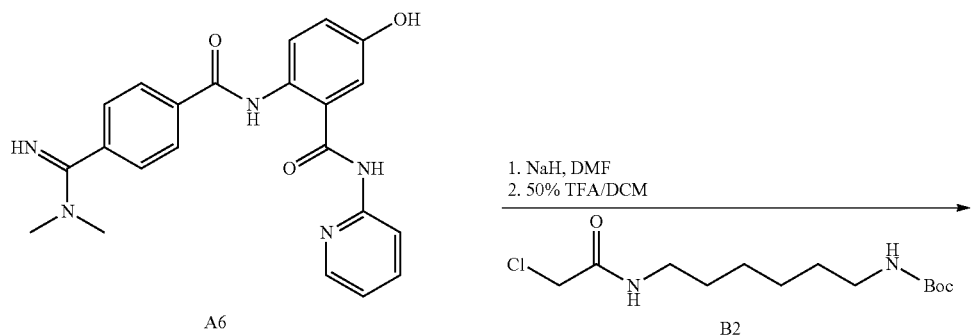
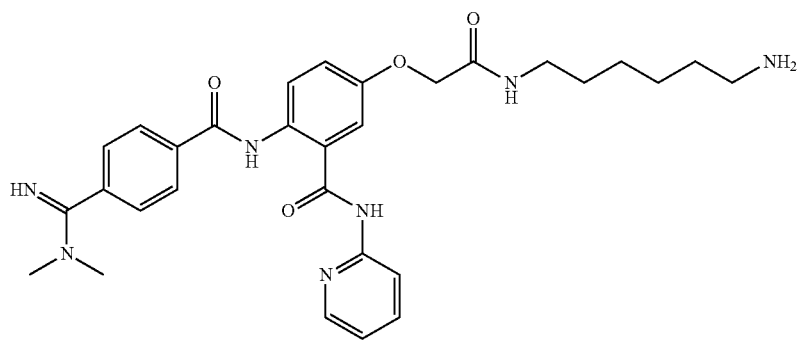
Des-Chloro betrixaban-C6 linker
A4

Route 3:
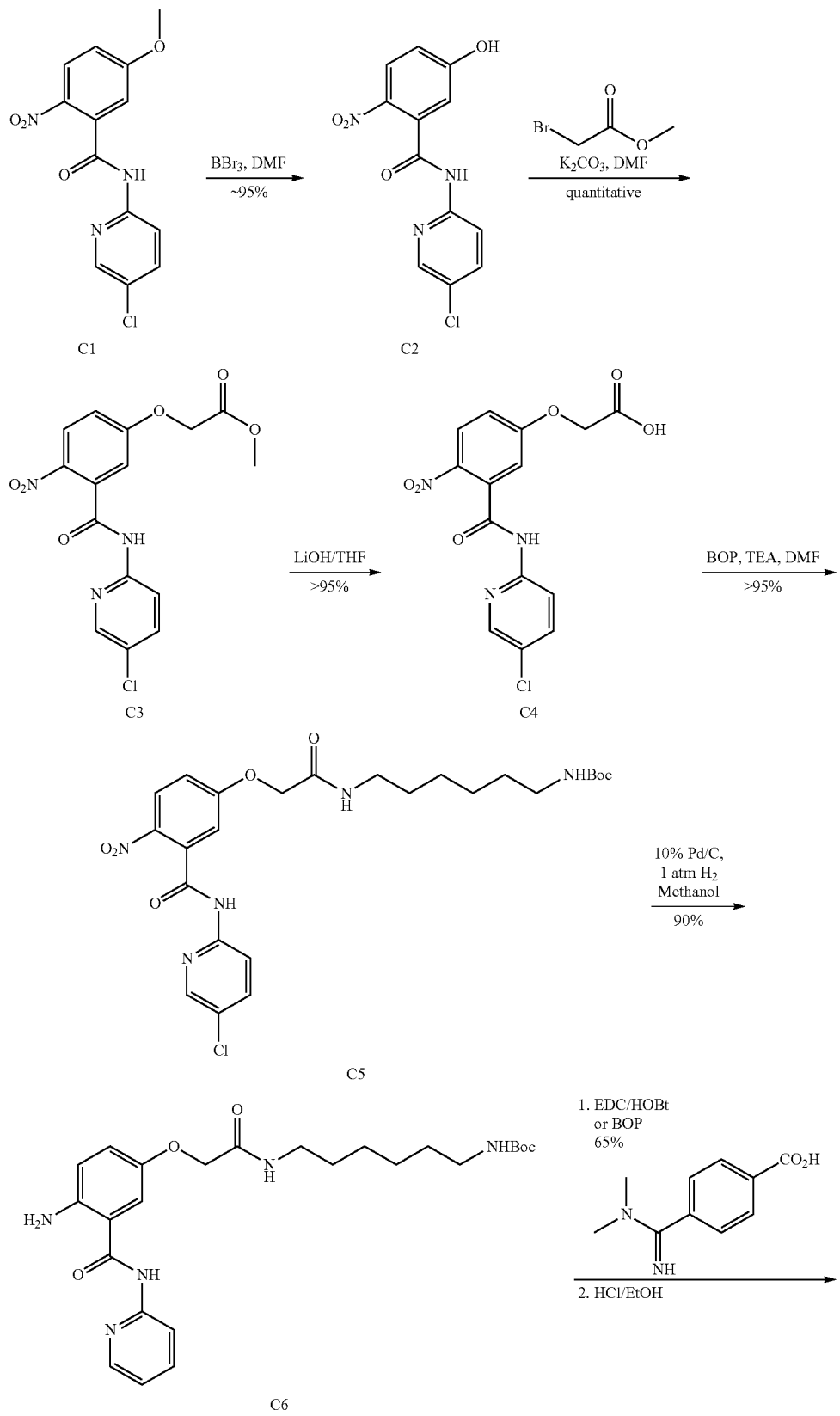

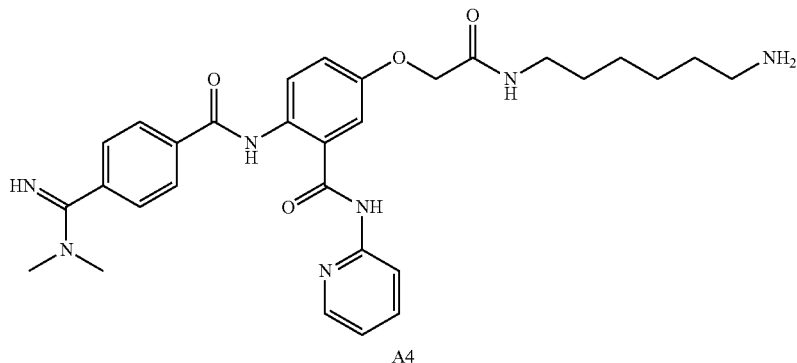

A4

To a dichloromethane solution of 5-methoxy-2-nitro-N-(5-chloro-pyridine-2-yl)benzamide (C1, 2 g, 6.5 mmol) was added BBr$_3$ (1.5 mL, 15.6 mmol). The reaction mixture was stirred at room temperature overnight. To the reaction mixture was added water, the solid precipitated was collected by filtration, dried under vacuum to afford compound C2 (1.8 g).

Compound C2 and methyl 2-bromoacetate (1 g, 3.4 mmol) was dissolved in DMF (20 mL) followed by addition of K$_2$CO$_3$ (94 mg, 6.8 mmol) and the reaction mixture was heated at 40° C. After 1 hour stirring, the reaction was complete. Water was added and the mixture was extracted with ethyl acetate. The ethyl acetate layer was dried, filtered and evaporated to afford compound C3 (1.59 g). The crude residue was purified by RP-HPLC. ESCI-MS: 366.1 & 368.1 (chlorine pattern).

To a THF solution of compound C3 (1.5 g, 4.3 mmol) was added LiOH (1 M aqueous, 17.2 mL, 17.2 mmol) and the reaction was stirred at room temperature for 1 hour. The progress of the reaction was monitored by HPLC and after 1 hour, the reaction showed complete disappearance of compound C3. The reaction mixture was concentrated, added water and acidified with 1N HCl. The solid precipitated was collected to give compound C4 (480 mg). ESMS: M+H=352.1, 354.1 (Cl pattern).

Compound C4 (480 mg, 1.7 mmol), BOP (757 mg, 1.7 mmol) and triethylamine (392 µL, 1.7 mmol) were dissolved in 10 mL of DMF and stirred at room temperature for 30 mins. To the mixture added Boc protected C$_6$ linked diamine (380 µL, 1.7 mmol) and the reaction mixture was stirred for 30 mins. The product compound C5 was isolated with ethyl acetate after aqueous work-up. ESMS: 550 & 552 (Cl pattern) and M-Boc=450.2.

Compound C5 was suspended in ethyl acetate and added 10% Pd/C. The mixture was hydrogenated with H$_2$ balloon overnight. The reaction mixture was filtered through celite and the filtrate was evaporated to afford the desired compound C6. ESMS confirmed M+H=486.4 (No Cl pattern).

Compound C6, BOP (1.1 eq.) and DMAP (1.2 eq.) were dissolved in DMF and stirred for 1 hour at room temperature. To the mixture was added 4-(N,N-dimethylcarbamimidoyl)benzoic acid (1.05 eq.) and reaction mixture was stirred overnight. To the reaction mixture was added water and the crude product was extracted with ethyl acetate. The residue was dissolved in ethanol followed by addition of 6 N HCl. The product crashed out. The solid was filtered to give the title compound. ESMS confirms M+H=561.

Route 4:

Compound A4 was also prepared according to:

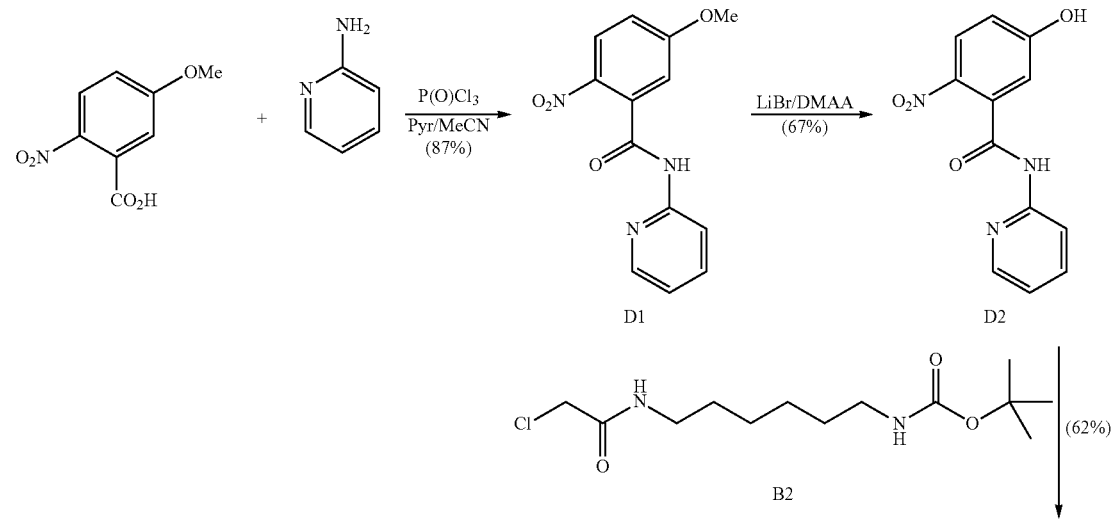

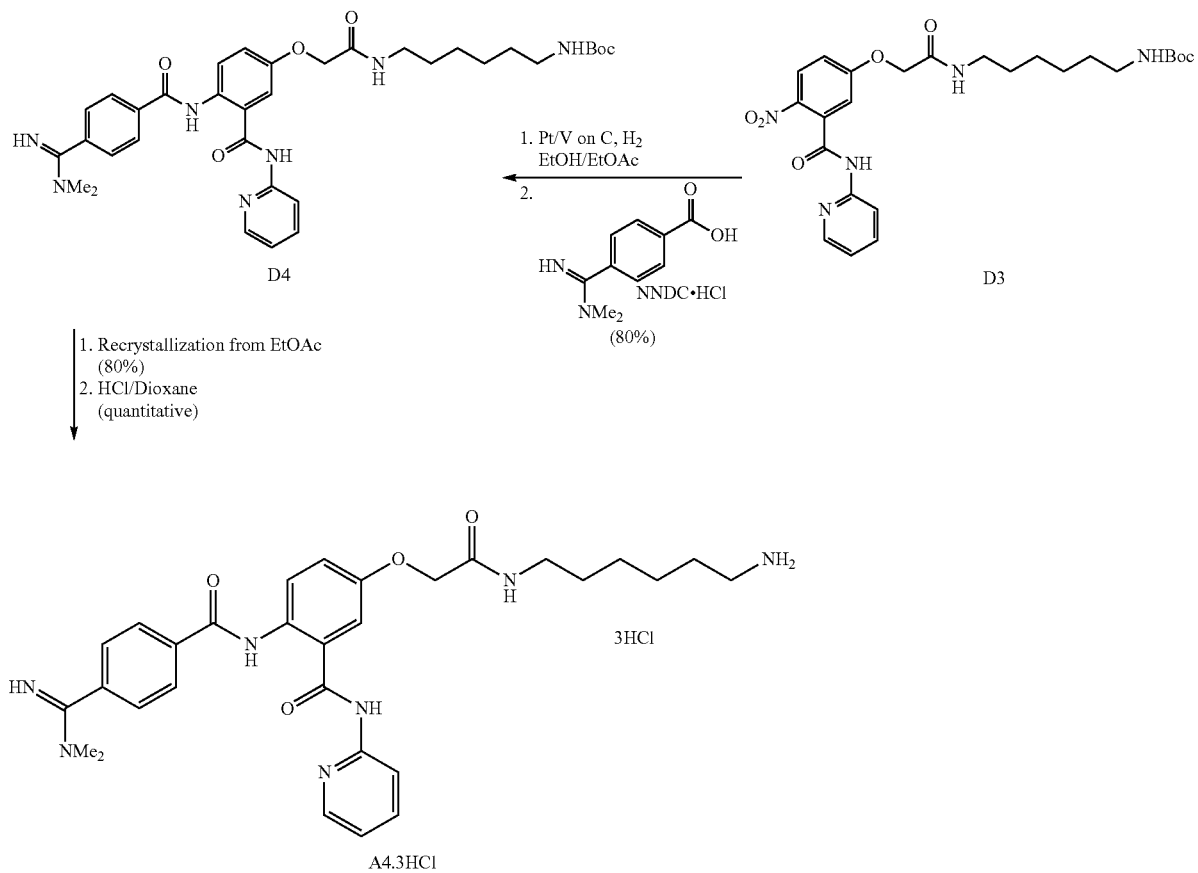

To a 250 mL flask was charged 5-methoxy-2-nitrobenzoic acid (100 g, 507 mmol), 2-aminopyridine (71.6 g, 761 mmol, 1.5 eq.), acetonitrile (550 mL), then pyridine (120 g, 1520 mmol, 3.0 eq.) and the mixture was stirred and cooled to 0-5° C. under nitrogen. Then $POCl_3$ (93 g, 609 mmol, 1.2 eq.) was added drop-wise over about 60 minutes, keeping the temperature below 5° C. Upon reaction completion (about 1 hour, based on HPLC) the reaction mixture was quenched by slow addition of water (750 mL). The resulting solids went into solution in a few minutes, but precipitated out upon addition of KOH. After stirring overnight the organics were removed from the sticky solid by distillation, water (1000 mL) was added and the mixture was stirred at 0-5° C. for 30 minutes, then collected by filtration. The product was dried under vacuum to provide 121 g of D1 that was 95.4% pure by HPLC.

To 2.235 kg of Compound D1 (8.18 mole) in DMAc (19.0 kg; 20.3 L) was added LiBr (6.64 kg, 76.5 mole) and the mixture was stirred at 147° C. for about 20 hours. The product was isolated by filtration, dried first under nitrogen then finished in a vacuum drying oven to provide a total of 1425 g of Compound D2 that was 98.1% pure (with 1.9% D1 as only measurable impurity).

To 1.810 kg (6.98 mole) of Compound D2 and 1.348 kg (4.60 mole) of Compound B2 in DMAc (20 L) were added 2.431 kg of $K_2PO_4$. After 45 hours at 84-86° C., the mixture was cooled, quenched into water and subjected to an aqueous work up followed by crystallization from EtOAc/heptane. After drying under vacuum a total of 1481 g of Compound D3 was obtained with HPLC purity of 98.7%.

250 g Compound D3 was reduced with $H_2$ in EtOH/EtOAc with Pt/V on C at 35 psi and 38° C. to provide an intermediate that is not isolated but carried directly on to the coupling with NNDC.HCl (150.0 g, 1.35 eq.) using EDAC (138 g, 1.5 eq) as the coupling reagent in DMAc. Compound D4 was isolated by quenching the reaction mixture into aqueous $Na_2CO_3$/$NaHCO_3$ with a small amount of MTBE present to prevent Compound D4 from becoming a sticky mass. After filtration, washing with water and MTBE, and vacuum drying a total of 291 g of Compound D4 was obtained as a bright yellow solid with HPLC purity of 96.7%.

A total of 2068 g (1491 g) of crude Compound D4 was charged to a 50 L reactor and heated with 30 L of EtOAc to 70° C. The slurry was then filtered into a clean reactor, heptane was added slowly (6 L), and the mixture slowly cooled to ambient temperature for an overnight stir period. The product was isolated by filtration and dried under nitrogen to provide 1113.6 g of purified Compound D4 was obtained with HPLC purity of 98.6% (AUC).

A total of 1.179 kg of purified Compound D4 was dissolved in 27.8 L 1,4-dioxane and treated with 2.89 kg of a solution of 4M HCl in 1,4-dioxane. After stirring at 13° C. for 20 hours, an additional 0.23 kg of 4M HCl in dioxane was charged and after an additional overnight stir period the reaction was complete. The product was filtered and dried under a nitrogen purge for 6 days under vacuum oven to finish 1,4-dioxane removal. A total of 1195 g of Compound A4 (3HCl salt) was obtained after vacuum drying to remove 1,4-dioxane.

Example 3

Preparation of 5-(2-((6-aminopentyl)amino)-2-oxo-ethyoxy)-N-(5-chloropyridin-2-yl)-2-(4-(N,N-dimethylcarbamimidoyl)benzamido)benzamide

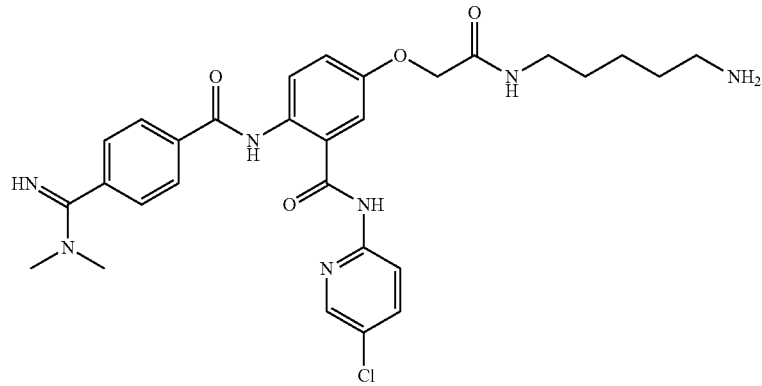 [SMILES: CN(C)C(=N)c1ccc(C(=O)Nc2ccc(OCC(=O)NCCCCCN)cc2C(=O)Nc2ccc(Cl)cn2)cc1]

The title compound was prepared according to a procedure similar to that illustrated in Example 1 using tert-butyl (5-(2-chloroacetamido)pentyl)carbamate. MS found for $C_{29}H_{34}ClN_7O_4$ as $(M+H)^+$584.6. UV: $\lambda$=202, 287.8 nm.

Example 4

Preparation of 5-(2-((6-aminopropyl)-2-oxoethyoxy)-N-(5-chloropyridin-2-yl)-2-(4-(N,N-dimethylcarbamimidoyl)benzamido)benzamide

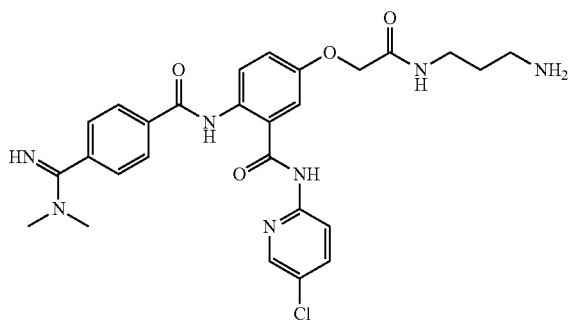 [SMILES: CN(C)C(=N)c1ccc(C(=O)Nc2ccc(OCC(=O)NCCCN)cc2C(=O)Nc2ccc(Cl)cn2)cc1]

The title compound was prepared according to a procedure similar to that illustrated in Example 1 using tert-butyl (5-(2-chloropropyl)carbamate. MS found for $C_{27}H_{30}ClN_7O_4$ as $(M+H)^+$552.21. UV: $\lambda$=202, 287.8 nm.

Example 5

Preparation of 5-(2-((4-aminobutyl)amino)-2-oxo-ethyoxy)-N-(5-chloropyridin-2-yl)-2-(4-(N,N-dimethylcarbamimidoyl)benzamido)benzamide

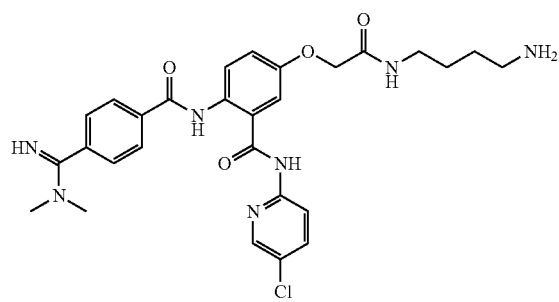 [SMILES: CN(C)C(=N)c1ccc(C(=O)Nc2ccc(OCC(=O)NCCCCN)cc2C(=O)Nc2ccc(Cl)cn2)cc1]

The title compound was prepared according to a procedure similar to that illustrated in Example 1 using tert-butyl (5-(2-chlorobutyl)carbamate. MS found for $C_{28}H_{32}ClN_7O_4$ as $(M+H)^+$566.22. UV: $\lambda$=202, 287.8 nm.

Example 6

Preparation of 5-(4-aminobutoxy)-2-(4-(N,N-dimethylcarbamimidoyl)benzamido)-N-(pyridin-2-yl)benzamide

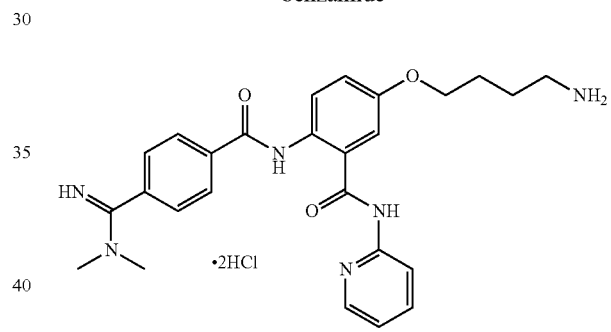

The title compound was prepared according to a procedure similar to that illustrated in Example 2, route 4, starting with Compound D2. MS found for $C_{26}H_{30}N_6O_3$ as $(M+H)^+$ 475.3.

Example 7

5-((6-aminohexyl)oxy)-2-(4-(N,N-dimethylcarbamimidoyl)benzamido)-N-(pyridin-2-yl)benzamide

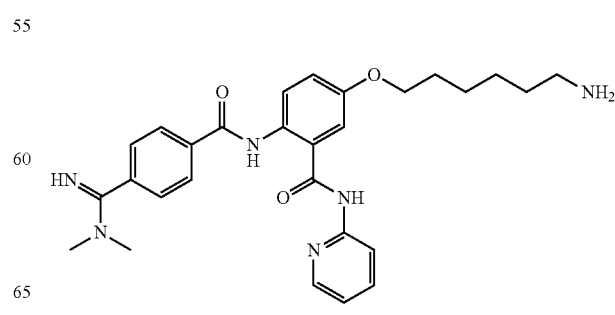

The title compound was prepared according to a procedure similar to that illustrated in Example 2, route 4, starting with Compound D2. MS found for $C_{28}H_{34}N_6O_3$ as $(M+H)^+$ 503.3.

Example 8

5-(2-((3-aminopropyl)amino)-2-oxoethoxy)-2-(4-(N, N-dimethylcarbamimidoyl)benzamido)-N-(pyridin-2-yl)benzamide

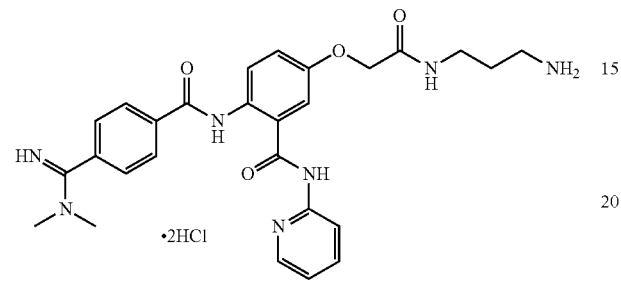

The title compound was prepared according to a procedure similar to that illustrated in Example 2, route 4, starting with Compound D2. MS found $C_{27}H_{31}N_7O_4$ as $(M+H)^+$ 518.3.

Example 9

$N^1$-(4-aminobutyl)-$N^4$-(4-methoxy-2-(pyridin-2-ylcarbamoyl)phenyl)terephthalamide

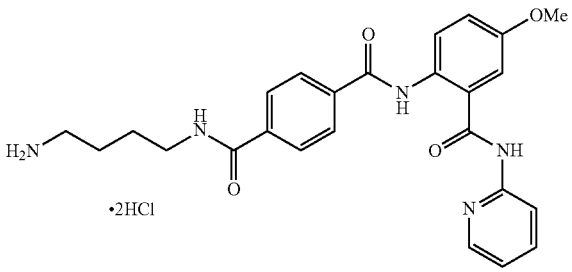 [SMILES: COc1ccc(NC(=O)c2ccc(C(=O)NCCCCN)cc2)c(C(=O)Nc2ccccn2)c1]

The title compound was prepared according to the following procedure starting with Compound D1 in Example 2, route 4.

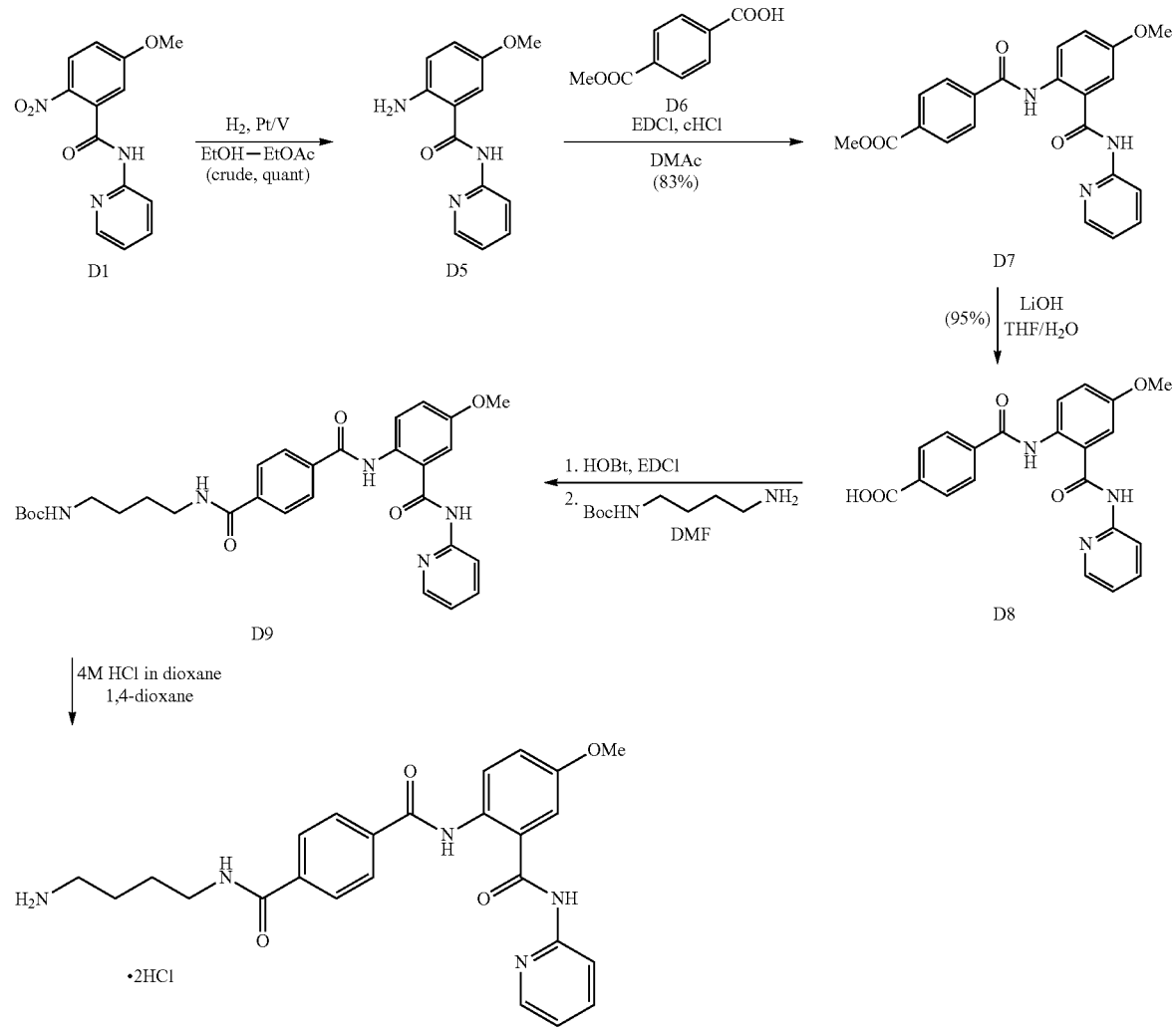

Compound D1 (2.73 g, 10 mmol) was charged in a pressure bottle. Ethanol (15 mL) and ethyl acetate (7 mL) were added, and the resulting slurry was degassed and purged nitrogen. Then platinum/vanadium on carbon (0.27 g) was added. The reaction mixture was degassed and purged hydrogen (40 psi) and was heated at 40° C. After stirring at 40° C. under hydrogen atmosphere (40 psi) for 3 h, HPLC and TLC indicated the reaction completion. Upon the completion, the catalyst was removed by filtration through a Celite pad and washed with ethyl acetate. The filtrate was concentrated under reduced pressure. The residual oil was dried under vacuum to isolate 2.56 g of crude Compound D5 as a yellow thick oil, which solidified over the time (quantitative).

Compound D5 (0.5 g, 2.06 mmol) was dissolved in DMAc (6 mL) and put under reduced pressure at 45° C. (water bath) to remove any residual solvent from the previous step. The solution was placed in a flask. Compound D6 (0.47 g, 2.61 mmol) was added, followed by the addition of conc HCl (11 µL, 0.13 mmol). The resulting solution was cooled down to 15° C. EDCI (0.55 g, 2.88 mmol) was divided into four portions and was added every 20 min at 15±2° C. HPLC confirmed the reaction completion in 30 min after the last addition of EDCI and the reaction was quenched by pouring into a solution of sodium carbonate (0.3 g) and sodium bicarbonate (0.17 g) in water (6.5 mL) and MTBE (1.5 mL). The quench was slightly exothermic and the internal temperature was up to 30° C. During the quench, a yellow precipitate was formed. The resulting yellow slurry was stirred at 0° C. for 1 h and the precipitate was isolated by filtration, washed with water and MTBE, and dried in the vacuum oven at 35-40° C. overnight to afford 1.5 g of crude Compound D7 as a pale yellow solid with the purity of 90%. Thus, the further purification was performed before the hydrolysis step. The solid was suspended in MTBE (25 mL) and stirred at ambient temperature for 1 h to remove some of the impurities. The purity was improved to 96%. To achieve higher purity, a recrystallization from isopropanol was carried out. First, 100 mg of the solid was recrystallized from isopropanol (5 mL) and 83 mg of Compound D7 was isolated in 98.5% purity (83% recovery). The rest of the solid was recrystallized from isopropanol (45 mL) to isolate 455 mg of Compound D7 (97.8% purity) (total 0.54 g, 64% yield, 98% purity).

A solution of lithium hydroxide (36 mg, 0.75 mmol) in water (0.6 mL) was added to a solution of Compound D7 (100 mg, 0.25 mmol) in THF (3.6 mL) at ambient temperature. The reaction mixture was stirred at ambient temperature for 4 h. The reaction was monitored by HPLC which showed 96% of Compound D8 and 4% of Compound D7. The reaction was quenched with water and the desired compound D8 was extracted in ethyl acetate.

Compound D8 (0.5 g, 1.278 mmol) was suspended in DMF (10 mL) and was put under reduced pressure to remove any residual solvent from the previous step. Then the slurry was diluted with DMF (40 mL) and HOBt (0.26 g, 1.92 mmol) was added. The mixture was stirred at ambient temperature and was added EDCI (0.29 g, 1.534 mmol) at once. The resulting pale brown slurry was stirred at ambient temperature. After overnight the reaction mixture became pale brown slightly unclear solution. A solution of N-Boc-1,4-butanediamine (0.36 g, 1.916 mmol) in DMF (2.5 mL) was added drop-wise at ambient temperature. DMF (2.5 mL) was used to rinse. After 4 h, the reaction mixture was diluted with ethyl acetate (200 mL) and hexanes (5 mL). The solution was washed with water (30 mL×3). The aqueous layers were combined and extracted with ethyl acetate/hexanes (20/1, 100 mL). The organic layers were combined, washed with 1N HCl solution (30 mL), water (30 mL), saturated sodium bicarbonate solution (30 mL), saturated sodium chloride solution (30 mL), and dried over sodium sulfate. The solid was removed by filtration and washed with ethyl acetate. The filtrate was concentrated under reduced pressure. The crude solid (1.34 g) was purified by recrystallization from ethyl acetate (~50 mL) and heptanes (10~15 mL). The obtained slurry was cooled down to 0° C. by an ice-water bath and stirred for 2 h and the precipitate was isolated by filtration, washed with ethyl acetate/heptanes (3/1, ~150 mL total), and dried in the vacuum oven at 40-45° C. for 2-3 h. 451 mg of Compound D9 as a white solid (63%, >99% purity).

Compound D9 (300 mg, 0.534 mmol) was dissolved in 1,4-dioxane (60 mL), along with methanol (20 ml) and 4M HCl solution in 1,4-dioxane (4 mL, 16 mmol) was added drop-wise at ambient temperature. The reaction mixture was stirred overnight. The reaction mixture was monitored by HPLC, and the reaction completion was observed after 24 h at ambient temperature. The precipitate was isolated by filtration, washed with MTBE several times, and dried in the vacuum oven at 40-45° C. for 3 h to isolate 241 mg of title compound as a yellow solid (84.4%, >99% purity). MS found for $C_{25}H_{27}N_5O_4$ as $(M+H)^+462.2$.

Example 10

$N^1$-(3-aminopropyl)-$N^4$-(4-methoxy-2-(pyridin-2-ylcarbamoyl)phenyl)terephthalamide

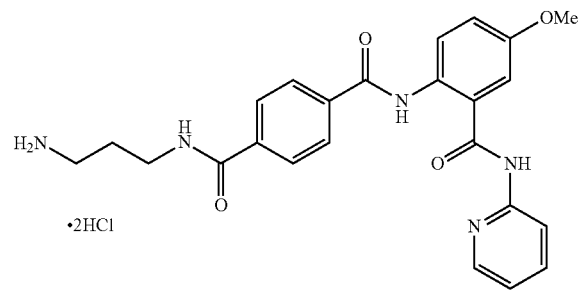 [SMILES: COc1ccc(NC(=O)c2ccc(C(=O)NCCCN)cc2)c(C(=O)Nc2ccccn2)c1]

The title compound was prepared according to a procedure similar to that illustrated in Example 9 and isolated as yellow solid (HPLC>99% purity). MS found for $C_{24}H_{26}N_5O_4$ as $(M+H)^+448.2$.

Example 11

$N^1$-(6-aminohexyl)-$N^4$-(4-methoxy-2-(pyridin-2-ylcarbamoyl)phenyl)terephthalamide

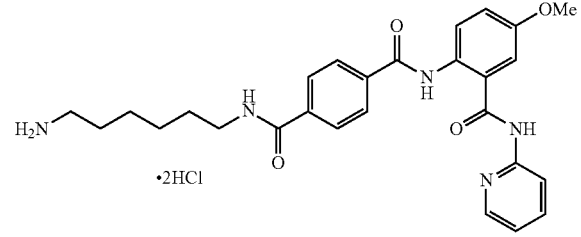 [SMILES: COc1ccc(NC(=O)c2ccc(C(=O)NCCCCCCN)cc2)c(C(=O)Nc2ccccn2)c1]

The title compound was prepared according to a procedure similar to that illustrated in Example 9. MS found for $C_{27}H_{31}N_5O_4$ as $(M+H)^+$ 490.2.

Example 12

2-(4-(4-aminobutoxy)benzamido)-5-methoxy-N-(pyridin-2-yl)benzamide

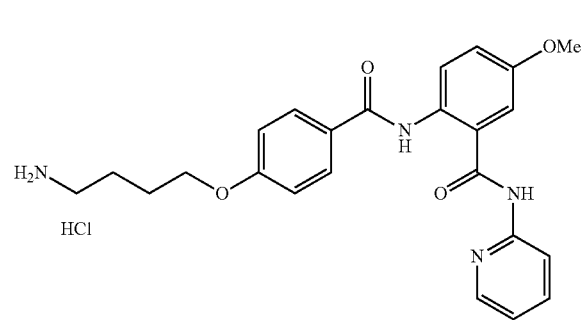 [SMILES: COc1ccc(NC(=O)c2ccc(OCCCCN)cc2)c(C(=O)Nc2ccccn2)c1 ; Cl]

The title compound was prepared according to the following procedure starting with methyl 4-hydroxy benzoate.

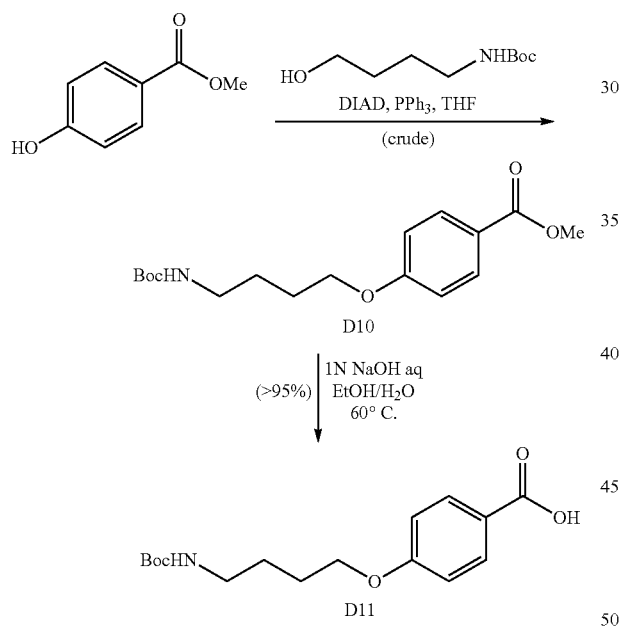

Methyl 4-hydroxybenzoate (76 mg, 0.5 mmol), 4-(Boc-amino)-1-butanol (114 mg, 0.6 mmol), and triphenylphosphine (197 mg, 0.75 mmol) were dissolved in THF (anhyd, 2 mL) and cooled down to ~5° C. DIAD (0.15 mL, 0.75 mmol) was added drop-wise. The addition was exothermic and the internal temperature was up to ~10° C. After the addition, the reaction mixture was warmed up to ambient temperature and stirred for 1 h. The reaction mixture was diluted with hexanes/ethyl acetate (2/1, v/v), the organic layer was washed with 1N NaOH solution, water×2 (neutral), saturated sodium chloride solution, and dried over sodium sulfate. The solid was removed by filtration through a short pad of silica gel and concentrated under reduced pressure to provide 0.32 g of D10 as a yellow oil.

To the crude D10 were added 1N NaOH solution and ethanol and the reaction mixture was stirred at ambient temperature overnight, and then heated at 50° C. The reaction mixture was washed with ethyl acetate. The aqueous layer was acidified with 10% $KHSO_4$ solution to pH-2 and extracted with ethyl acetate. The organic layer was separated, washed with water (2×), saturated sodium chloride solution, and dried over sodium sulfate. The solid was removed and the filtrate was concentrated under reduced pressure to yield 152 mg of Compound D11 as a white solid (98% over two steps).

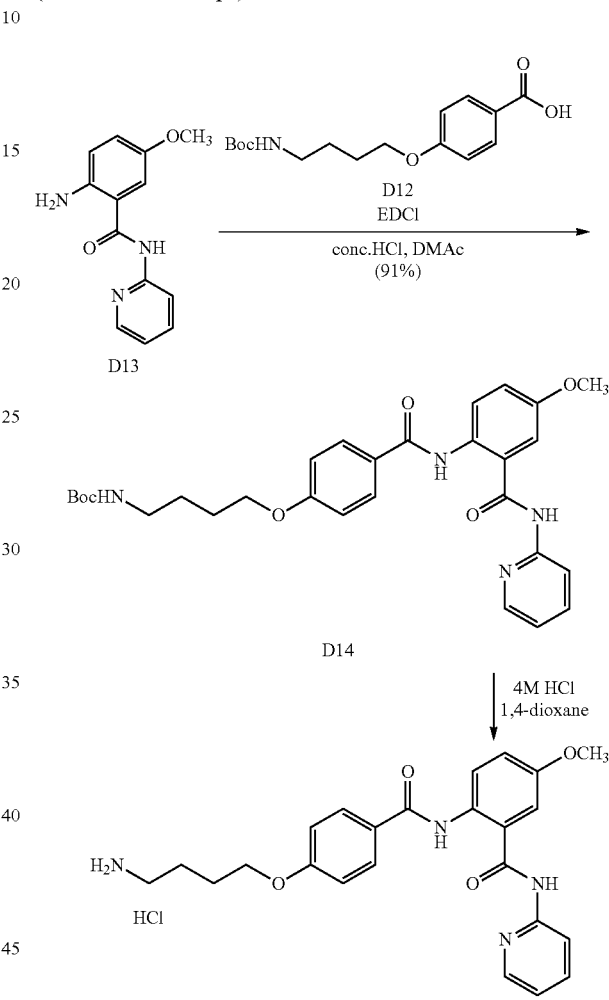

Amine D13 (0.25 g, 1.03 mmol) and acid D11 (0.41 g, 1.31 mmol) were dissolved in DMAc (5 mL) and put under reduced pressure to remove any residual solvent from the previous step (at ~50° C., ~10 mmHg, for 30 min). The solution was diluted with DMAc (10 mL), and was added conc HCl (6 μL, 0.065 mmol). The solution was cooled down to ~5° C. and was added ¼ of EDCI (0.28 g, 1.44 mmol) in every 15 min. After the last addition, the reaction mixture was warmed up to ambient temperature. Upon completion, the reaction mixture was poured into a solution of sodium carbonate (0.17 g) and sodium bicarbonate (0.1 g) in water (5 mL). The precipitate was generated, but became gummy oil by the addition of excess water. Thus, the aqueous layer was extracted with ethyl acetate. The organic layer was separated, washed with water until neutral, saturated sodium chloride solution, and dried over sodium sulfate. The solid was removed and the filtrate was concentrated under reduced pressure to isolate 0.97 g of pale brown crude oil which was solidified in a mixture of ethyl acetate (2.5 mL) and hexanes (5 ml). After drying under vacuum, 0.5 g of compound D13 was obtained (91%).

Compound D13 (0.25 g, 0.47 mmol) was dissolved in 1,4-dioxane (25 mL) by slight heating (~45° C.). The solution was cooled down to ambient temperature, and was added 4M HCl solution in 1,4-dioxane (1.75 mL, 7.01 mmol) drop-wise. After 1 h, methanol (3 mL) was added. After 17 h, an additional amount of 4M HCl solution was added (0.5 mL, 2 mmol) and the reaction mixture was stirred for another 3 h. The reaction mixture was diluted with MTBE and the solid was isolated, washed with MTBE, and dried in the vacuum oven at 40-45° C. for overnight to isolate 172 mg of the title compound as a yellow-orange solid in 71% (99% purity). MS found for $C_{24}H_{26}N_4O_4$ as $(M+H)^+$ 435.2.

Example 13

FXa Inhibitory Activity of Compounds

This example illustrates methods for evaluating the compounds, along with results obtained for such assays. As mentioned above, the compound may be selected based on its factor Xa inhibitory activity. The in vitro factor Xa activities of the compounds can be determined by various procedures known in the art. The potent affinities for factor Xa inhibition exhibited by the compounds can be measured by an $IC_{50}$ value (in nM). The $IC_{50}$ value is the concentration (in nM) of the compound required to provide 50% inhibition of factor Xa proteolytic activity. The smaller the $IC_{50}$ value, the more active (potent) is a compound for inhibiting factor Xa activity.

An in vitro assay for detecting and measuring inhibition activity against factor Xa is as follows:

a. $IC_{50}$ and Ki Determinations

Substrate:

The substrate S-2765 (Z-D-Arg-Gly-Arg-pNA.HCl) can be obtained from Diapharma (West Chester, Ohio).

Enzyme:

The human plasma protein factor Xa can be purchased from Haematologic Technologies (Essex Junction, Vt.).

Methods:

$IC_{50}$ Determinations

All assays, which are performed in 96-well microtiter plates, measure proteolytic activity of the enzyme (factor Xa) by following cleavage of a paranitroanilide peptide substrate. The assay buffer used for proteolytic assays was Tris buffered saline (20 mM Tris, 150 mM NaCl, 5 mM $CaCl_2$, 0.1% Bovine serum albumin (BSA), 5% dimethly sulfoxide (DMSO) pH 7.4). In a 96-well microtiter plate, inhibitor was serially diluted to give a range of final concentrations from 0.01 nM to 10 µM. Duplicate sets of wells were assayed and control wells without inhibitor were included. Enzyme was added to each well, (factor Xa concentration=1 nM), the plate was shaken for 5 seconds and then incubated for 5 minutes at room temperature. 52765 was added (100 µM final) and the plate was shaken for 5 seconds (final volume in each well was 200 µL). The degree of substrate hydrolysis was measured at 405 nm on a Thermomax plate reader (Molecular Devices, Sunnyvale, Calif.) for 2 minutes. The initial velocities of substrate cleavage (mOD/min), for each range of inhibitor concentrations, were fitted to a four parameter equation using Softmax data analysis software. The parameter C, derived from the resulting curve-fit, corresponded to the concentration for half maximal inhibition ($IC_{50}$).

$K_i$ Determination

The assay buffer for this series of assays was Hepes buffered saline (20 mM Hepes, 150 mM NaCl, 5 mM $CaCl_2$, 0.1% PEG-8000, pH 7.4). In a 96-well microtiter plate, inhibitor was serially diluted in a duplicate set of wells to give a range of final concentrations from 5 µM to 3 µM. Controls without inhibitor (8 wells) were included. The enzyme, factor Xa (final concentration=1 nM) was added to the wells. The substrate S-2765 (final concentration=200 µM) was added and the degree of substrate hydrolysis was measured at 405 nm on a Thermomax plate reader for 5 minutes, using Softmax software. Initial velocities (mOD/min) were analyzed by non-linear least squares regression in the Plate $K_i$ software (BioKin Ltd, Pullman, Wash.) [Kusmic, et al., *Analytical Biochemistry* 281: 62-67, 2000]. The model used for fitting the inhibitor dose-response curves was the Morrison equation. An apparent $K_i$(Ki*) was determined. The overall $K_i$ was calculated using the following equation:

$$Ki = \frac{Ki^*}{1 + \frac{[S]}{Km}}$$

where [S] is substrate concentration (200 µM) and $K_m$, the Michaelis constant for S2765.

Table 4 shows the fXa inhibitory activity of selected compounds.

TABLE 4

| Compound | fXa IC$_{50}$ (nM) |
|---|---|
|  | 227 |

TABLE 4-continued
| Compound | fXa IC$_{50}$ (nM) |
|---|---|
| 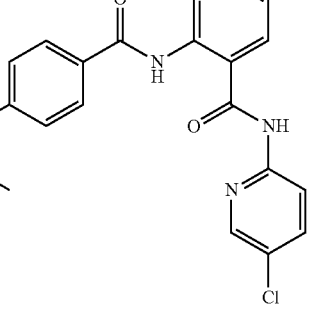 | 24 |
| 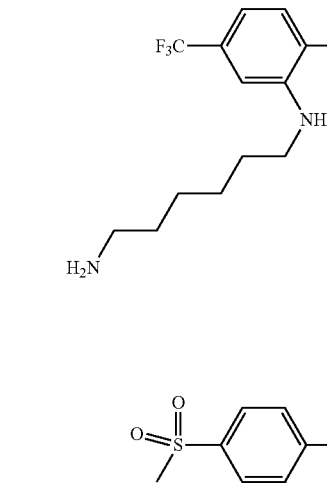 | 615 |
| 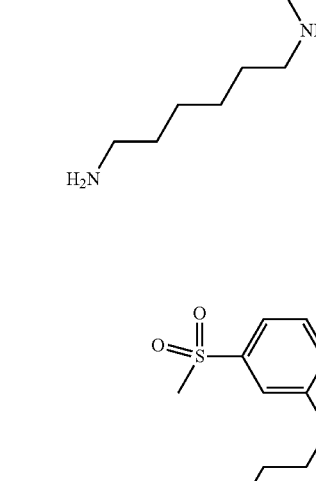 | 158 |
| 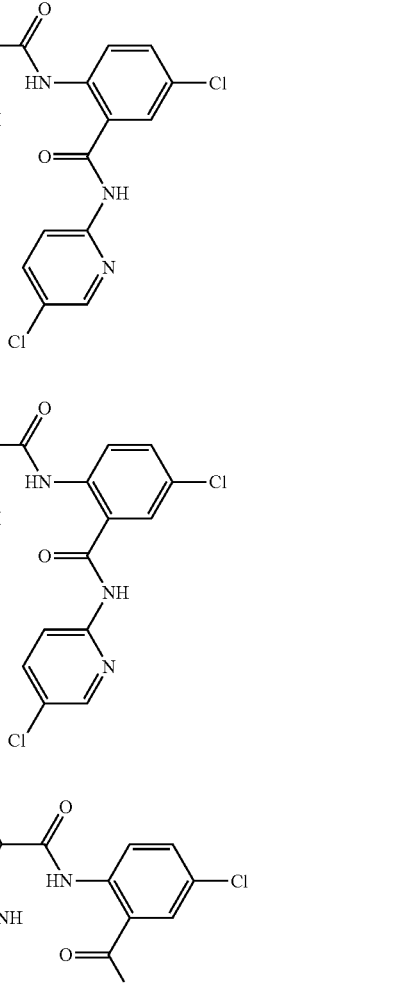 | 320 |

Example 14

Preparation of Affinity Resin with Betrixaban Ligand A3 for the Purification of r-Antidote 1. Coupling of compound A3 to CNBr-activated Sepharose 4 Fast Flow Matrix

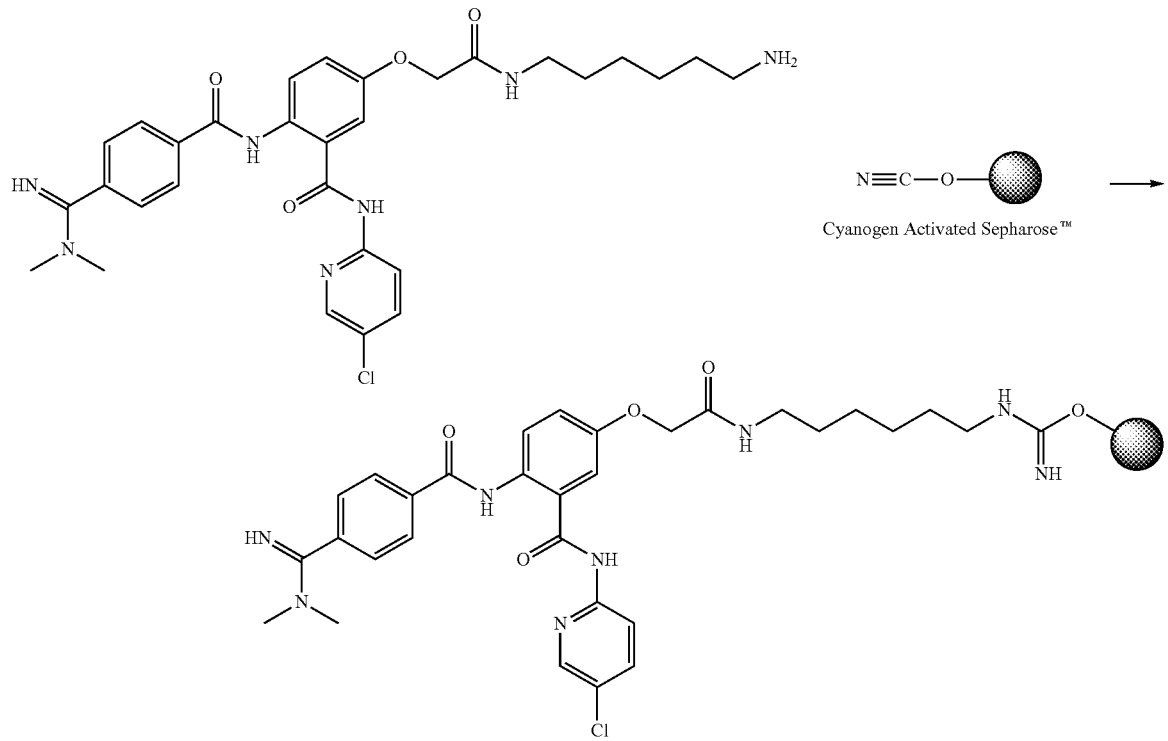

CNBr-activated Sepharose 4-FF matrix was hydrated with 1 mM HCl. The resin was washed 10 times with 2 mL volumes of 1 mM HCl. After this step, 20 mL of resin was obtained. The coupling solution was prepared by dissolving Compound A3 (150 mg) in 2.5 mL of DMSO. This solution was diluted to 5.0 mL with a buffer containing 0.1M NaHCO$_3$ and 0.5 M NaCl at pH 8.3. The coupling solution was added to 10 mL of resin and reacted for room temperature for 3 hours while adjusting the pH to about 8.3. The reaction was monitored by UPLC after completion of the coupling, unreacted CNBr was capped with 0.1 M Tris-HCl buffer at pH 8.0. The coupled resin was washed three times with 0.1 M acetate buffer pH 3 to 4 containing 0.5 M NaCl, and then with 0.1M Tris-HCl buffer pH 8 to 9 containing 0.5 M NaCl. The above wash cycle was repeated five times. The coupled ligand affinity resin is available for r-antidote purification.

CNBr-activated Sepharose 4 Fast Flow is a pre-activated matrix that combines the advantages of CNBr coupling with the high flow stability characteristics of Sepharose 4 Fast Flow.

2. Coupling of Compound A4 to CNBr-Activated Sepharose 4 Fast Flow Matrix

A similar procedure was utilized to couple Compound A4 to CNBr-activated Sepharose 4-FF resin to prepare affinity resin with des-chloro betrixaban Compound A4.

Example 15

Coupling of Betrixaban with NHS Activated Resin

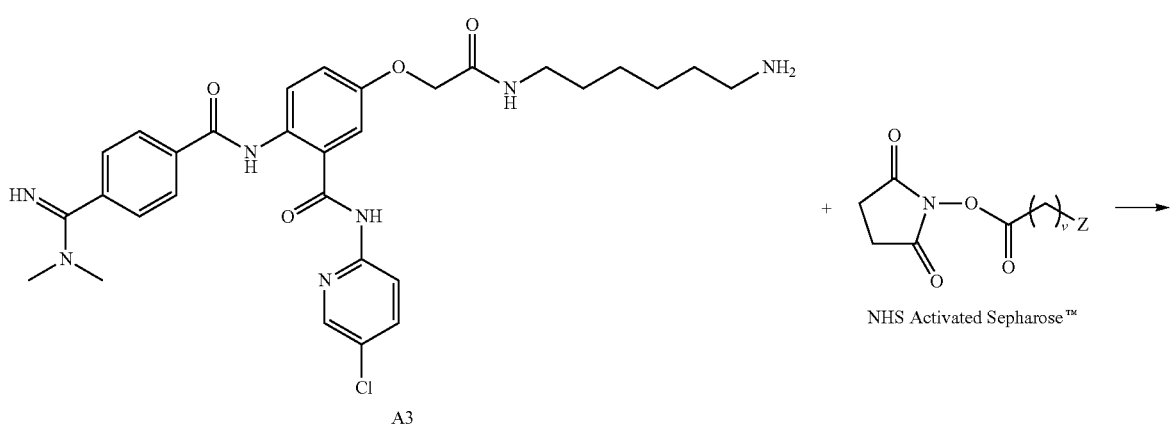

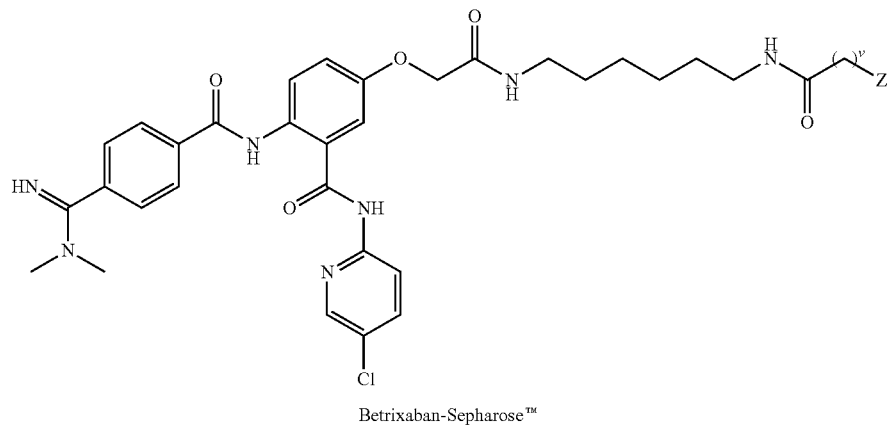

Betrixaban-Sepharose™

NHS-activated Sepharose 4-FF matrix was hydrated with 1 mM HCl. The resin was washed 10 times with 2 mL volumes of 1 mM HCl. After this step, 20 mL of resin was obtained. The coupling solution was prepared by dissolving Compound A3 (15 mg) in 0.5 mL of DMSO. This solution was diluted to 3.0 mL with buffer containing 0.1 M NaHCO$_3$, 0.5 M NaCl at pH 8.3. This coupling solution was added to the NHS-activated Sepharose matrix and reacted at room temperature for 3 hours while adjusting the pH at about 8.3. The reaction was monitored by UPLC. After completion of the coupling, unreacted resin was blocked with 0.1 M Tris-HCl buffer at pH 8.0. The coupled betrixaban NHS-Sepharose resin was washed with 3 times with 0.1M acetate buffer pH 3 to 4 containing 0.5 M NaCl and 0.1 M Tris-HCl buffer pH 8 to 9 containing 0.5 M NaCl. 5 mL of des-chloro-betrixaban NHS-Sepharose resin was obtained using a similar procedure. The substitution is 3 mg of compound per mL of resin or 5 μmol compound per mL of resin. The coupled ligand affinity resin is available for r-antidote purification.

Other ligand affinity NHS resins can be prepared similarly, for example:

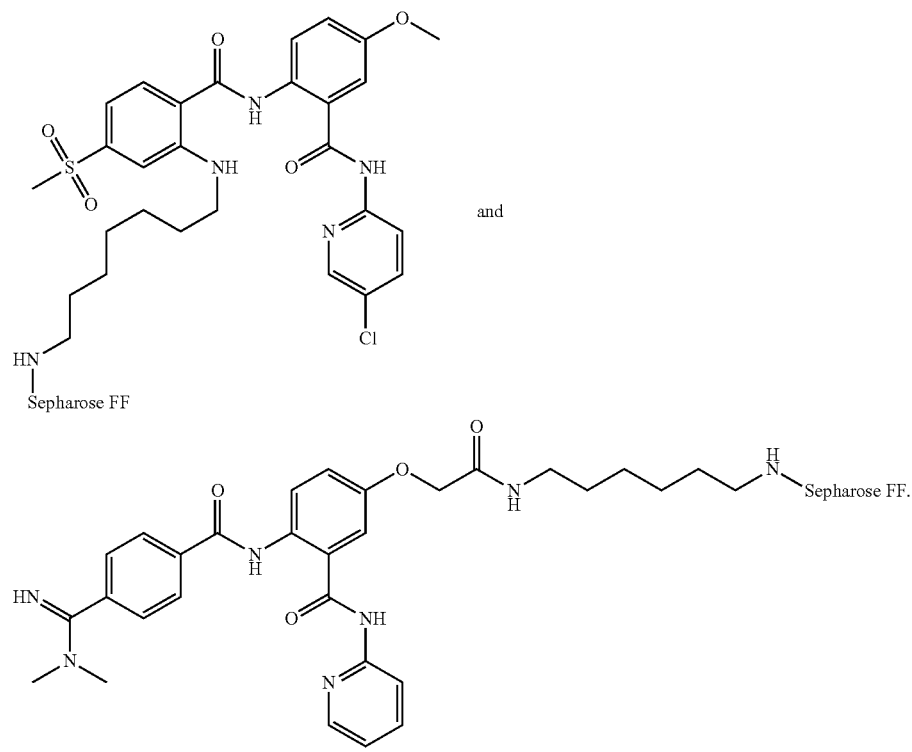

Example 16
Coupling of Betrixaban with EAH Sepharose™ Resin
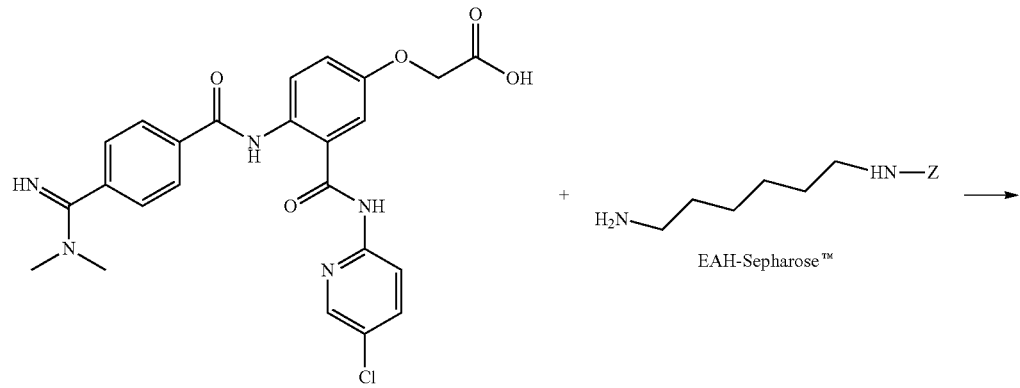
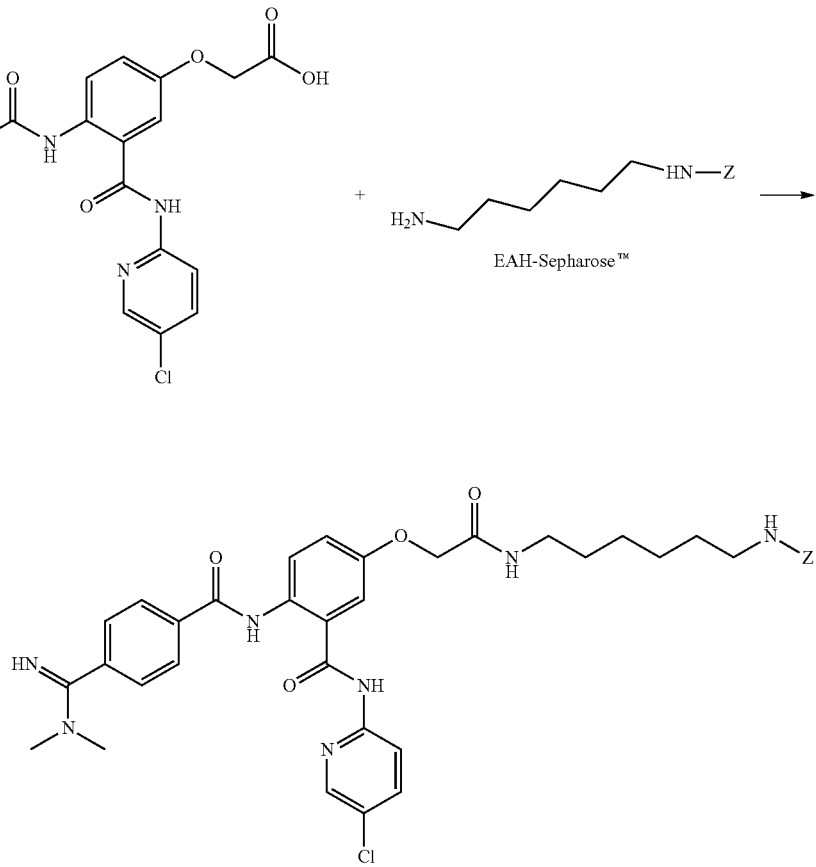
Coupling of betrixaban with EAH Sepharose™ resin can be conducted according to methods described in Instructions 71-7097-00 AE, 2009, by General Electric Company.
Example 17
Coupling of Des Chloro-C6 Betrixaban Linker A4 with NHS Activated Capto Resin
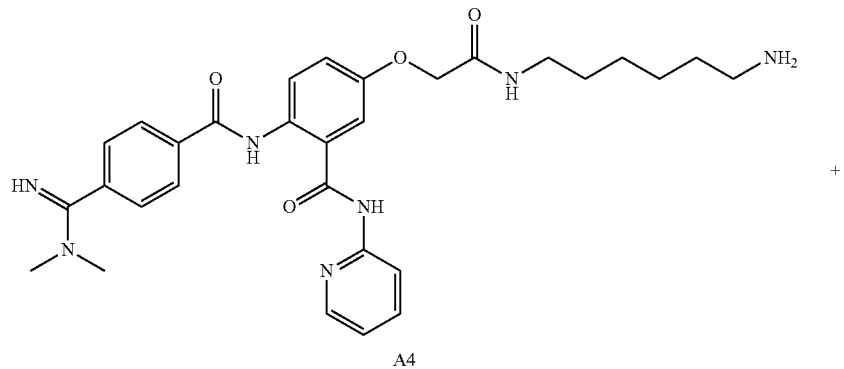

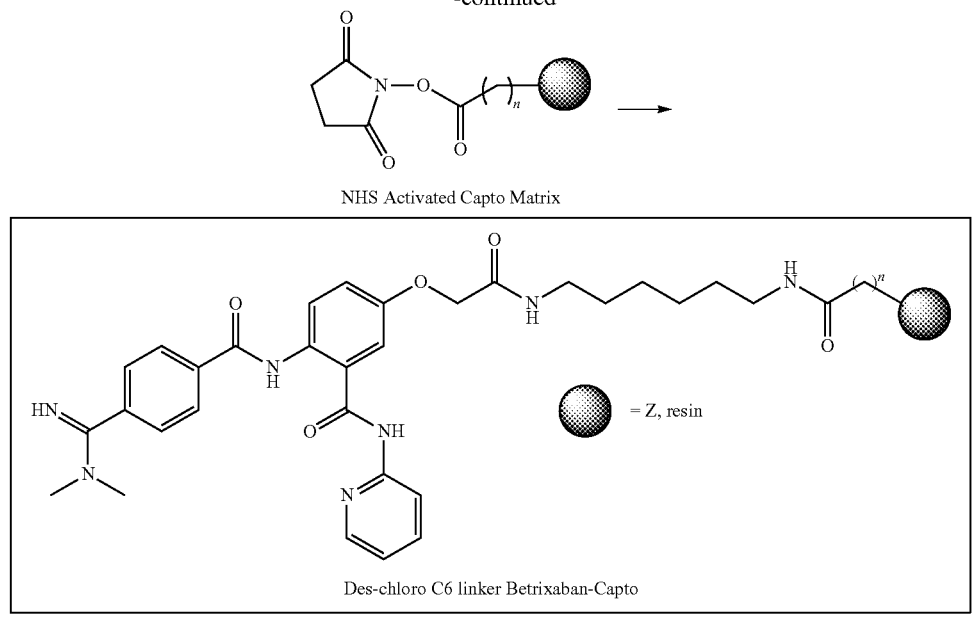

NHS Activated Capto Matrix

Des-chloro C6 linker Betrixaban-Capto

NHS-activated Capto matrix was hydrated with 1 mM HCl. The resin was washed 10 times with 2 mL volumes of 1 mM HCl. After this step, 20 mL of resin was obtained. The coupling solution was prepared by dissolving Compound A4 in buffer. This solution was diluted to 3.0 mL with buffer containing 0.1 M NaHCO$_3$, 0.5 M NaCl at pH 8.3. This coupling solution was added to the NHS-activated Capto matrix and reacted at room temperature for 3 hours while adjusting the pH at about 8.3. After completion of the coupling, unreacted resin was blocked with 0.1 M Tris-HCl buffer at pH 8.0. The coupled betrixaban NHS-Capto resin was washed 3 times with 0.1M acetate buffer pH 3 to 4 containing 0.5 M NaCl and 0.1 M Tris-HCl buffer pH 8 to 9 containing 0.5 M NaCl. Using this process, resins with 5, 11, 15 and 20 μm binding capacity were synthesized.

Similarly NHS activated sepharose resin 5 and 11 μm binding capacity were synthesized with A4.

Example 18

Purification of r-Antidote

A 1.0 mL column was packed with the betrixaban-affinity or des-chloro betrixaban-affinity resin. The cell culture BSR7 conditioned media (~1 mg r-Antidote) was loaded through pump at 0.2 mL/min. After the r-Antidote sample is loaded, the column was washed to baseline with equilibration buffer (20 mM Tris/250 mM NaCl/pH 7.4). The r-Antidote was stepwise eluted either with 0.5 M arginine in 25 mM Na-acetate buffer pH 5, or with 0.5 M benzamidine buffers (20 mM acetate, pH 5.0).

1 N sodium hydroxide wash and treatment with equilibration buffer 20 mM Tris/HCl, 250 mM NaCl, pH 7.4 regenerates the resin for reuse.

The eluent was analyzed using gel electrophoresis according to the following procedure:

SDS-PAGE (Sodium dodecyl sulfate-Polyacrylamide Gel Electrophoresis)

1. Sample Preparation-Reducing Conditions: 15 μL of sample is mixed with 5 μL of NuPAGE® LDS Sample Buffer and 2 μL of NuPAGE® Reducing Agent. Samples are then heated to 70° C. for 10 minutes
2. Noyes 10% Gel 1.0 mm, 12 well gel preparation. The cassette is removed from its packaging, rinsed with water, and then inserted into XCell SureLock™ Mini-Cell. The upper and lower chambers are filled with 1× NuPAGE® SDS Running Buffer; the wells are then rinsed twice with running buffer.
3. Sample Loading and Gel Running 20 μL of sample is loaded into a well. The gel is then run at 135 Volts, 400 mA for 65 minutes.
4. The cassette is then removed from the Mini-Cell; the gel is then removed from the cassette and fixed with 10% Acetic Acid/50% Methanol in water (v/v) for fifteen minutes. The gel is then stained over night using Gelcode Blue Stain Reagent. The gel is then destained with water.

FIG. 3 shows that r-Antidote is eluted with benzamidine. FIG. 4 shows that r-Antidote is eluted with arginine. The gel electrophoresis in FIG. 3 shows that benzamidine was effective in eluting r-Antidote from both betrixaban-affinity and des-chloro betrixaban-affinity columns, as compared to NaCl (compare lanes 4 and 5 from right to lanes 2 and 3 from right). The ability of arginine to elute r-Antidote, to some degree, depends on the column type. From betrixaban-affinity column, arginine was able to elute r-Antidote, but not as effective as benzamidine (compare lanes 2 and 3 in FIG. 4). From des-chloro betrixaban-affinity columns, however, arginine appeared even more effective than benzamidine (FIG. 4, lanes 4 and 5).

Example 19

Process for the Packing of the Column Followed by Purification

Sepharose Affinity Resin

A 1.0 mL column was packed with the betrixaban-NHS-Sepharose affinity or des-chloro betrixaban-NHS-Sepharose affinity resin prepared according to Example 8. Cell culture EB2 conditioned media (~1 mg r-Antidote) was loaded through pump at 0.2 mL/min. After the antidote sample is loaded the column was washed to baseline with equilibration buffer (20 mM Tris/250 mM NaCl/pH 7.4). The antidote was then stepwise eluted either with 0.5 M arginine in 25 mM Na-acetate, pH 5 or 0.5 M benzamidine buffers.

Figure 5:
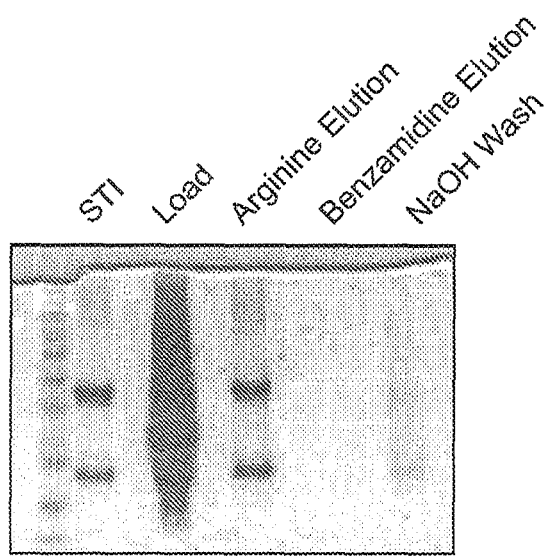
FIGS. 5 and 6 show the elution profiles as described in Example 11.
Figure 6:
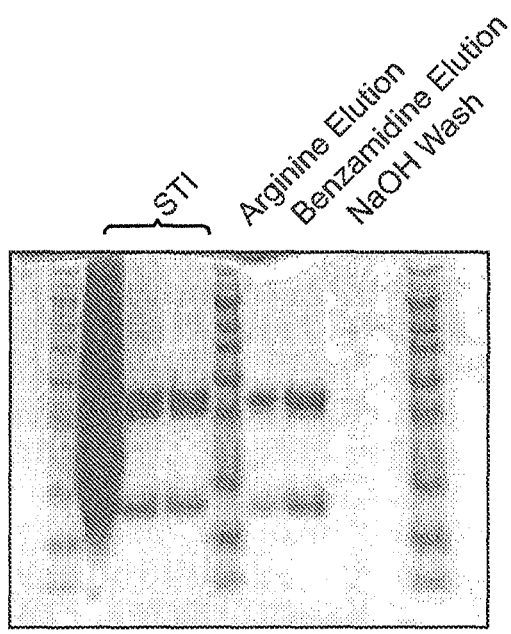

The SDS-PAGE of purified r-Antidote are shown in FIGS. 5 and 6. FIG. 5 shows complete elution of the antidote with 500 mM arginine from des-chloro betrixaban-NHS-Sepharose affinity resin. Lane 1 shows the SDS-PAGE of the equilibration buffer wash. Lane 2 shows the SDS-PAGE of the antidote purified with STI affinity resin. Lane 3 shows the unpurified antidote. Lane 4 shows antidote eluted with arginine buffer. Lanes 5 and 6 show elution with benzamidine buffer and wash with NaOH, respectively, after elution by arginine buffer, indicating that substantially all antidote was eluted by arginine buffer.

FIG. 6 shows partial elution of the antidote with 500 mM arginine and complete elution with 500 mM of benzamidine from betrixaban-NHS-Sepharose affinity resin. Lane 2 shows the SDS-PAGE of the unpurified antidote. Lanes 3 and 4 show the SDS-PAGE of antidote purified with STI affinity resin. Lane 6 shows antidote eluted with arginine buffer. Lane 7 shows that a significant amount of antidote was eluted with benzamidine buffer after elution by arginine buffer, indicating partial elution by arginine buffer.

Figure 7:
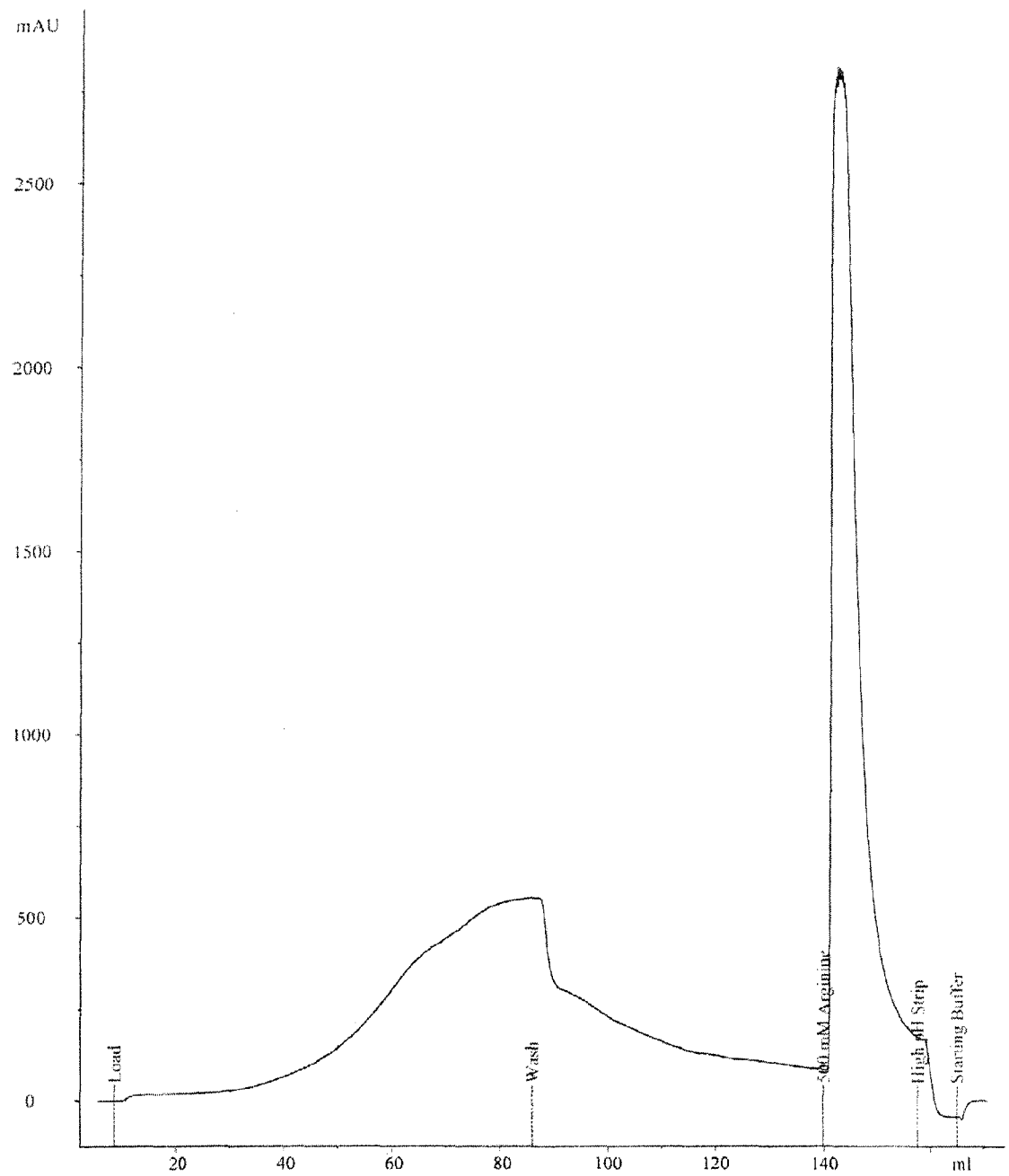
FIGS. 7 and 8 show the loading capacity of des-chloro betrixaban-NHS-Sepharose affinity resin and antidote recovery as monitored by ultraviolet (UV) spectra at 280 nm described in Example 19.
Figure 8:
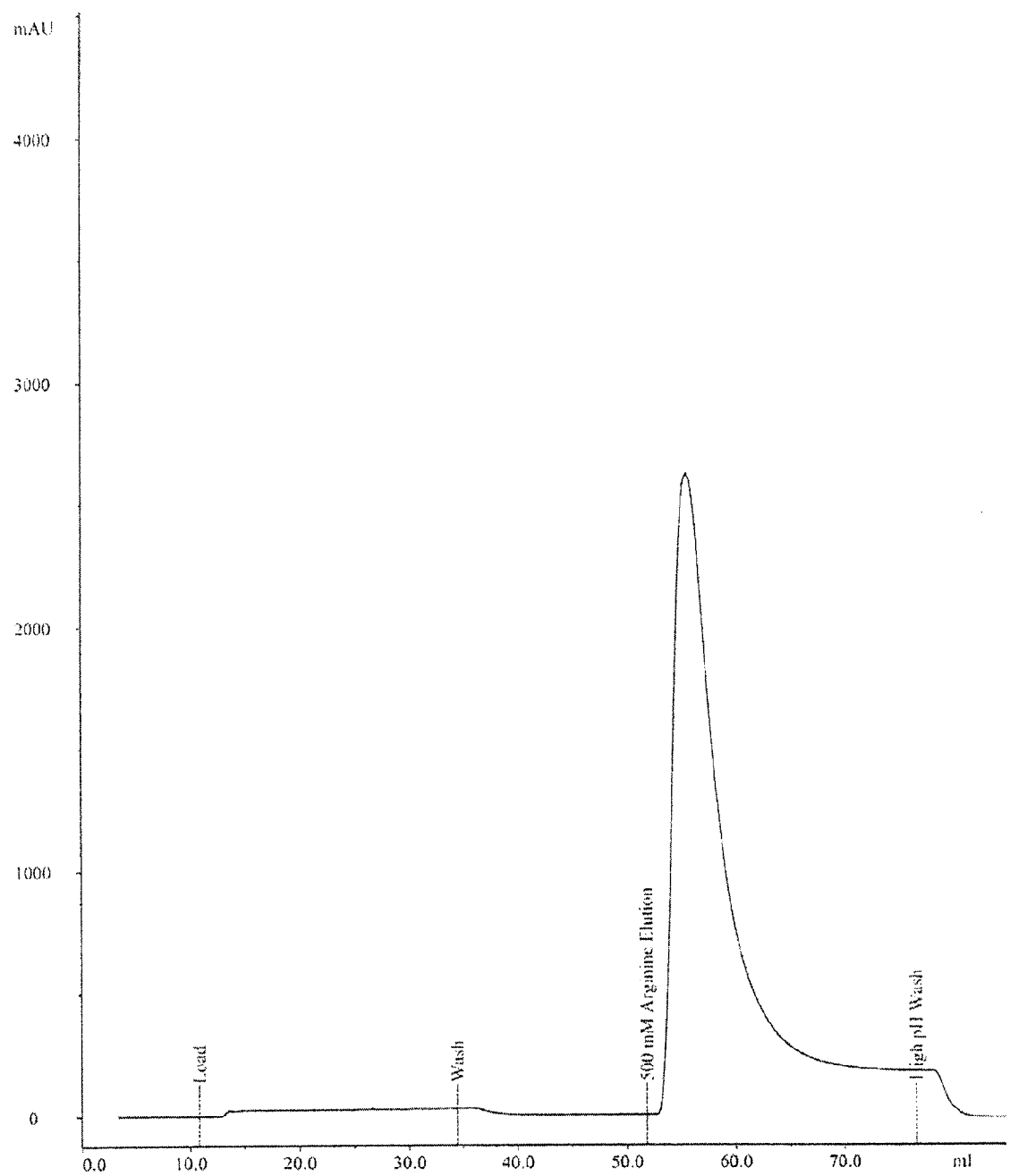

12 mg of r-Antidote was loaded to a des-chloro betrixaban-NHS-Sepharose affinity resin at 15 mg antidote per mL of resin (80% capacity, FIG. 7). 10 mg of antidote was recovered after elution (83% of recovery rate, FIG. 8).

Capto Resin

SMI Capto resins were prepared using a 2.0 mL column packed with des chloro-C6 Betrixaban linker A4 with NHS Activated Capto Resin prepared according to Example 17. Stage 31 Format A Culture Fluid was loaded through pump on 5, 11, 15 and 20 μM/mL SMI Capto column. After the antidote sample was loaded (1% Triton, 0.3% TnBP), the column was washed to baseline with equilibration buffer (20 mM Tris/250 mM NaCl/pH 7.4). The antidote was then stepwise eluted with 1 M arginine in 20 mM Tris/HCl, at pH 7.4.

Figure 9:
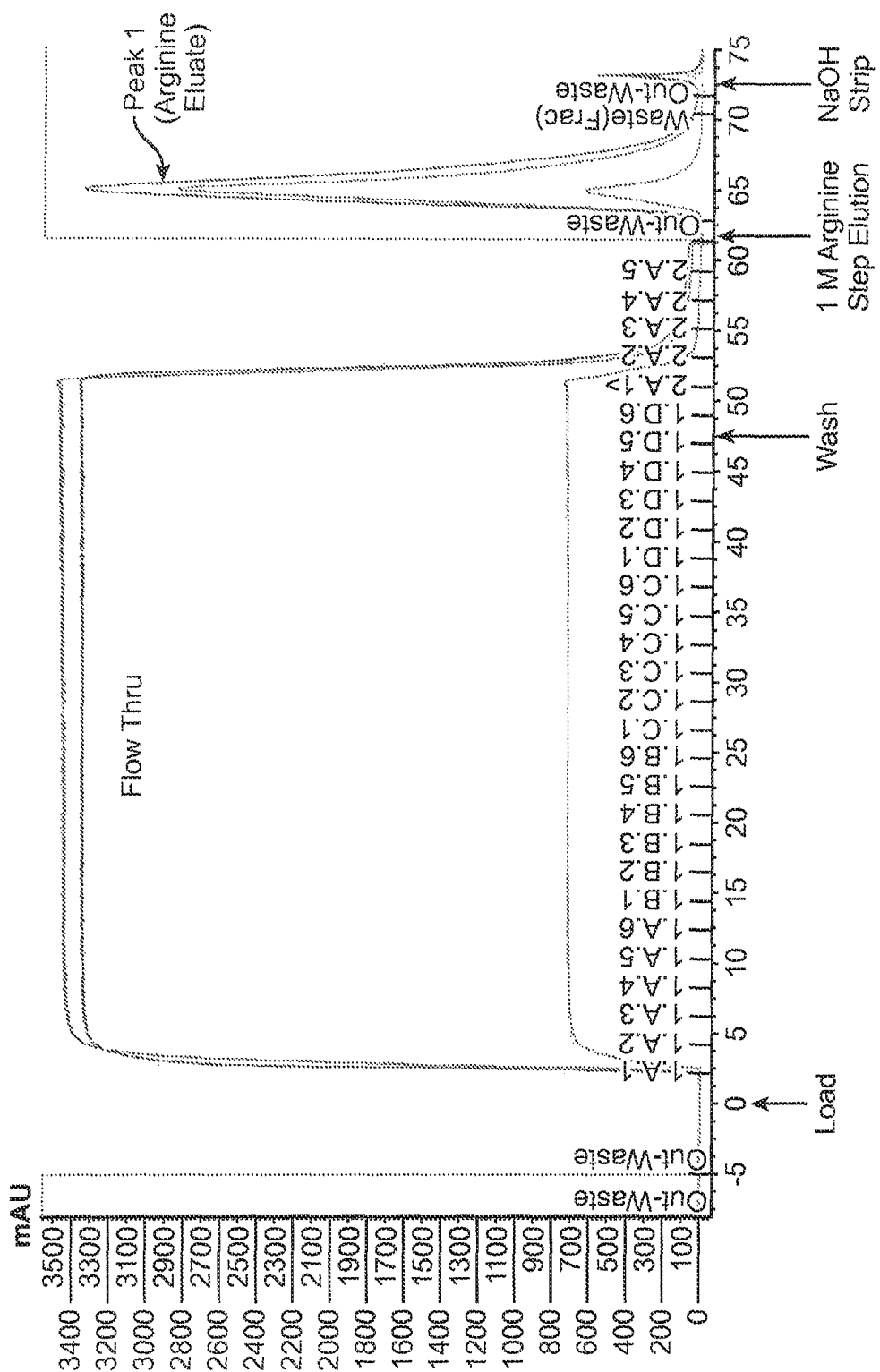
FIG. 9 shows the antidote recovery using des-chloro betrixaban C6 linker (A4)-Capto 5 μm affinity resin as monitored by ultraviolet (UV) spectra at three different wavelenghths: 260 nm, 280 nm, and 320 nm as described in Example 19.

90 mg of r-Antidote was loaded to a des-chloro betrixaban compound A4-5 μm SMI Capto Prototype resin and 42.9 mg (47.7% yield) mg of antidote was recovered after elution (FIG. 9).

Figure 10:
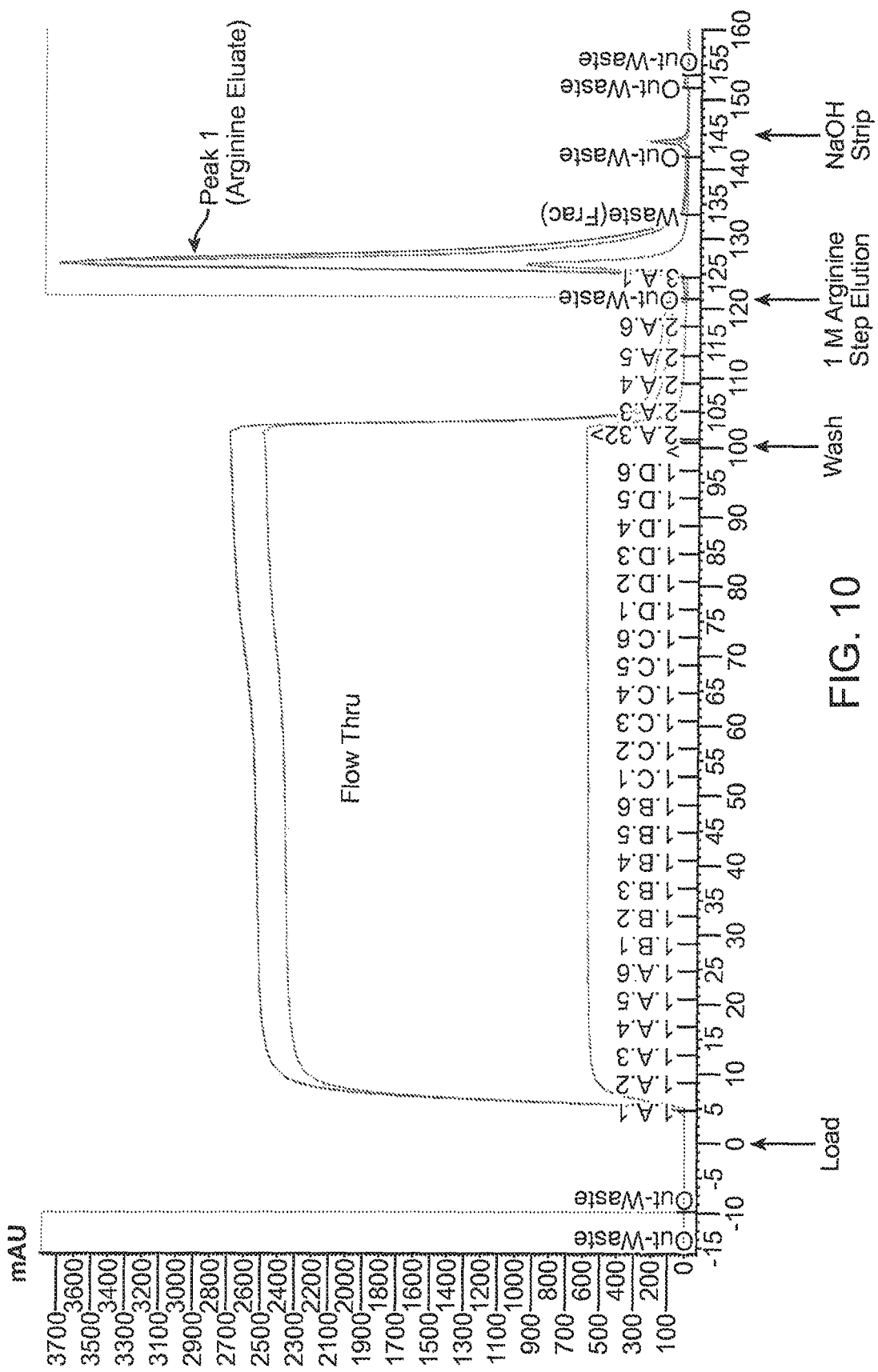
FIG. 10 shows the antidote recovery using des-chloro betrixaban C6 linker (A4)-Capto 11 μm affinity resin as monitored by ultraviolet (UV) spectra at three different wavelenghths: 260 nm, 280 nm, and 320 nm as described in Example 19.

90 mg of r-Antidote was loaded to a des-chloro betrixaban compound A4-11 μm SMI Capto Prototype resin and 56.6 mg (62.9%) of antidote was recovered after elution (FIG. 10).

Figure 11:
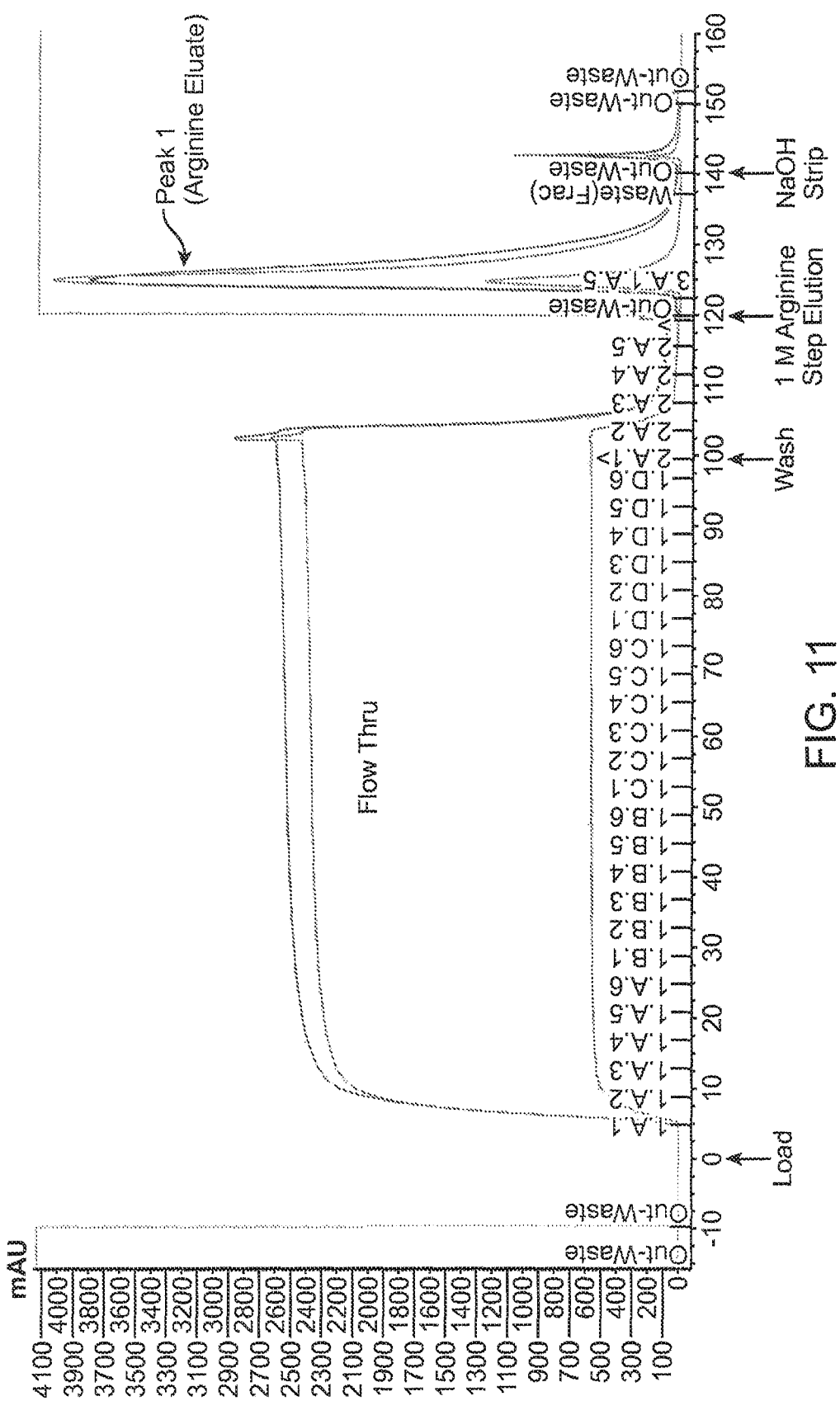
FIG. 11 shows the antidote recovery using des-chloro betrixaban C6 linker (A4)-Capto 15 μm affinity resin as monitored by ultraviolet (UV) spectra at three different wavelenghths: 260 nm, 280 nm, and 320 nm as described in Example 19.

90 mg of r-Antidote was loaded to a des-chloro betrixaban compound A4-15 μm SMI Capto Prototype resin and 64.5 mg (71.7%) of antidote was recovered after elution (FIG. 11).

Figure 12:
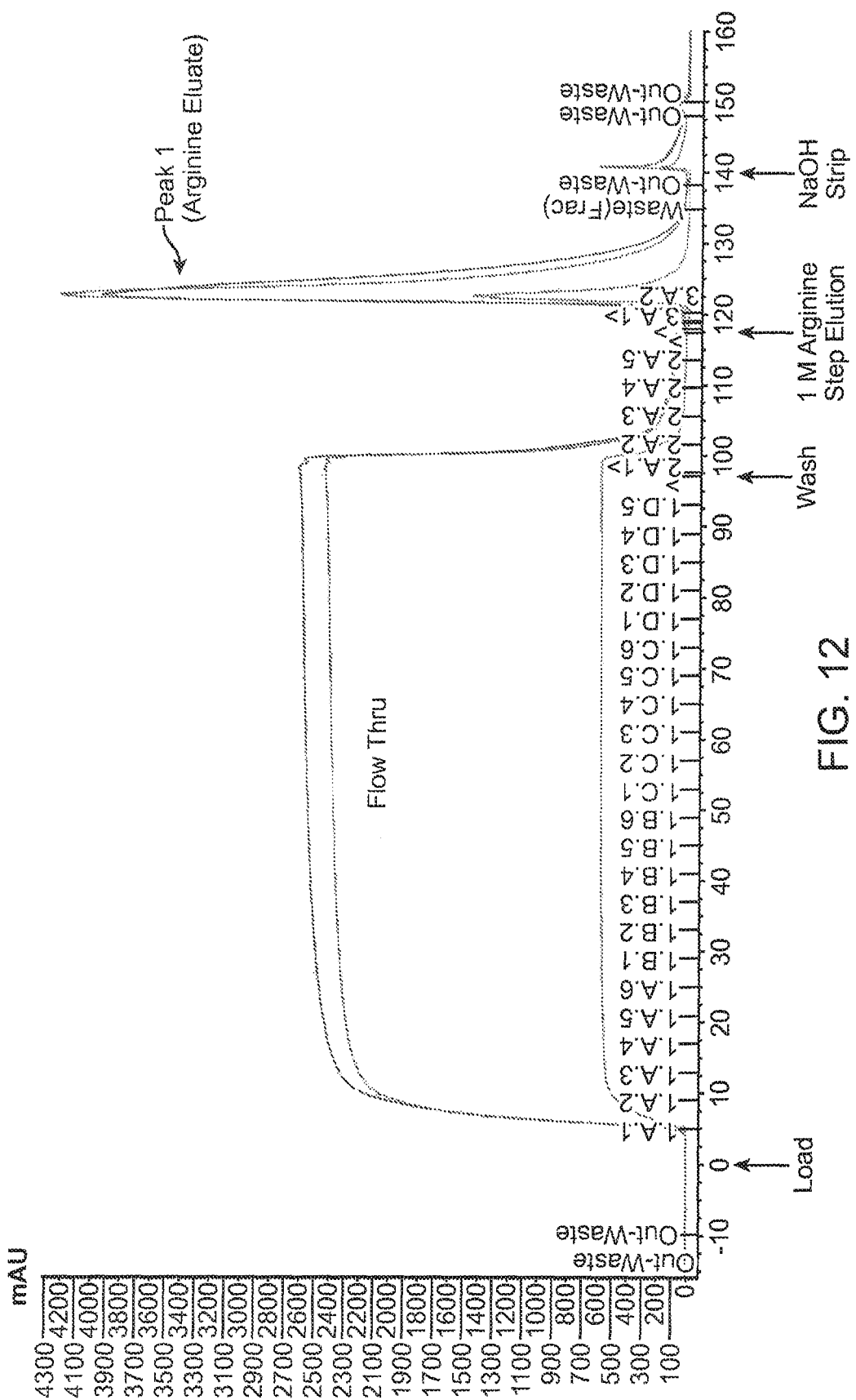
FIG. 12 shows the antidote recovery using des-chloro betrixaban C6 linker (A4)-Capto 20 μm affinity resin as monitored by ultraviolet (UV) spectra at three different wavelenghths: 260 nm, 280 nm, and 320 nm as described in Example 19.

90 mg of r-Antidote was loaded to a des-chloro betrixaban compound A4-20 μm SMI Capto Prototype resin and 63.2 mg (70.2%) of antidote was recovered after elution (FIG. 12).

The plots for FIG. 9-12 are in triplicates as they are run at three different wavelenghths: 260 nm, 280 nm, and 320 nm.

Example 20

Comparison of Small Molecule Inhibitor Affinity Sepharose Resin with Soyabean Trypsin Inhibitor (STI) Affinity Resin Antidote purification using small molecule inhibitor (des-chloro betrixaban) affinity Sepharose resin was compared with STI affinity resin. A minimum 3-fold higher binding capacity for small molecule inhibitor affinity Sepharose resin was obtained compared to STI affinity resin.

Approximately 400 μg of r-Antidote eluted from small molecule inhibitor or STI affinity column was concentrated to 3-5 mg/mL and buffer exchanged 25 fold into 1 yo formulation buffer using Amicon 10 kDa Ultracel centrifugal filter (Millipore UFC501096, 0.5 mL).

Table 5 shows the purification results using small molecule inhibitor affinity Sepharose resin or STI affinity resin. The small molecule inhibitor affinity resin consistently gave higher percentage of the alpha form (which is preferred) and lower percentage of the beta form than the STI affinity resin. It is preferred that the purified antidote contains no more than 10% of the beta form.

The yield of the antidote purified using small molecule inhibitor affinity resin is higher than the antidote purified by a 9-10 step GMP process with similar impurity profiles. The 9-10 step GMP process comprises four chromatography steps including a multi-modal cation exchange (Capto MMC, GE Healthcare) column, a multi-modal anion exchange (Capto adhere, GE Healthcare) column, a ceramic hydroxyapatite column (CHT, Bio-Rad) and a hydrophobic interaction column with a yield of about 55% for the four steps.

TABLE 5

| Resin | Alpha Form Peak Area (%) | Beta Form Peak Area (%) |
|---|---|---|
| GMP | 89.45 | 8.06 |
| Small Molecule Inhibitor Affinity Sepharose Resin | 89.16 | 7.41 |
| | 89.41 | 7.48 |
| | 88.97 | 7.33 |
| STI Affinity Resin | 82.38 | 15.22 |
| | 84.50 | 12.98 |

Example 21

Purification with Small Molecule Inhibitor Affinity Capto Resin

SMI Four Step Method

Antidote purification was carried out using small molecule inhibitor (Des chloro-C6 Betrixaban linker A4) affinity 11 um Capto resin as below:

Sample Preparation 100 mL of frozen CCF (clarified culture fluid) was thawed at room temperature. The CCF was centrifuged to remove precipitate and then filtered thru a 0.22 um filter. The filtrate was treated with 10% Triton for a final concentration of 1% and made 0.3% with N-Tributyl Phosphate. The resulting solution was then stirred at room temp for 30 minutes for viral inactivation.

SMI Capture Step (1)

The treated CCF was applied to a 2.0 mL (5×100 mm) 11 um SMI Capto column equilibrated with 20 mM Tris/HCl, 200 mM NaCl, pH 7.4 with a flow rate of 200 cm/hr. The chromatography was monitored at UV wavelengths 280, 260, and 320 nm; conductivity and pH were also monitored. 5 CV fractions were collected for the sample application. After the sample finished applying, the column was washed with 10 CV of 20 mM Tris/HCl, 200 mM NaCl, pH 7.4 and then washed with 10 CV 20 mM Tris/HCl, pH 7.4.

The bound Antidote was eluted with a 20 CV Linear Gradient of 0→1 M Arginine in 20 mM Tris/HCl, pH 7.4. Fractionation was started at 50 mAU and ended at 100 mAU; a single fraction was collected (SMI Eluate).

Adhere Step (2)

The SMI Eluate was diluted 1:15 with 25 mM Tris/HCl, pH 8.0 and applied to a 4.7 mL Capto Adhere GE-HiScreen column was equilibrated with 25 mM Tris/HCl, 50 mM NaCl, pH 8.0 with a flow rate of 200 cm/hr. The chromatography was monitored at UV wavelengths 280, 260, and 320 nm; conductivity and pH were also monitored. After the sample finished applying, the column was washed with 10 CV of 25 mM Tris/HCl, 50 mM NaCl, pH 8.0.

The bound Antidote was step eluted with 335 mM Arginine, 50 mM HEPES, pH 7.0 Fractionation was started at 50 mAU and ended at 100 mAU; a single fraction was collected (Adhere Eluate).

CHT Step (3)

The Adhere Eluate was diluted 1:5 with 50 mM MES, 5 mM Sodium Phosphate, pH 7.0 and applied to a 5 mL Bio-Scale Mini CHT, Type 1 column equilibrated with 50 mM MES, 5 mM Sodium Phosphate, pH 7.0 with flow rate of 200 cm/hr. The chromatography was monitored at UV wavelengths 280, 260, and 320 nm; conductivity and pH were also monitored. After the sample finished applying, the column was washed with 5 CV of 50 mM MES, 5 mM Sodium Phosphate, pH 7.0.

The bound Antidote was eluted with a 15 CV Linear Gradient of 0→2 M NaCl in 50 mM MES, 5 mM Sodium Phosphate, pH 7.0. Fractionation was started at 200 mAU and ended at 100 mAU; a single fraction was collected (CHT Eluate).

Octyl Step (4)

The CHT Eluate was applied to a 1 mL Octyl Sepharose FF HiTrap Column equilibrated with 50 mM MES, 5 mM Sodium Phosphate, 1 M NaCl, pH 7.0 with a flow rate of 200 cm/hr. The chromatography was monitored at UV wavelengths 280, 260, and 320 nm; conductivity and pH were also monitored. After the sample finished applying, the column was washed with 50 mM MES, 5 mM Sodium Phosphate, 1 M NaCl, pH 7.0.

Figure 13:
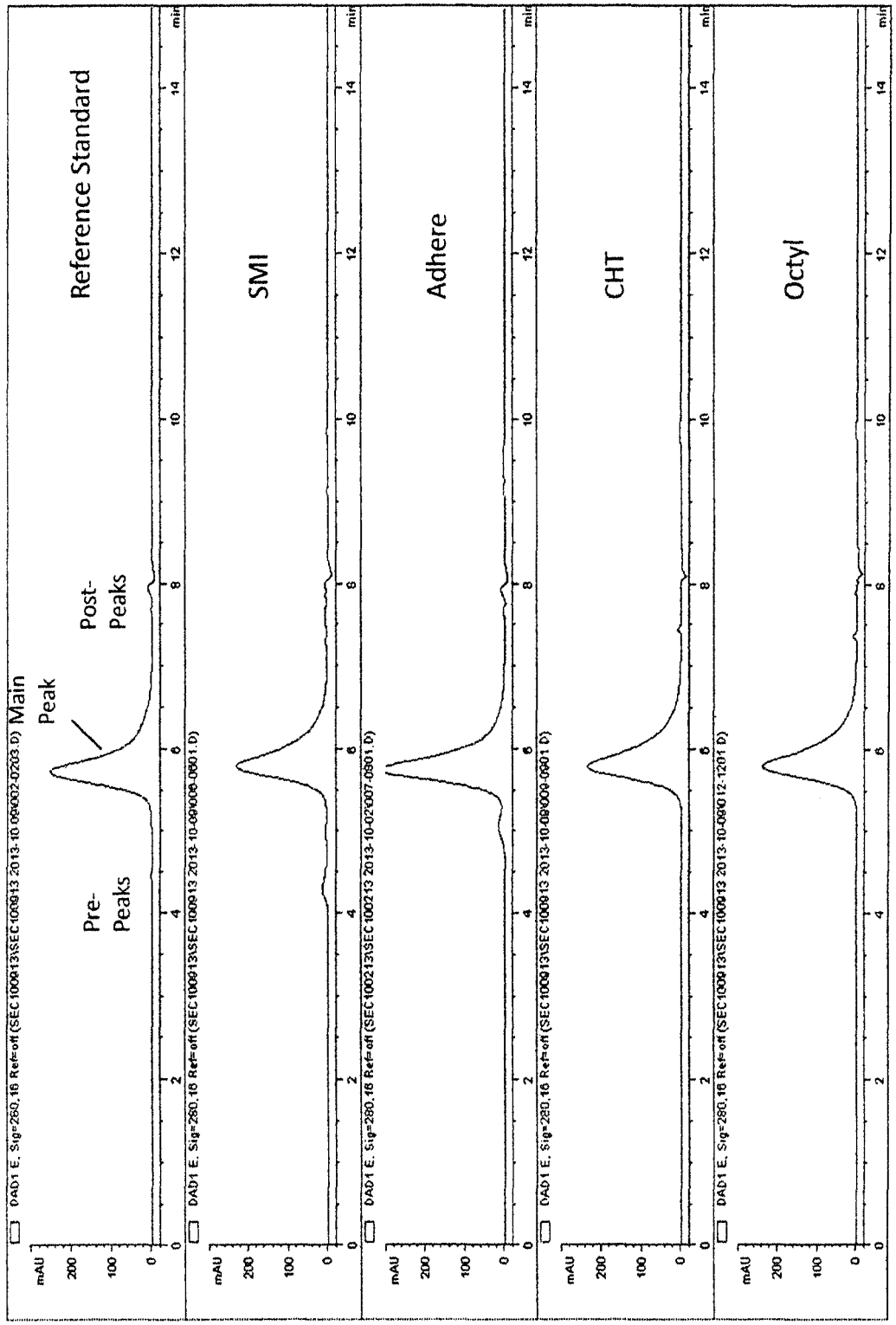
FIG. 13 shows the antidote purification using des-chloro betrixaban C6 linker (A4) Capto 11 μm affinity resin using the SMI (small molecule inhibitor) Four Step Method of Example 21.

This is a Pass-Thru Collection; fractionation was started at 50 mAU and ended at 50 mAU; a single fraction was collected (Octyl Pool). The data is as shown in the table below and also in FIG. 13. The

| Process Step/Sample | % Pre-Peaks | % Main Peak | % Beta Peak | % Post-Peaks | Conc mg/mL (by TPA) | RT min Main Peak |
|---|---|---|---|---|---|---|
| SMI | 1.7 | 87.3 | 9.5 | 1.5 | 1.0 | 20.5 |
| Adhere | 1.1 | 88.1 | 10.8 | 0.0 | 2.6 | 20.4 |
| CHT | 0.7 | 89.4 | 9.9 | 0.0 | 1.1 | 20.4 |
| Octyl | 0.7 | 89.4 | 10.0 | 0.0 | 0.9 | 20.4 |

Four Step Method Using MMC Capture Step (Non-Affinity and Non-Specific)

Figure 14:
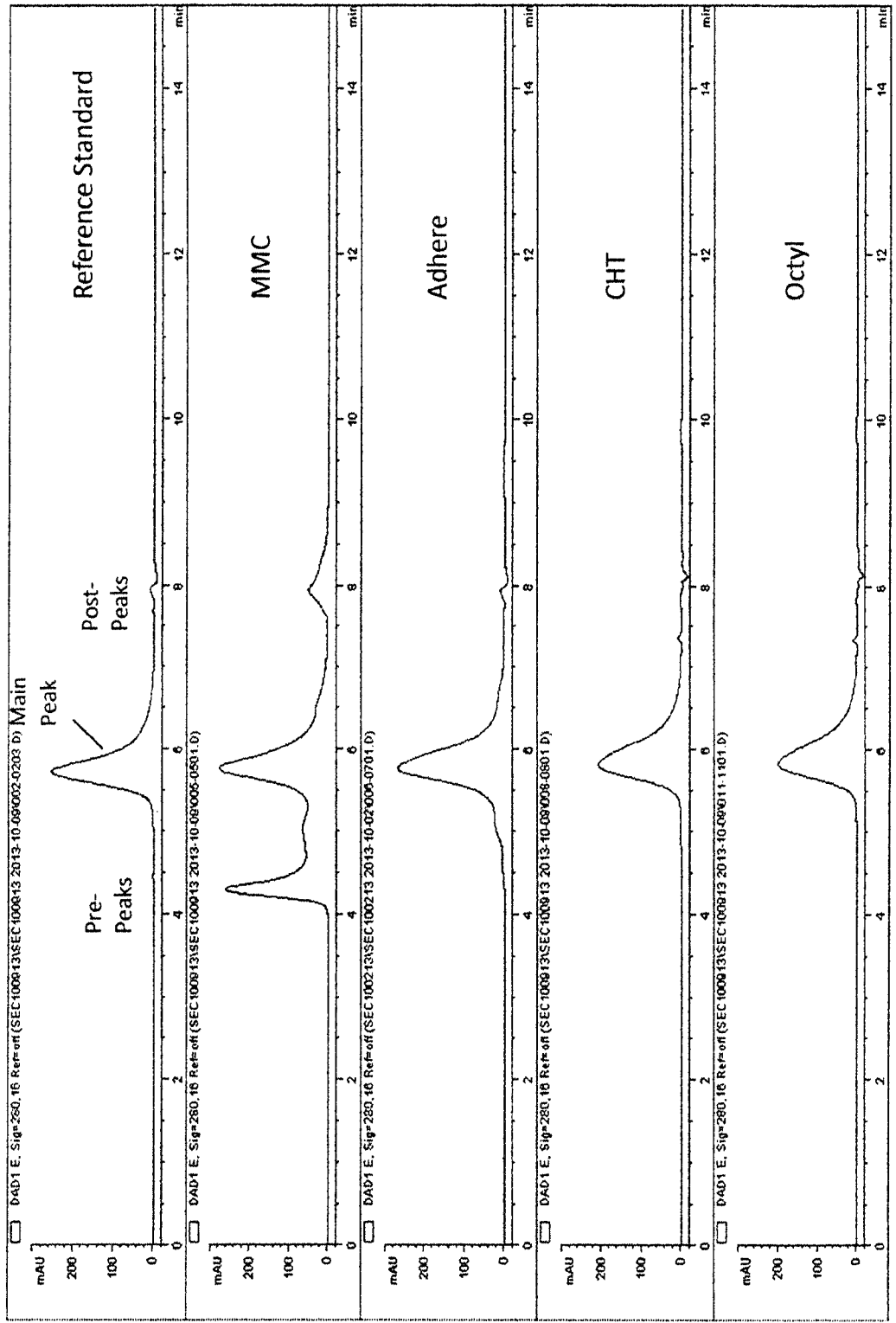
FIG. 14 shows the antidote purification using the Four Step Method using MMC (multi-modal column) capture step of Example 21.

Alternatively, antidote purification was carried out using MMC capture step (1), Adhere Step (2), CHT Step (3), and Octyl Step (4). The data is shown in Table below and in FIG. 14. FIG. 14 as compared to FIG. 13 indicates that the SMI four step method works significantly better than the four step method using MMC capture step that does not use the SMI.

| Process Step/Sample | % Pre-Peaks | % Main Peak | % Beta Peak | % Post-Peaks | Conc mg/mL (by TPA) | RT min Main Peak |
|---|---|---|---|---|---|---|
| MMC | 5.3 | 68.2 | 10.1 | 16.5 | 4.6 | 20.4 |
| Adhere | 4.8 | 79.8 | 11.8 | 3.6 | 2.4 | 20.5 |
| CHT | 2.6 | 85.8 | 10.1 | 1.5 | 1.0 | 20.5 |
| Octyl | 2.4 | 87.0 | 10.1 | 0.4 | 0.8 | 20.4 |

Alternate Methods

SMI Three Step Method

Alternative purification method was developed to exploits the power of the SMI affinity capture step and remove the CHT and Octyl columns from the process. The CHT column is difficult to run, under loading results in poor recovery and over loading does not clear impurities. Octyl column is not necessary for Host Cell Protein (HCP) removal as SMI, $1^{st}$ capture step cleans HCP significantly. Thus, alternatively, antidote purification was carried out using small molecule inhibitor (Des chloro-C6 Betrixaban linker A4) affinity 20 μm Capto resin using SMI Capture Step (1) and Adhere Step (2) as listed above followed by the following MMC ImpRes step (3).

MMC ImpRes

The Adhere Eluate was diluted 1:15 with 50 mM HEPES, 50 mM NaCl, pH 7.0 and applied to a 4.7 mL MMC ImpRes Column equilibrated with 50 mM HEPES, 50 mM NaCl, pH 7.0 with a flow rate of 200 cm/hr. The chromatography was monitored at UV wavelengths 280, 260, and 320 nm; conductivity and pH were also monitored. After the sample finished applying, the column was washed with 10 CV of 50 mM HEPES, 50 mM NaCl, pH 7.0.

The bound Antidote was Step Eluted with 350 mM Arginine, 50 mM Tris/HCl, pH 8.0 Fractionation was started at 50 mAU and ended at 100 mAU; a single fraction was collected (MMC ImpRes Eluate).

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

Other embodiments are within the following claims. In addition, where features or aspects of the disclosure are described in terms of Markush groups, those skilled in the art will recognize that the disclosure is also thereby described in terms of any individual member or subgroup of members of the Markush group.

What is claimed is:

1. A compound selected from:

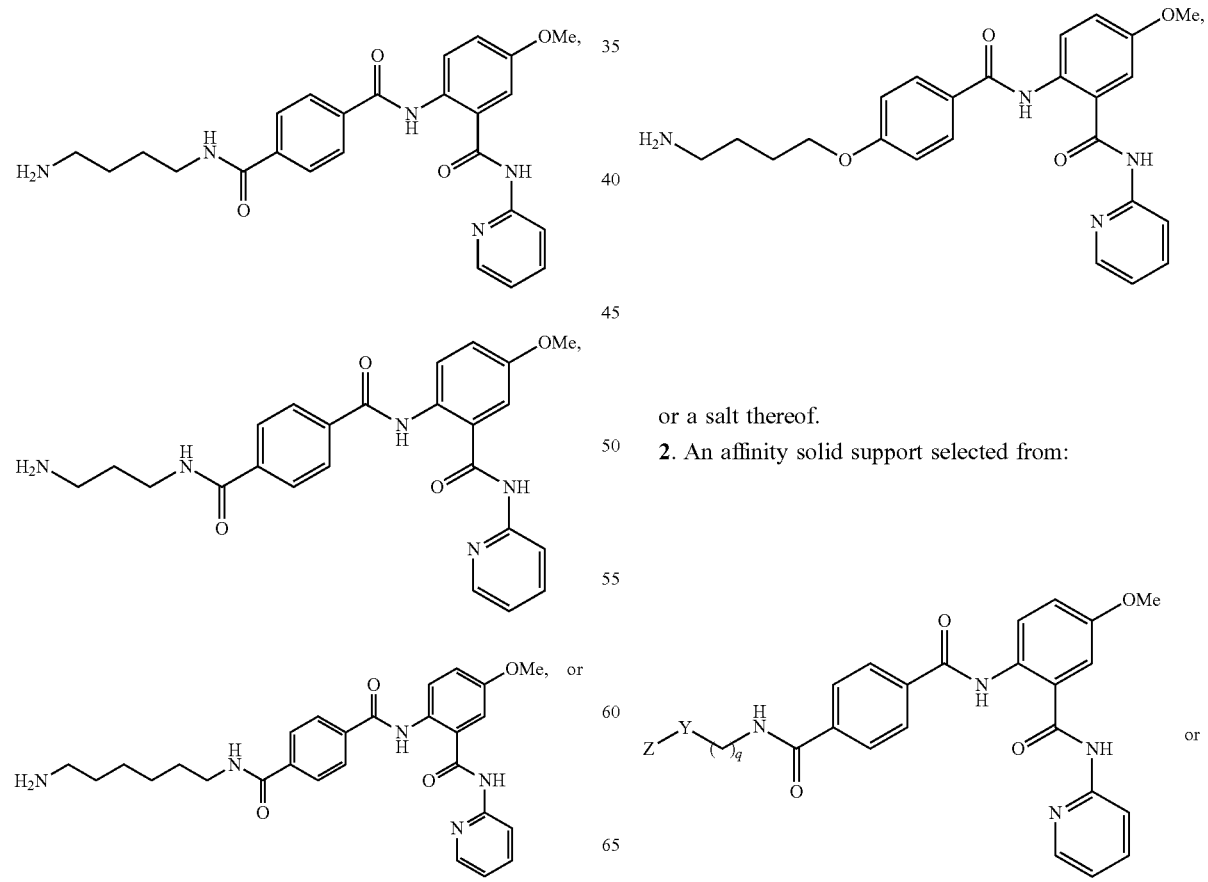

or a salt thereof.

2. An affinity solid support selected from:

-continued

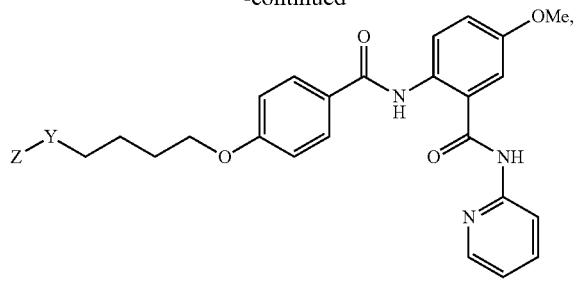

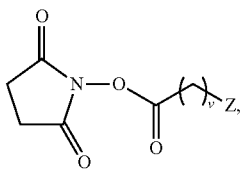

wherein Z is a solid support.

6. The kit of claim 5, wherein Z is an agarose resin.

7. A method for purifying a fXa derivative comprising (1) adding a first composition comprising the fXa derivative to an affinity solid support of claim 2 or a salt thereof to form a second composition comprising the fXa derivative and the affinity solid support of claim 2, and (2) eluting the fXa derivative from the second composition with an elution buffer comprising a competitive agent, wherein the fXa derivative is a polypeptide comprising the amino acid sequence of SEQ ID NO: 1, 2 or 4, or a polypeptide having at least about 80% sequence identity to SEQ ID NO: 1, 2 or 4 and further wherein the derivative is capable of binding to a fXa inhibitor and does not assemble into a prothrombinase complex.

or a salt thereof,
wherein:
Y—Z is

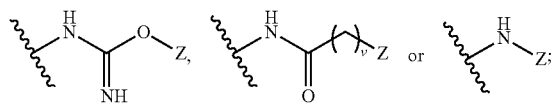

Z is a solid support;
q is 3, 4 or 6; and
v is 1, 2, 3, 4, 5, 6 or 7.

3. The affinity solid support of claim 2, wherein Z is an agarose resin.

4. A kit for purifying a serine protease comprising (1) an affinity solid support of claim 2, and (2) an elution buffer comprising a competitive agent.

5. A kit for purifying a serine protease comprising a compound of claim 1 and a resin of the formula NC—O—Z or 8. The method of claim 7, wherein the competitive agent is arginine and/or benzamidine, or a salt thereof.

9. The method of claim 7, wherein the fXa derivative is a polypeptide comprising the amino acid sequence of SEQ ID NO: 2, or a polypeptide having at least about 90% sequence identity to SEQ ID NO: 2.

10. The method of claim 9, wherein the polypeptide has at least about 95% sequence identity to SEQ ID NO: 2.

* * * * *

SEQUENCE LISTING

<160> NUMBER OF SEQ ID NOS: 5

<210> SEQ ID NO 1
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
    210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
    290                 295                 300

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
                325                 330                 335

Lys Trp Ile Asp Arg Ser Met Lys Thr Arg Gly Leu Pro Lys Ala Lys
            340                 345                 350

Ser His Ala Pro Glu Val Ile Thr Ser Ser Pro Leu Lys
            355                 360                 365

<210> SEQ ID NO 2
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
    130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
    210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Phe Ile Ile Thr Gln Asn
            260                 265                 270

Met Phe Cys Ala Gly Tyr Asp Thr Lys Gln Glu Asp Ala Cys Gln Gly
        275                 280                 285

Asp Ala Gly Gly Pro His Val Thr Arg Phe Lys Asp Thr Tyr Phe Val
    290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
            340                 345                 350

```
Ile Thr Ser Ser Pro Leu Lys
        355

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Lys Arg Arg Lys Arg
1               5

<210> SEQ ID NO 4
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
    130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
    210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Phe Ile Ile Thr Gln Asn
            260                 265                 270
```

```
Met Phe Cys Ala Gly Tyr Asp Thr Lys Gln Glu Asp Ala Cys Gln Gly
            275                 280                 285

Asp Ala Gly Gly Pro His Val Thr Arg Phe Lys Asp Thr Tyr Phe Val
        290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg
            340

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Leu Pro Lys Ala Lys Ser His Ala Pro Glu Val Ile Thr Ser Ser
1               5                   10                  15

Pro Leu Lys
```